US010095836B2

(12) United States Patent
Jung et al.

(10) Patent No.: US 10,095,836 B2
(45) Date of Patent: Oct. 9, 2018

(54) COMPUTATIONAL SYSTEMS FOR BIOMEDICAL DATA

(75) Inventors: Edward K. Y. Jung, Bellevue, WA (US); Royce A. Levien, Cambridge, MA (US); Robert W. Lord, Seattle, WA (US); Mark A. Malamud, Seattle, WA (US); Lowell L. Wood, Jr., Bellevue, WA (US)

(73) Assignee: GEARBOX LLC, Bellevue, WA (US)

( * ) Notice: Subject to any disclaimer, the term of this patent is extended or adjusted under 35 U.S.C. 154(b) by 1312 days.

(21) Appl. No.: 11/821,537

(22) Filed: Jun. 22, 2007

(65) Prior Publication Data
US 2008/0082582 A1 Apr. 3, 2008

Related U.S. Application Data

(63) Continuation-in-part of application No. 11/647,531, filed on Dec. 27, 2006, and a continuation-in-part of application No. 11/541,478, filed on Sep. 29, 2006.

(51) Int. Cl.
G01N 33/48 (2006.01)
G06F 19/00 (2018.01)
G16H 10/20 (2018.01)

(52) U.S. Cl.
CPC ........ *G06F 19/326* (2013.01); *G06F 19/3456* (2013.01); *G16H 10/20* (2018.01)

(58) Field of Classification Search
None
See application file for complete search history.

(56) References Cited

U.S. PATENT DOCUMENTS

| | | | |
|---|---|---|---|
| 5,910,421 A | 6/1999 | Small, Jr. et al. |
| 5,916,818 A | 6/1999 | Irsch et al. |
| 6,140,047 A | 10/2000 | Duff et al. |
| 6,190,909 B1 | 2/2001 | Levinson et al. |
| 6,219,674 B1 | 4/2001 | Classen |
| 6,317,700 B1 | 11/2001 | Bagne |
| 6,493,637 B1 | 12/2002 | Steeg |
| 6,548,245 B1 | 4/2003 | Lilly et al. |
| 6,602,509 B1 | 8/2003 | Saint-Remy et al. |
| 6,759,234 B1 | 7/2004 | Gefter et al. |
| 7,024,369 B1 | 4/2006 | Brown et al. |
| 7,118,869 B2 | 10/2006 | Blumenfeld et al. |
| 7,177,675 B2 | 2/2007 | Suffin et al. |
| 7,198,895 B2 | 4/2007 | Mohanlal |
| 7,489,964 B2 | 2/2009 | Suffin et al. |
| 7,491,553 B2 | 2/2009 | Brown et al. |
| 7,732,135 B2 | 6/2010 | Hershey et al. |
| 2001/0020240 A1 | 9/2001 | Classen |
| 2002/0055855 A1 | 5/2002 | Cule et al. |
| 2002/0083080 A1 | 6/2002 | Classen |
| 2002/0187158 A1 | 12/2002 | Mahler et al. |
| 2003/0046110 A1 | 3/2003 | Gogolak |
| 2003/0074225 A1 | 4/2003 | Borsand et al. |
| 2003/0087320 A1 | 5/2003 | Vojdani |
| 2003/0099979 A1 | 5/2003 | Ohtani et al. |
| 2003/0104453 A1 | 6/2003 | Pickar et al. |
| 2003/0163353 A1 | 8/2003 | Luce et al. |
| 2003/0177512 A1 | 9/2003 | Avner |
| 2004/0024772 A1 | 2/2004 | Itai |
| 2004/0093331 A1 | 5/2004 | Garner et al. |
| 2005/0196752 A1 | 9/2005 | Blumenfeld et al. |
| 2006/0008834 A1 | 1/2006 | Margus et al. |
| 2006/0015952 A1 | 1/2006 | Filvaroff |
| 2006/0111292 A1 | 5/2006 | Khan et al. |
| 2006/0188913 A1 | 8/2006 | Krieg et al. |
| 2006/0200480 A1 | 9/2006 | Harris et al. |
| 2007/0054282 A1 | 3/2007 | Liew |
| 2007/0183978 A1 | 8/2007 | Preuss et al. |
| 2007/0288256 A1 | 12/2007 | Speier |
| 2007/0294113 A1 | 12/2007 | Settimi |
| 2008/0058407 A1 | 3/2008 | Baron et al. |
| 2009/0074711 A1 | 3/2009 | Glennie |
| 2010/0235184 A1 | 9/2010 | Firminger et al. |
| 2010/0235185 A1 | 9/2010 | Firminger et al. |
| 2010/0241448 A1 | 9/2010 | Firminger et al. |
| 2010/0241454 A1 | 9/2010 | Firminger et al. |
| 2010/0324936 A1 | 12/2010 | Vishnubhatla et al. |
| 2011/0112860 A1 | 5/2011 | Kehr |

FOREIGN PATENT DOCUMENTS

JP 03-292898 12/1991

OTHER PUBLICATIONS

U.S. Appl. No. 11/647,533, Jung et al.
Adjei, AA; "Pemetrexed (ALIMTA), a novel multitargeted antineoplastic agent"; Clin Cancer Res.; bearing a date of Jun. 15, 2004; pp. 4276s-4280s (abstract p. 1); vol. 10, No. 12, Pt 2; PubMed; located at http://www.ncbi.nlm.nih.gov/entrez/query.fcgi?db=pubmed &cmd=R; printed on Jul. 31, 2006.
"Allergen Online: Home of the farrp allergen protein database"; bearing dates of Jan. 2007 and 2006; pp. 1-3; University of Nebraska, Lincoln, NE; located at http://www.allergenonline.com; printed on Feb. 16, 2007.
"Allergy" pp. 1-8; Wikipedia, located at http://en.wikipedia.org/wiki/Allergy; printed on Jan. 24, 2007.
"Allergy Testing—Physician Overview", MDS Diagnostic Services, bearing a date of Nov. 9, 2006, p. 1, located at http://www.mdsdx.com/pring/MDS_Diagnostic_Services/Patients/TestInfo/Special/allergy3.asp.
Amoli, M.M., et al., "Polymorphism in the STAT6 gene encodes risk for nut allergy"; Genes and Immunity; bearing a date of Feb. 13, 2002; pp. 220-224; vol. 3; Nature Publishing Group.
Amouzou, Emile K., et al., "High prevalence of hyperhomocysteinemia related to folate deficiency and the 677C →T mutation of the gene encoding methylenetetrahydrofolate reductase in coastal West Africa[1-3]", American Journal of Clinical Nutrition, bearing a date of 2004; pp. 619-624; vol. 79; American Society for Clinical Nutrition; printed on Jul. 31, 2006.

(Continued)

*Primary Examiner* — Jerry Lin

(57) ABSTRACT

Methods, apparatuses, computer program products, devices and systems are described that are configured for accepting an input identifying at least one treatment target in search of an agent; accessing at least one dataset containing at least one agent for use in the context of the at least one treatment target; applying at least one filter criterion to at least one dataset to identify a subset of the at least one dataset, the subset of the at least one dataset associated with a defined level of at least one adverse event associated with administration of the at least one agent; and presenting the at least one agent in response to the subset of the at least one dataset.

20 Claims, 22 Drawing Sheets

(56) References Cited

OTHER PUBLICATIONS

Asero, Riccardo, et al.; "IgE-Mediated food allergy diagnosis: Current status and new perspectives"; Mol. Nutr. Food Res; bearing dates of 2007; Jul. 31, 2006 and Aug. 4, 2006; pp. 135-147; vol. 51.
"A Single-blind Randomized Phase 3 Trial of ALIMTA (pemetrexed) plus Cisplatin versus Cisplatin Alone in Patients with Malignant Pleural Mesothelimoa"; Eli Lilly and Company; bearing dates of Nov. 15, 2004 and 2004; pp. 1-13; located at http://www.clinicalstudyresults.org/documents/company-study_36_0.pdf.
Bagga, Sandeep Kumar, "Multi-center clinical trial connectivity, express data management and SAS programming", bearing dates of Mar. 11, 2002 and Aug. 4, 2006; pp. 1-2; PHARMABIZ.com; located at http://www.phamabiz.com/article/detnews.asp?articleid=11396&se; printed on Aug. 3, 2006.
Banik, Utpal, Ph.D., et al., "Cross-reactivity Implications for Allergy Diagnosis", News & Views, bearing a date of 2006, pp. 13-16, Issue 2, located at www.dpcweb.com—under Technical Documents, News & Views, 2006, Issue 2.
Bataille, Veronique, "Genetic Factors in Nickel Allergy", Journal of Investigative Dermatology, bearing a date of Dec. 2004, pp. xxiv-xxv, vol. 123, No. 6, The Society for Investigative Dermatology, Inc.
Bousquet, Jean, et al.; "Epigenetic inheritance of fetal genes in allergic asthma"; Allergy; bearing dates of 2004 and Aug. 13, 2003; pp. 138-147; vol. 59; Blackwell Munksgaard.
Bousquet, Jean, et al.; "Factors responsible for differences between asymptomatic subjects and patients presenting and IgE sensitization to allergens"; Allergy; bearing dates of Dec. 2, 2005 and 2006; pp. 671-680; vol. 61; Blackwell Munksgaard.
Brusic, V., et al.; "Allergen databases"; Allergy; bearing a date of Mar. 26, 2003; pp. 1093-1100; vol. 58; Blackwell Munksgaard.
Burks, A. Wesley; "Recombinant Peanut Allergen *Ara h* I Expression and IgE Binding in Patients with Peanut Hypersensitivity"; J. Clin. Invest; bearing a date of Oct. 1995; pp. 1715-1721; vol. 96.
Calvert, AH; "Biochemical pharmacology of pemetrexed"; Oncology; bearing a date of Nov. 2004; pp. 13-17 (abstract p. 1); vol. 18, No. 13 Suppl 8; PubMed; located at http://www.ncbi.nlm.nih.gov/entrez/query.fcgi?db=pubmed&cmd=R; printed on Jul. 31, 2006.
Calvert, A. H., et al., "Clinical studies with MTA", Br J Cancer, bearing a date of 1998; pp. 35-40 (abstract, p. 1); vol. 78; Suppl 3; PubMed; located at http://www.ncbi.nlm.nih.gov/entrez/query.fcgi?db=pubmed&cmd=R . . . , printed on Jul. 31, 2006.
Calvert, H.; "Folate Status and the safety profile of antifolates"; Semin Oncol., bearing a date of Apr. 2002; pp. 3-7 (abstract p. 1); vol. 29; No. 2 Suppl 5; PubMed; located at http://www.ncbi.nlm.nih.gov/entrez/query.fcgi?db=pubmed&cmd=R; printed on Jul. 31, 2006.
Carmel, Ralph, et al.; "Serum cobalamin, homocysteine, and methylmalonic acid concentrations in a multiethnic elderly population: ethnic and sex differences in cobalamin and metabolite abnormalities 1-3"; Am J Clin Nutr; bearing a date of 1999; pp. 904-910; vol. 70; American Society of Clinical Nutrition; printed on Jul. 31, 2006.
Cascorbi, I.; "Pharmacogenetics of cytochrome p4502D6: genetic background and clinical implication"; Eur J Clin Invest.; bearing dates of Nov. 2003 and Jun. 6, 2006; pp. 17-22 (abstract p. 1); vol. 33, Suppl 2; PubMed; located at http://www.ncbi.nlm,nih.gov/entrez/query.fcgi?CMD=displayfilter; printed on Jun. 13, 2006.
Check, Erika, "Genetic expression speaks as loudly as gene type", bearing a date of Jan. 7, 2007, pp. 1-2, nature.com; located at: http://www.nature.com/news/2007/070101/pf/070101-8_pf.html, printed on Jan. 9, 2007.
Chiacchierini, Richard P., "Clinical Trials—Biostatistics and the Analysis of Clinical Data"; bearing a date of 2005; pp. 1-8; Medical Device Link; located at http://devicelink.com/grabber.php3?URL=http://devicelink.com; printed on Aug. 3, 2006.
Cook, David I., et al., "Subgroup Analysis in Clinical Trials"; Medical Journal of Australia; bearing dates of Feb. 9, 2004 and 2004; pp. 289-291 (pp. 1-9 from website); vol. 180, No. 6; located at http://www.mja.com.au/public/issues/180_06_150304/coo10086_fm.html; printed on Jul. 20, 2006
Cookson, William O.C., "Genetics and Genomics of Chronic Obstructive Pulmonary Disease", Proc Am Thorac Soc, bearing dates of Mar. 16, 2006, Mar. 20, 2006, and Apr. 13, 2006, pp. 473-477, vol. 3.
Couzin, Jennifer, "Human Genetics: In Asians and Whites, Gene Expression Varies by Race", Science, bearing a date of Jan. 12, 2007, pp. 173-174 (abstract pp. 1-3: p. 3 intentionally omitted), vol. 315, No. 5809, located at http://www.sciencemag.org/cgi/content/full/315/5809/173a, printed on Jan. 15, 2007.
D'Ambrosio, Claudio, et al.; "The future of microarray technology: networking the genome search"; Allergy; bearing dates of 2005, and Apr. 20, 2005; pp. 1219-1226; vol. 60; Blackwell Munksgaard.
Dearman, Rebecca J., et al., "Chemical Allergy: Considerations for the Practical Application of Cytokine Profiling", Toxicological Sciences, bearing dates of Sep. 4, 2002, Nov. 11, 2002 and 2003, pp. 137-145, vol. 71, the Society of Toxicology.
Dreifus, Claudia, "A Conversation with Mary V. Relling: Saving Lives with Tailor-Made Medication"; bearing a date of Aug. 29, 2006; pp. 1-3; New York Times; located at http://www.nytimes.com/2006/08/29/health/29conv.html?pagewant, printed on Aug. 29, 2006.
Eder, W., et al.; "Association between exposure to farming, allergies and genetic variation in CARD4/NOD1"; Allergy, bearing a date of Sep. 2006; pp. 1117-1124; vol. 61; Issue 9; Blackwell Synergy.
Eismann, U, et al.; "Pemetrexed: mRNA expression of the target genes TS, GARFT and DHFR correlates with the in vitro chemosensitivity of human solid tumors"; Int J Clin Pharmacol Ther.; bearing a date of Dec. 2005; pp. 567-569 (abstract p. 1); vol. 43, No. 12; PubMed; located at http://www.ncbi.nlm.nih.gov/entrez/query.fcgi?db=pubmed&cmd=R; printed on Jul. 31, 2006.
"EU project develops allergy database"; CORDIS; bearing a date of Sep. 14, 2006; p. 1; located at http://cordis.europa.eu/fetch?CALLER=EN_NEWS&ACTION=D; printed on Feb. 16, 2007.
Faux, J.A., et al., "Sensitivity to bee and wasp venoms: association with specific IgE responses to the bee and wasp venom and HLA DRB1 and DPB-1", Clinical & Experimental Allergy, bearing a date of May 1997, pp. 578-583 (abstract pp. 1-2), vol. 27, No. 5, Blackwell Publishing.
Frederickson, Robert M., "Lab Automation & Robotics: Sample management instrumentation and software in the high-throughput laboratory", Cambridge Healthtech Institute, bearing a date of Oct. 26, 2006, pp. 1-4, Bio-IT World, Inc., Needham, MA.
Gheuens, Jan; Edwards, Carl; "Pharmocagenomics and Pharmaceutical Research, Development and Therapy"; "Pharmacogenomics and Molecular Medicine in Application to Rheumatoid Arthritis"; bearing the dates of Feb. 12, 2001 and Feb. 13, 2001; pp. 1-4; National Institute of Statistical Sciences, located at http://www.niss.org/affiliates/genworkshop200102/abstracts.html; printed on Jul. 20, 2006.
"Guidance for Industry: Pharmocogenomic Data Submissions"; bearing a date of Mar. 31, 2005; pp. 1-22; U.S. Food & Drug Administration; located at http://www.fda.gov/CbER/gdlns/pharmdtasub.htm, printed on Jul. 20, 2006.
Hanauske, Axel-R., et al., "Pemetrexed Disodium: A Novel Antifolate Clinically Active Against Multiple Solid Tumors", The Oncologist, bearing dates of Jan. 15, 2001 and May 22, 2001; pp. 363-373; vol. 6.
Harle, D.G., et al., "Detection of thiopentone-reactive IgE antibodies following anaphylactoid reactions during anaesthesia", Clin Allergy, bearing a date of Sep. 1986, pp. 493-498; vol. 16, No. 5.
"HelixTree® Genetics Analysis Software for Mac OS X"; bearing dates of 2001 and 2006; pp. 1-16; Golden Helix; located at http://www.goldenhelix.com/HelixTree_MacOSX_details.html, printed on Sep. 19, 2006.
Immervoll, Thomas and Wjst, Matthias; "Current status of the Asthma and Allergy Database"; Nucleic Acids Research, bearing a date of 1999, pp. 213-214; vol. 27, No. 1; Oxford University Press.
Ivanciuc, Ovidiu, et al.; "Data mining of sequences and 3D structures of allergenic proteins"; Bioinformatics; bearing dates of Jan. 17, 2002; Mar. 26, 2002; and Apr. 28, 2002; pp. 1358-1364; vol. 18; No. 10.

(56) References Cited

OTHER PUBLICATIONS

John, W., et al., "Activity of multitargeted antifolate (pemetrexed disodium, LY231514) in patients with advanced colorectal carcinoma: results from a phase II study", Cancer; bearing a date of Apr. 15, 2000; pp. 1807-1813; (abstract p. 1) vol. 88; No. 8; PubMed; located at http://www.ncbi.nlm.nih.gov/entrez/query.fcgi?db=pubmed&cmd=R, printed on Jul. 31, 2006.

Johnson, Carolyn; "Should Medicine Be Colorblind?"; bearing a date of Aug. 24, 2004; pp. 1-2; The Boston Globe; located at http://222.boston.com/news/globe/health_science/articles/2004/08; printed on Jun. 7, 2006.

"Journal of Allergy and Clinical Immunology Says Peanut Allergy May Have Genetic Link", bearing a date of Jul. 17, 2000, pp. 1-2, PR Newswire.

Kalayci, O., et al.; "ALOX5 promoter genotype, asthma severity and $LTC_4$ production by eosinophils"; Allergy; bearing dates of Aug. 2, 2005 and 2006; pp. 97-103; vol. 61; Blackwell Munksgaard.

Kim, Jeong Joong PhD; et al.; "Chemokine RANTES Promoter Polymorphisms in Allergic Rhinitis"; The Laryngoscope; bearing a date of Apr. 2004; pp. 666-669; vol. 114; Issue 4.

Kjellman, N.I., et al., "Cord blood IgE determination for allergy prediction—a follow-up to seven years of age in 1651 children", Annals of Allergy, bearing a date of Aug. 1984, pp. 167-171; vol. 53, No. 2.

Lai, EC, "Micro RNAs are complementary to 3' UTR sequence motifs that mediate negative post-transcriptional regulation"; Nat Genet.; bearing a date of Apr. 2002; pp. 363-364 (abstract p. 1); vol. 30, No. 4; PubMed; located at http://www.ncbi.nlm.nih.gov/entrez/query.fcgi?db=pubmed&cmd=Retrieve&db=; printed on Aug. 14, 2006.

Latz, J. E., et al., "A semimechanistic-physiologic population pharmacokinetic/pharmacodynamic model for neutropenia following pemetrexed therapy", Cancer Chemother Pharmacol., bearing a date of Apr. 2006; pp. 412-426; vol. 57; No. 4; (Abstract bearing a date of Dec. 2, 2005, pp. 1-2); located at http://www.ncbi.nlm.nih.gov/entrez/querv.fcgi?db=pubmed&cmd=R; printed on Jul. 31, 2006.

Latz, J. E., et al., "A semimechanistic-physiologic population pharmacokinetic/pharmacodynamic model for neutropenia following pemetrexed therapy", Cancer Chemother Pharmacol., bearing dates of Dec. 21, 2004, Apr. 17, 2005, Dec. 2, 2005 and Apr. 2006; pp. 412-426; vol. 57; No. 4; Springer-Verlag.

Latz, JE, et al.; "Clinical application of a semimechanistic-physiologic population PK/PD model for neutropenia following pemetrexed therapy"; Cancer Chemother Pharmacol.; bearing a date of Apr. 2006; pp. 427-435 (abstract p. 1); vol. 57, No. 4; PubMed; located at http://www.ncbi.nlmnih.gov/entrez/query.fcgi?db=pubmed&cmd=R; printed on Jul. 31, 2006.

Latz, J. E. et al, "Population pharmacokinetic analysis of ten phase II clinical trials of pemetrexed in cancer patients", Cancer Chemother Pharmacol., bearing a date of Apr. 2006; pp. 401-411; vol. 57; No. 4; (Abstract bearing a date of Dec. 2, 2005, pp. 1-2); located at http://www.ncbi.nlm.nih.gov/entrez/query.fcgi?db=pubmed&cmd=R; printed on Jul. 31, 2006.

Latz, Jane E. et al, "Population pharmacokinetic analysis of ten phase II clinical trials of pemetrexed in cancer patients", Cancer Chemother Pharmacol.; bearing dates of Dec. 22, 2004, Apr. 17, 2005, Dec. 2, 2005 and 2005; pp. 401-411; vol. 57; Springer-Verlag.

Levine, Bruce L., et al., "Gene transfer in humans using a conditionally replicating lentiviral vector", Proceedings of the National Academy of Sciences of the United States of America (PNAS), bearing a date of Nov. 14, 2006, pp. 17372-17377, vol. 103, No. 46, located at www.pnas.org/cgi/doi/10.1073/pnas.0608138103.

"List of Allergens"; bearing a date of Feb. 20, 2007; located at http://www.allergen.org/Allergen.aspx.

Manegold, C., et al.; "Front-line treatment of advanced non-small-cell lung cancer with MTA (LY231514, pemetrexed disodium, ALIMTA) and cisplatin: a multicenter phase II trial"; Ann Oncol; bearing a date of Apr. 2000; pp. 435-440 (abstract p. 1); vol. 11, No. 4; PubMed located at http://222.ncbi.nlm.nih.gov/entrez/query.fcgi?db=pubmed&cmd=R; printed on Jul. 31, 2006.

"Markers of Gene, Protein, or Micro-RNA Activity Predict Outcome in Prostate and Colorectal Cancers"; bearing a date of Apr. 8, 2006; pp. 1-3; Science Daily; located at http://sciencedaily.com/releases/2006/04/060407143815.htm; printed on Aug. 14, 2006.

Mazieres J; "Wnt2 as a new therapeutic target in malignant pleural mesothelioma"; Int J Cancer, bearing a date of Nov. 1, 2005; pp. 326-332 (abstract p. 1); vol. 117, No. 2; PubMed; located at http://www.ncbi.nlm.nih.gov/entrez/query.fcgi?db=pubmed&cmd=R; printed on Jul. 31, 2006.

McDonald, AC, et al.; "A phase I and pharmacokinetic study of LY231514, the multitargeted antifolate"; Clin Cancer Res.; bearing a date of Mar. 1998; pp. 605-610 (abstract p. 1) vol. 4; No. 3; PubMed; located at http://www.ncbi.nlm.nih.gov/entrez/query.fcgi?db=pubmed&cmd=R; printed on Jul. 31, 2006.

McDowell, Sarah E., et al.; "Systematic review and meta-analysis of ethnic differences in risks of adverse reactions to drugs used in cardiovascular medicine"; bearing dates of 2001-2006; (abstract p. 1); PharmGKB; located at http://www.pharmgkb.org/do/serve?objld=PA144559843 printed on Aug. 18, 2006.

McDowell, Sarah E., et al.; "Systematic review and meta-analysis of ethnic differences in risks of adverse reactions to drugs in cardiovascular medicine"; bearing dates of Feb. 23, 2006, May 20, 2006 and May 5, 2006; pp. 1177-1181 (pp. 1-14 from website); located at http://bmj.bmjjournals.com/cgi/content/full/332/7551/1177; printed on Aug. 22, 2006.

Minematsu, N. et al., "Limitation of cigarette consumption by CYP2A6*4, *7 and *9 polymorphisms", Eur Respir Journal, 2006; pp. 289-292 (abstract p. 1); vol. 27; ERS Journals Ltd.; printed on Jun. 19, 2006.

Moffatt, Miriam F., et al., "Atopy, respiratory function and HLA-DR in Aboriginal Australians", Human Molecular Genetics, bearing dates of Nov. 4, 2002 and Jan. 9, 2003, pp. 625-630, vol. 12, No. 6, Oxford University Press.

Moore, W.C., et al.; "Characterization of the severe asthma phenotype by the National Heart, Lung and Blood Institute's Severe Asthma Research Program"; J Allergy Clin Immunol.; bearing a date of Feb. 2007; pp. 405-413; vol. 119; No. 2.

Nainggolan, Lisa, First genetically targeted drug for heart disease?, bearing a date of Jul. 11, 2006; pp. 1-4.

"New Data on Lung Cancer Trials with Targetn® is Presented at ASCO"; bearing a date of Jun. 5, 2006; pp. 1-3; Ligand Pharmaceutical Incorporated.

Nicholson, Jeremy K., "Global systems biology, personalized medicine and molecular epidemiology", Molecular Systems Biology, bearing a date of Oct. 3, 2006, Article Number: 52, pp. 1-6, EMBO & Nature Publishing Group.

Niyikiza, Clet, et al.; "Homocysteine and Methylmalonic Acid: Markers to Predict and Avoid Toxicity from Pemetrexed Therapy"; Mol Cancer Ther., bearing a date of May 2002, pp. 545-552 (abstract p. 1); vol. 1, PubMed; located at http://www.ncbi.nlm.nih.gov/entrez/query.fcgi?db=pubmed&cmd=R; printed on Jul. 31, 2006.

Niyikiza, Clet, et al.; "Homocysteine and Methylmalonic Acid: Markers to Predict and Avoid Toxicity from Pemetrexed Therapy"; Molecular Cancer Therapeutics, May 2002, pp. 545-552; vol. 1.

O'Dwyer, P. J., et al., "Overview of phase II trails of MTA in solid tumors", Semin Oncol., bearing a date Apr. 1999; pp. 99-104; (abstract p. 1) vol. 26; No. 2; Suppl 6; PubMed; located at http://www.ncbi.nlm.nih.gov/entrez/query.fcgi?db=pubmed&cmd=R, printed on Jul. 31, 2006.

O'Kane, Dennis J. et al., "Pharmacogenomics and Reducing the Frequency of Adverse Drug Events", Pharmacogenomics, bearing a date of 2003, pp. 1-4; vol. 4, No. 1; Ashley Publications Ltd.

Ono, S.J., "Molecular genetics of allergic diseases", Annu Rev Immunol, bearing a date of 2000, pp. 347-366; vol. 18.

Otey, Matthew E., et al., "Dissimilarity Measures for Detecting Hepatotoxicity in Clinical Trial Data", 2006 SIAM Conference on Data Mining, bearing dates of Apr. 20, 2006 and Apr. 22, 2006; pp. 1-7; located at http://www.siam.org/meetings/sdm06/proceedings/05oteym.pdf., printed on Jul. 20, 2006.

Ouellet, D., et al.; "Population pharmacokinetics of pemetrexed disodium (ALIMTA) I in patients with cancer"; Cancer Chemother Pharmacol.; bearing a date of 2000, pp. 227-234 (abstract p. 1); vol.

(56) References Cited

OTHER PUBLICATIONS

46, No. 3; PubMed; located at http://www.ncbi.nlm.nih.gov/entrez/query.fcgi?db=pubmed&cmd=R; printed on Jul. 31, 2006.
"Pharmacogenetics as a Predictor of Toxicity in Pre-Menopausal Women Receiving Doxorubicin and Cyclophosphamide in Early Breast Cancer", bearing dates of Jan. 2006 and Jul. 13, 2006; pp. 1-3; Clinical Trials.gov, located at http://www.clinicaltrials.gov/ct/show/NCT00352872:jsessionid=F1; printed on Aug. 17, 2006.
Raloff, J., "Peanut allergy found common and increasing", Science News, bearing a date of Sep. 7, 1996, vol. 150, No. 10, p. 150; Science Service.
Rieger-Ziegler, Verena, et al., "Hymenoptera Venom Allergy: Time Course of Specific IgE Concentrations during the first Weeks after a Sting", International Archives of Allergy and Immunology, bearing dates of 1999, Nov. 19, 1998, Jun. 23, 1999, and 2006, pp. 166-168, vol. 120.
Rogatko, A. et al., "Patient characteristics compete with dose as predictors of acute treatment toxicity in early phase clinical trials", Clinical Cancer Research, Jul. 15, 2004; pp. 4645-4651 (pp. 1-14 from website); vol. 10; American Association of Cancer Research.
Rollins, KD, et al.; "Pemetrexed: a multitargeted antifolate"; Clin Ther.; bearing a date of Sep. 2005; pp. 1343-1382 (abstract pp. 1-2); vol. 27, No. 9, PubMed; located at http://www.ncbi.nlm.nih.gov/entrez/query.fcgi?db=pubmed&cmd=R; printed on Jul. 31, 2006.
Rufo, Paul A. MD, MMSC, "Study to Identify Non-Invasive Markers of Gastrointestinal Allergy", ClinicalTrials.gov, bearing a date of Jan. 4, 2006, pp. 1-4, located at http://www.clinicaltrials.gov/ct/gui/show/NCT00272818, printed on Jan. 24, 2007.
Salamone, Salvatore, "Pfizer Data Mining Focuses on Clinical Trials"; bearing a date of Feb. 23, 2006; pp. 1-2; Bio-IT World.
Scagliotti, GV;; et al.; "Phase II study of pemetrexed with and without folic acid and vitamin B 12 as front-line therapy in malignant pleural mesothelioma"; J Clin Oncol.; bearing a date of Apr. 15, 2003; pp. 1556-1561; (abstract p. 1); vol. 21, No. 8; PubMed; located at http://www.ncbi.nlm.nih.gov/entrez/query.fcgi?db=pubmed&cmd=R; printed on Jul. 31, 2006.
Sharp, Linda; Little, Julian; "Polymorphisms in Genes Involved in Folate Metabolism and Colorectal Neoplasia: A HuGE Review"; bearing a date of Mar. 1, 2004; pp. 1-13; National Office of Public Health Genomics; located at http://www.cdc.gov/genomics/hugenet/reviews/neoplasia.htm#refer; printed on Aug. 1, 2006.
Sheikh, Aziz, MRCP, MRCGP, "Itch, sneeze and wheeze: the genetics of atopic allergy", Journal of the Royal Society of Medicine, bearing a date of Jan. 2002, pp. 14-17, vol. 95, London, England.
Sicherer, Scott H., MD, "Determinants of systemic manifestations of food allergy", J Allergy Clin Immunol, bearing a date of 2000, pp. S251-S257, vol. 106, No. 5, Mosby, Inc.
Sigmond, J., et al.; "Induction of resistance to the multitargeted antifolate Pemetrexed (ALIMTA) in WiDr human colon cancer cells is associated with thymidylate synthase overexpression"; Biochem Pharmacol; bearing a date of Aug. 1, 2003; pp. 431-438 (abstract p. 1); vol. 66, No. 3; PubMed; located at http://www.ncbi.nlm.nih.gov/entrez/query.fcgi?db=pubmed&cmd=R; printed on Jul. 31, 2006.
Spielman, Richard S., et al.; "Common genetic variants account for differences in gene expression among ethnic groups"; Nature Genetics; bearing a date of Jan. 7, 2007; pp. 226-231; vol. 39.
Szalai, Csaba Ph.D, et al., "Polymorphism in the gene regulatory region of MCP-1 is associated with asthma susceptibility and severity"; J Allergy Clin Immunol.; bearing a date of Sep. 2001; pp. 375-381; vol. 108; Issue 3.
Tarkan, Laurie, "In Testing for Allergies, a Single Shot May Suffice"; The New York Times, bearing a date of Mar. 20, 2007; pp. 1-3; New York, NY.
"Technique Offers New View of Dynamic Biological Landscape"; bearing a date of Nov. 4, 2005; pp. 1-3; Howard Hughes Medical Institute.
Vandebriel, R.J., "Gene polymorphisms within the immune system that may underlie drug allergy", Naunyn Schmiedebergs Arch Pharmacol, bearing dates of Oct. 3, 2003 and Jan. 2004, pp. 125-132, vol. 369, No. 1, printed on Jan. 29, 2007.
Van Noorden, Richard; "Another source of genetic variability mapped: Researchers chart out insertions and deletions in the genome"; pp. 1-2; bearing a date of Aug. 10, 2006; news@nature.com; located at http://www.nature.com/news/2006/060807/pf/060807-15_pf.html; printed on Aug. 11, 2006.
Vennekens, Rudi, et al.; "Increased IgE-dependent mast cell activation and anaphylactic responses in mice lacking the calcium-activated nonselective cation channel $TRPM_4$"; Nature Immunology; bearing a date of Feb. 11, 2007, pp. 312-320; vol. 8.
Vercelli, Donata, MD; "The functional genomics of CD14 and its role in IgE responses: An integrated view"; Journal of Allergy and Clinical Immunology; bearing a date of Jan. 2002; pp. 14-21; vol. 109; Issue 1.
Vogelzang, Nicholas J., et al., "Phase III Study of Pemetrexed in Combination with Cisplatin Verus Cisplatin Alone in Patients with Malignant Pleural Mesothelioma"; Journal of Clinical Oncology, bearing a date of Jul. 15, 2003; pp. 2636-2644; vol. 21, No. 14; American Society of Clinical Oncology; printed on Aug. 1, 2006.
Werner, M., et al.; "Asthma is associated with single-nucleotide polymorphisms in ADAM33"; Clinical & Experimental Allergy; bearing a date of Jan. 2004; pp. 26-31; vol. 34, Issue 1; Blackwell Synergy.
Wilson, James F., et al., "Population Genetic Structure of Variable Drug Response", Nature Genetics, bearing a date of Oct. 29, 2001; pp. 265-269; vol. 29; Nature Publishing Group; located at www.nature.com/ng/journal/v29/n3/full/ng761.html, printed on Aug. 18, 2006.
Wjst, Matthias and Immervoll, Thomas; "An Internet linkage and mutation database for the complex phenotype asthma"; Bioinformatics; bearing a date of Oct. 1998; pp. 827-828; vol. 14; No. 9.
Worzalla, J. F., Schultz, RM; "Role of folic acid in modulating the toxicity and efficacy of the multitargeted antifolate, LY231514", Anticancer Res., bearing dates of Sep.-Oct. 1998; pp. 3235-3239; (abstract p. 1) vol. 18; No. 5A; PubMed; located at http://www.ncbi.nlm.nih.gov/entrez/query.fcgi?db=pubmed&cmd=R.; printed on Jul. 31, 2006.
Xu, CF, et al.; "Identification of a pharmacogenetic effect by linkage disequilibrium mapping"; p. 1; PharmGkb; located at http://www.pharmgkb.org/do/seve?objId=PA131906668&objCls=; printed on Aug. 18, 2006.
Yang, Jing, et al., "HLA-DRB genotype and specific IgE responses in patients with allergies to penicillins", Chin, Med J, bearing dates of Aug. 26, 2005 and 2006, pp. 458-466, vol. 119, No. 6.
Zhao, R., et al.; "Loss of reduced folate carrier function and folate depletion result in enhanced pemetrexed inhibition of purine synthesis"; Clin Cancer Res.; bearing a date of Feb. 1, 2005; pp. 1294-1301 (abstract p. 1); vol. 11, No. 3; located at http://www.ncbi.nlm.nih.gov/entrez/query.fcgi?db=pubmed&cmd=R; printed on Jul. 31, 2006.
Ziegler, V., et al., "INPRET—database on predictive tests (allergy)"; Seminars in Dermatology.; bearing a date of Jun. 1989; pp. 80-82; vol. 8, No. 2.
U.S. Appl. No. 11/893,612, Jung et al.
U.S. Appl. No. 11/893,370, Jung et al.
U.S. Appl. No. 11/893,106, Jung et al.
U.S. Appl. No. 11/891,669, Jung et al.
U.S. Appl. No. 11/881,803, Jung et al.
U.S. Appl. No. 11/881,802, Jung et al.
U.S. Appl. No. 11/821,105, Jung et al.
U.S. Appl. No. 11/810,358, Jung et al.
U.S. Appl. No. 11/809,776, Jung et al.
U.S. Appl. No. 11/728,311, Jung et al.
U.S. Appl. No. 11/728,026, Jung et al.
U.S. Appl. No. 11/728,025, Jung et al.
U.S. Appl. No. 11/647,531, Jung et al.
U.S. Appl. No. 11/541,478, Jung et al.
Dehais, Patrice et al.; "An Interactive System for Database in Immunogenetics"; Proceedings of the Twenty-Seventh Annual Hawaii International Conference on System Sciences; Jan. 4-7, 1994; pp. 25-34; vol. 5; IEEE; Maui, Hawaii.

(56) References Cited

OTHER PUBLICATIONS

"Discovery, Reality and Hope: A Brief History of Alimta®"; Answers That Matter; Eli Lilly and Company; printed on Nov. 30, 2010; pp. 1-4.

Pochon, Philip et al.; "Warehousing Clinical Pharmacogenomics Data"; printed on Nov. 30, 2010; pp. 1-5; SAS Institute Inc., Cary, NC.

Sicherer, Scott H.; "Food allergy"; The Lancet; bearing a date of Aug. 31, 2002; pp. 701-710; vol. 360;The Lancet Publishing Group.

Blumenthal et al.; "A genome-wide search for allergic response (atopy) genes in three ethnic groups: Collaborative Study on the Genetics of Asthma"; Human Genetics; bearing a date of Oct. 25, 2003; pp. 157-164; vol. 114; Springer-Verlag.

Qiao et al.; "Specific Serum IgE Levels and FcεRIβ Genetic Polymorphism in Patients with Penicillins Allergy"; Allergy; accepted for publication Mar. 31, 2004; pp. 1326-1332; vol. 59; Blackwell Munksgaard.

Tomita et al.; "Artificial neural network approach for selection of susceptible single nucleotide polymorphisms and construction of prediction model on childhood allergic asthma"; BMC Bioinformatics; Sep. 1, 2004; pp. 1-13; vol. 5, Issue 120; BioMed Central Ltd.

Hansen et al.; "The Variability of Individual Tolerance to Methotrexate in Cancer Patients"; Mar. 26, 1971; pp. 298-305; vol. 2; British Journal of Cancer.

FIG. 5

| | 306 Study Efficacy Data | 308 Study Adverse Event Data | 310 Subset Efficacy Data | 312 Subset Adverse Event Data | 314 Subpopulation Identifier Data |
|---|---|---|---|---|---|
| Pemetrexed (Alimta®) | Acceptable efficacy | Odds ratio of developing severe toxicity = 1 | Efficacy maintained or improved | Methylmalonic acid levels < 119.0 nmol/l (Odds ratio of developing severe toxicity = 0.3) | Supplementation with folic acid and vitamin B12 to decrease methylmalonic acid levels |
| Pemetrexed (Alimta®) | Acceptable efficacy | Odds ratio of developing severe toxicity = 1 | Efficacy maintained or improved | Total homocysteine levels < 7.5 µmol/l (Odds ratio of developing severe toxicity = 0.7) | Supplementation with folic acid and/or vitamin B12 to decrease total homocysteine levels |

502 ↑ (first row)
504 ↑ (second row)

FIG. 6

| | 306 Study Efficacy Data | 308 Study Adverse Event Data | 310 Subset Efficacy Data | 312 Subset Adverse Event Data | 314 Subpopulation Identifier Data |
|---|---|---|---|---|---|
| Pemetrexed (Alimta®) 602 → | 41.3% partial response rate for Pemetrexed /Cisplatin vs. 16.7% for Cisplatin alone | 41.4% Grade 3/4 Neutropenia (partial and never supplemented group) | 45.6% partial response rate for Pemetrexed /Cisplatin vs. 19.0% for Cisplatin alone | 23.2% Grade 3/4 Neutropenia (full supplementation group) | Supplementation with folic acid and vitamin B12 |
| Pemetrexed (Alimta®) 604 → | 41.3% partial response rate for Pemetrexed /Cisplatin vs. 16.7% for Cisplatin alone | 31.3% Nausea (never supplemented group) | 45.6% partial response rate for Pemetrexed /Cisplatin vs. 19.0% for Cisplatin alone | 11.9% Nausea (full and partial supplementation group) | Supplementation with folic acid and vitamin B12 |
| Pemetrexed (Alimta®) 606 → | 41.3% partial response rate for Pemetrexed /Cisplatin vs. 16.7% for Cisplatin alone | 31.3% Vomiting (never supplemented group) | 45.6% partial response rate for Pemetrexed /Cisplatin vs. 19.0% for Cisplatin alone | 10.3% Vomiting (full and partial supplementation group) | Supplementation with folic acid and vitamin B12 |

FIG. 7

| | 306 Study Efficacy Data | 308 Study Adverse Event Data | 310 Subset Efficacy Data | 312 Subset Adverse Event Data | 314 Subpopulation Identifier Data |
|---|---|---|---|---|---|
| Ifosfamide | Acceptable efficacy | Darkened and thickened skin | Maintained efficacy | Little or no darkened and thickened skin in individuals with a specific CYP2B6 SNP profile | Increased activity of CYP2B6 in Hispanic females aged 20-45 |
| ACE Inhibitor | Acceptable efficacy | Angio-edema (Relative risk = 1) | Acceptable efficacy | Increased incidence of angio-edema in Black patients (Relative risk = 3) | Black patients of West Indian descent |

702 ↗ (Ifosfamide row)
704 ↗ (ACE Inhibitor row)

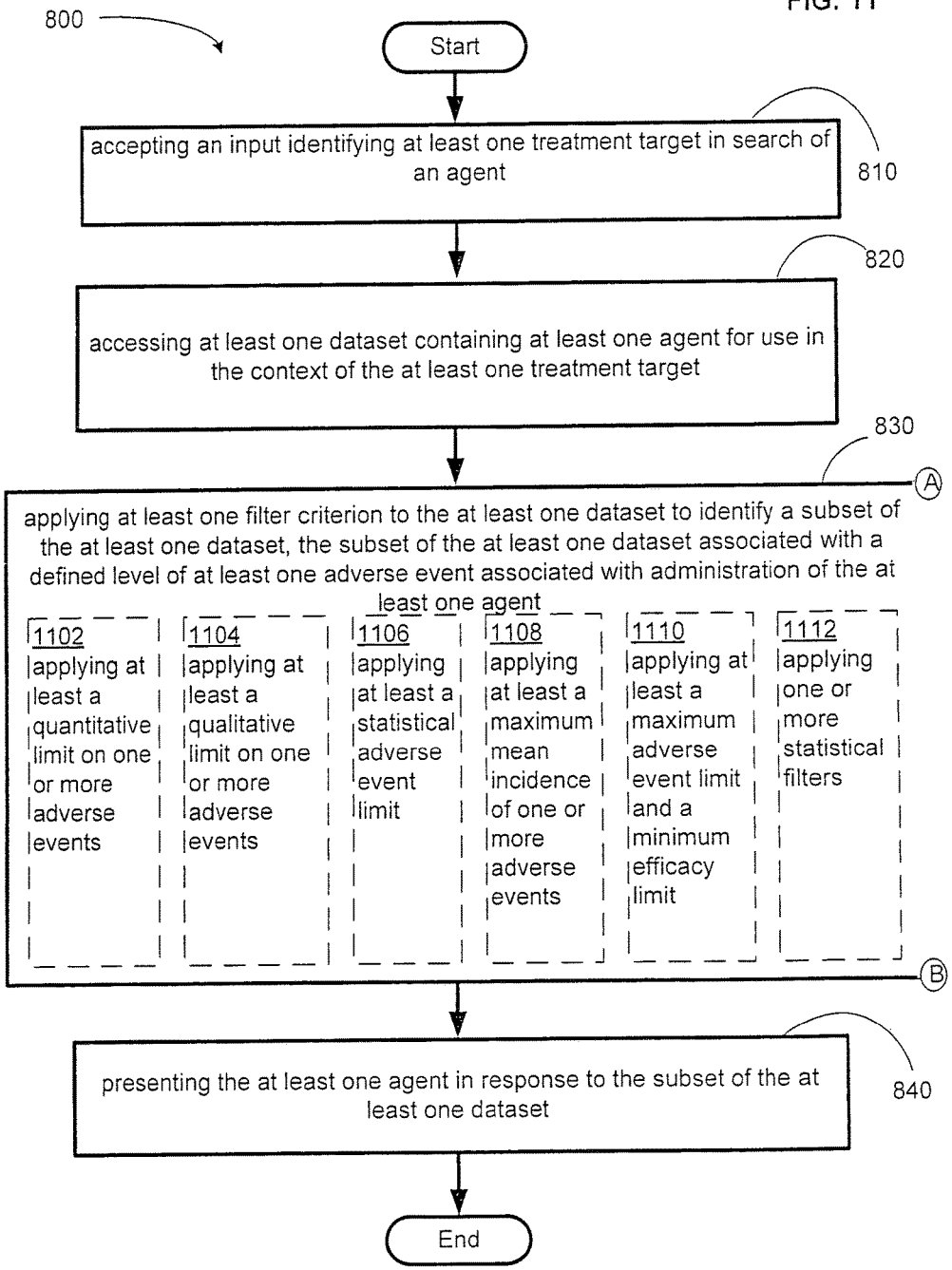

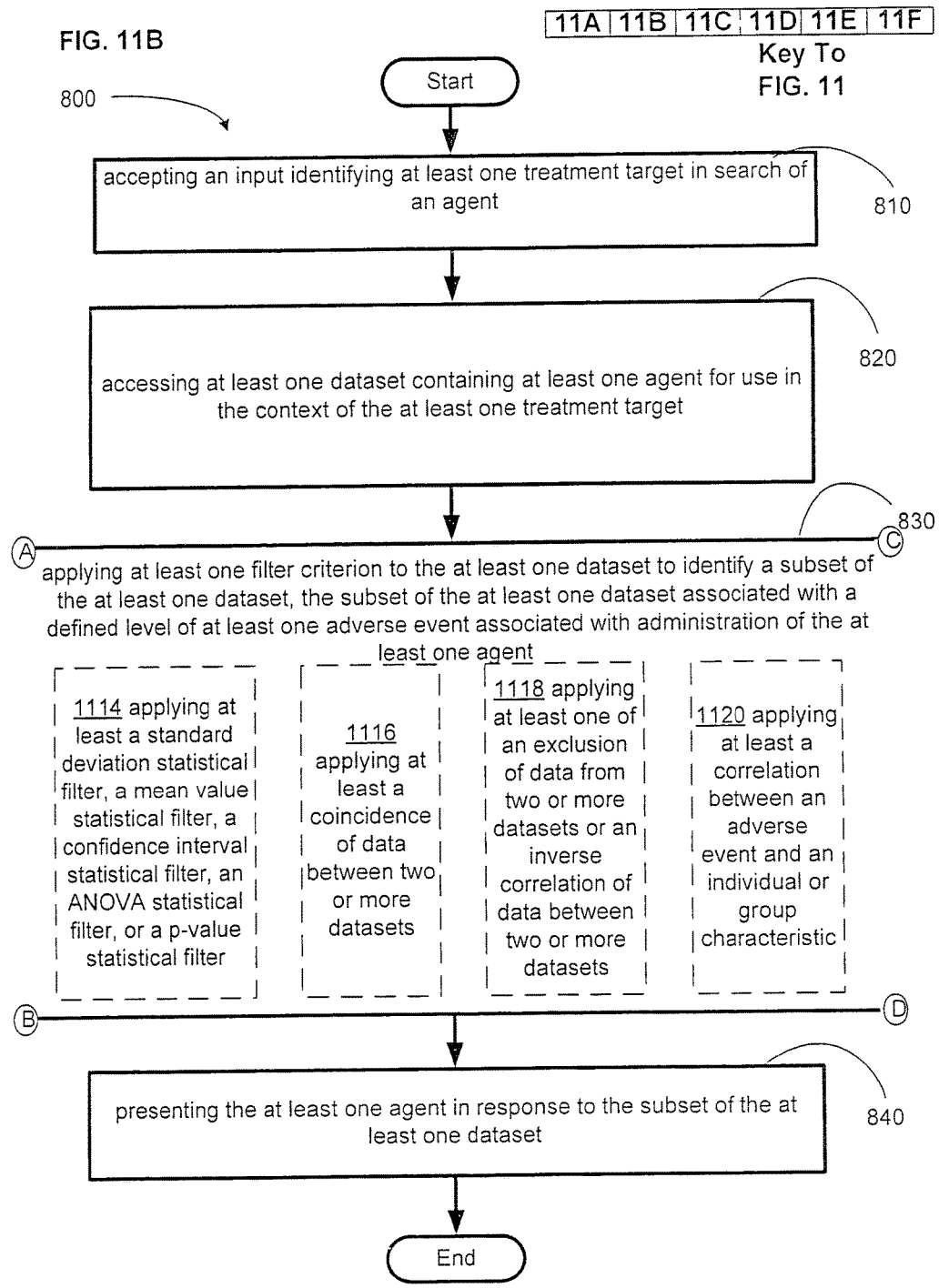

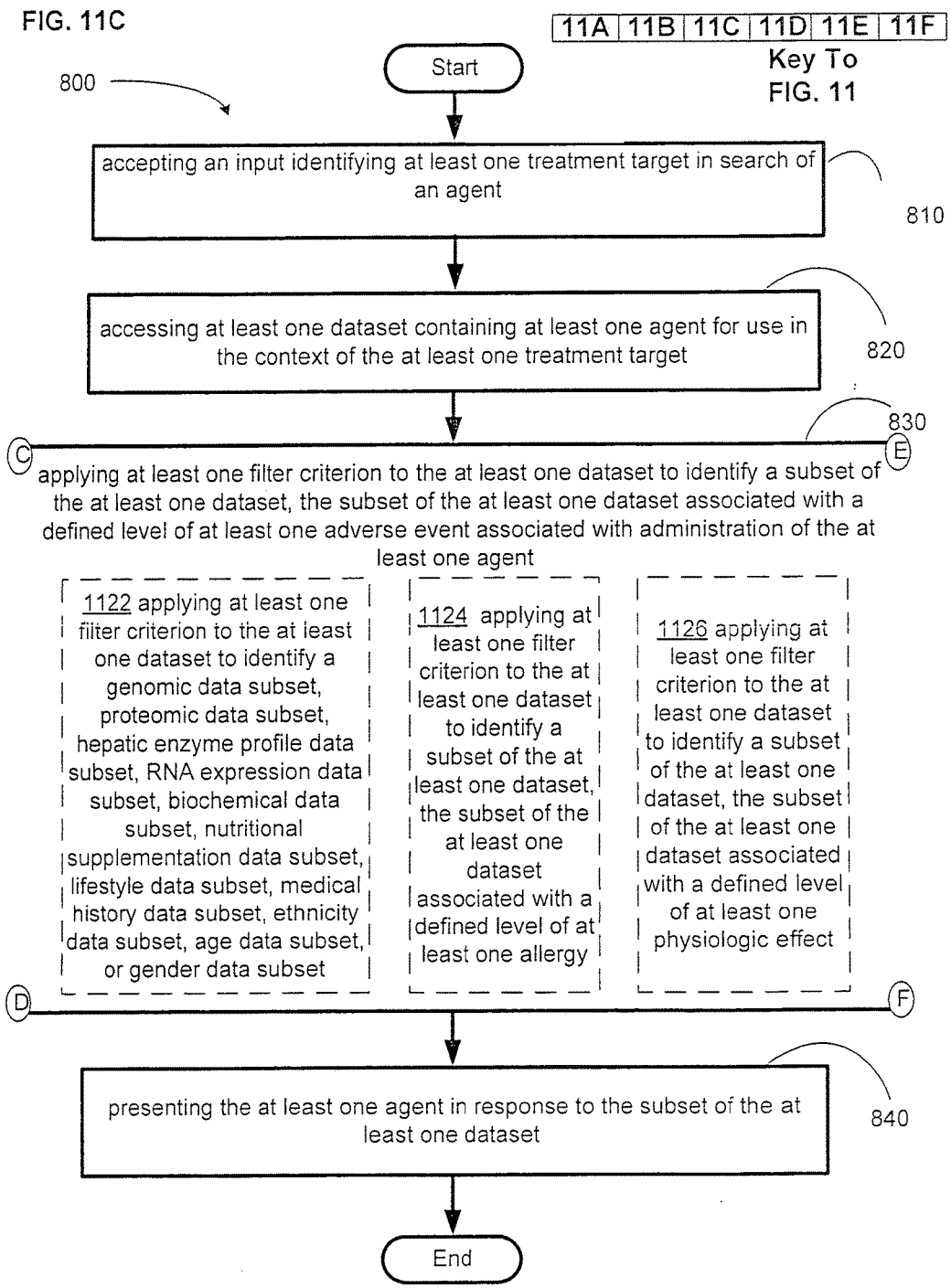

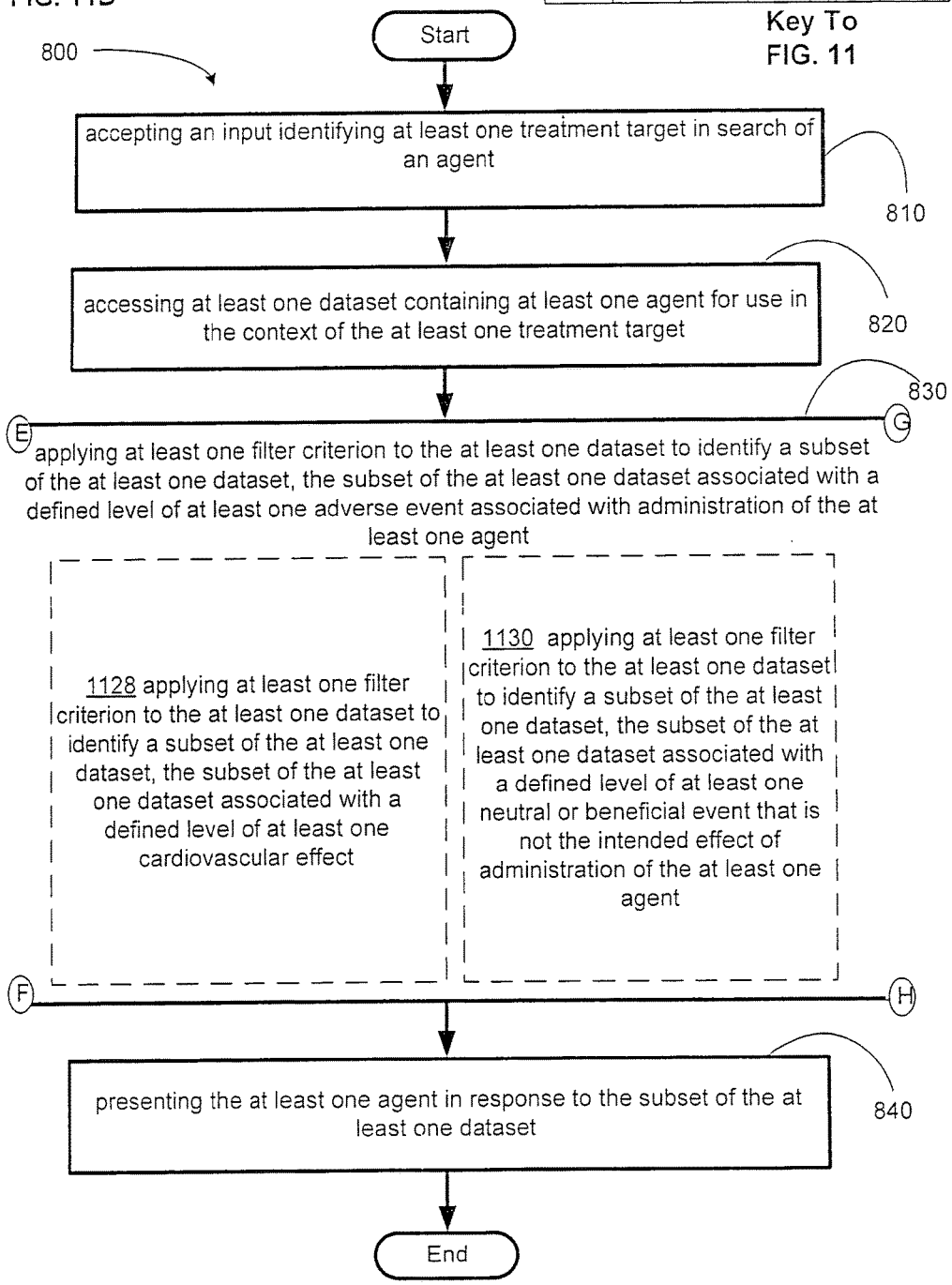

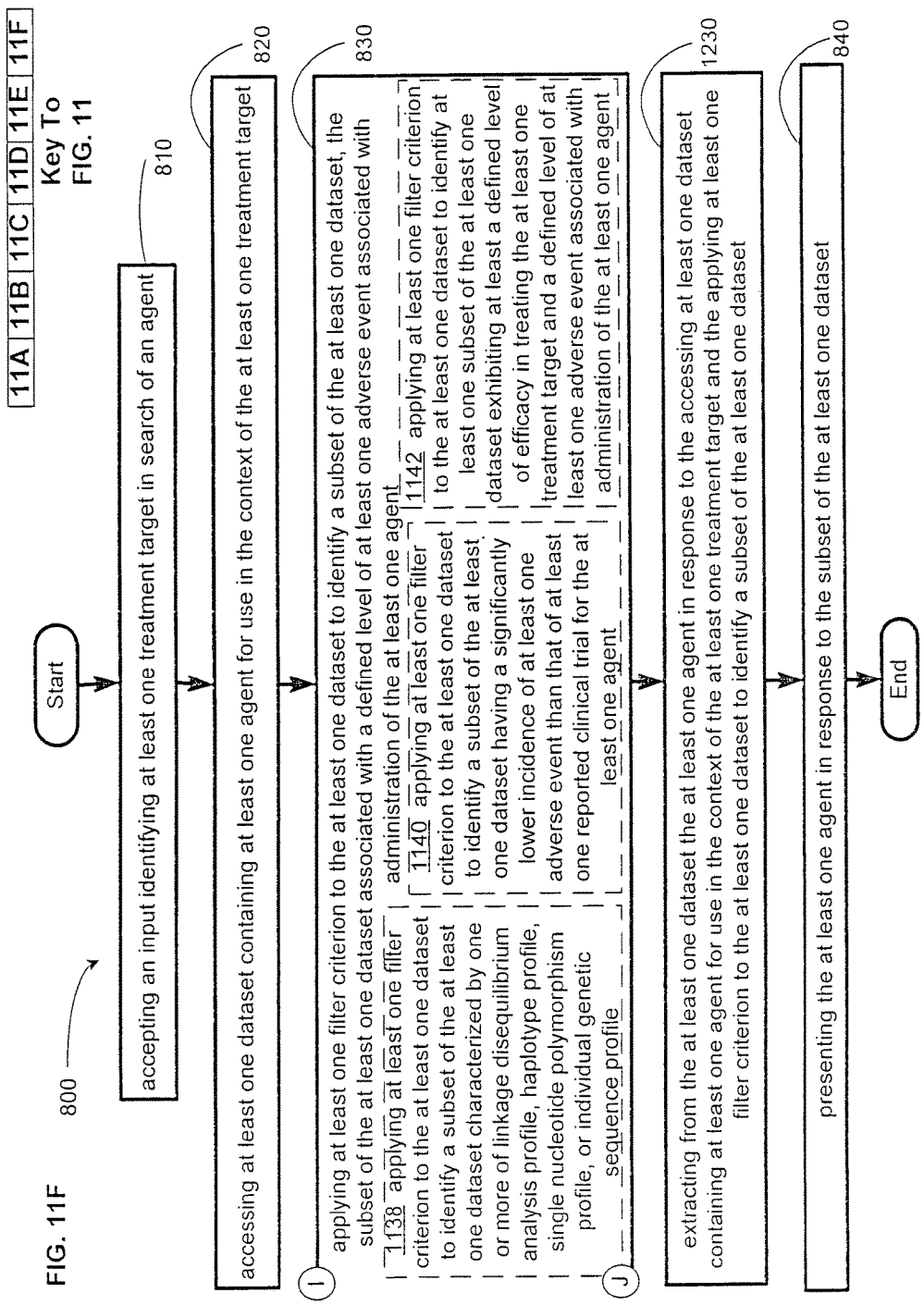

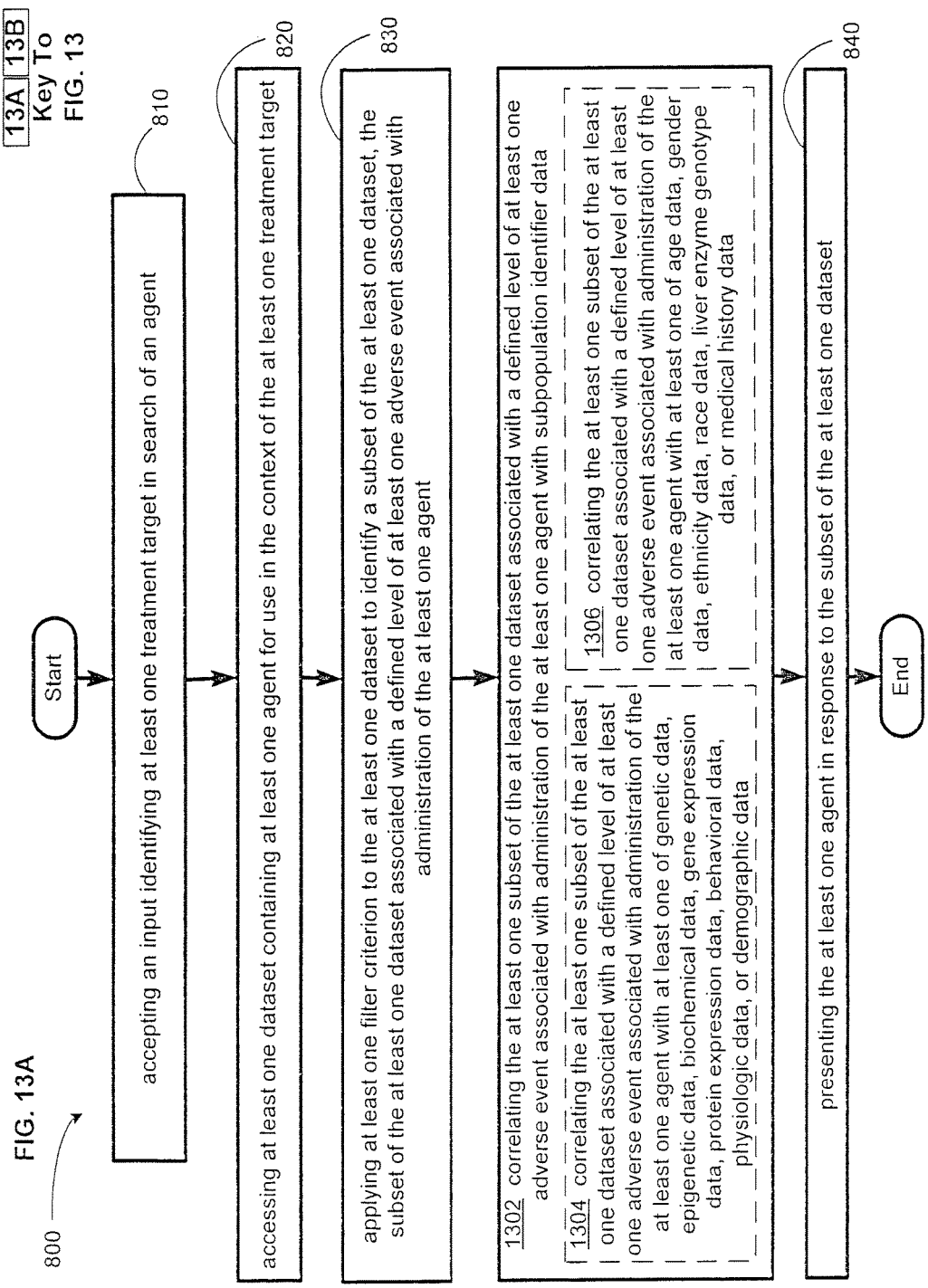

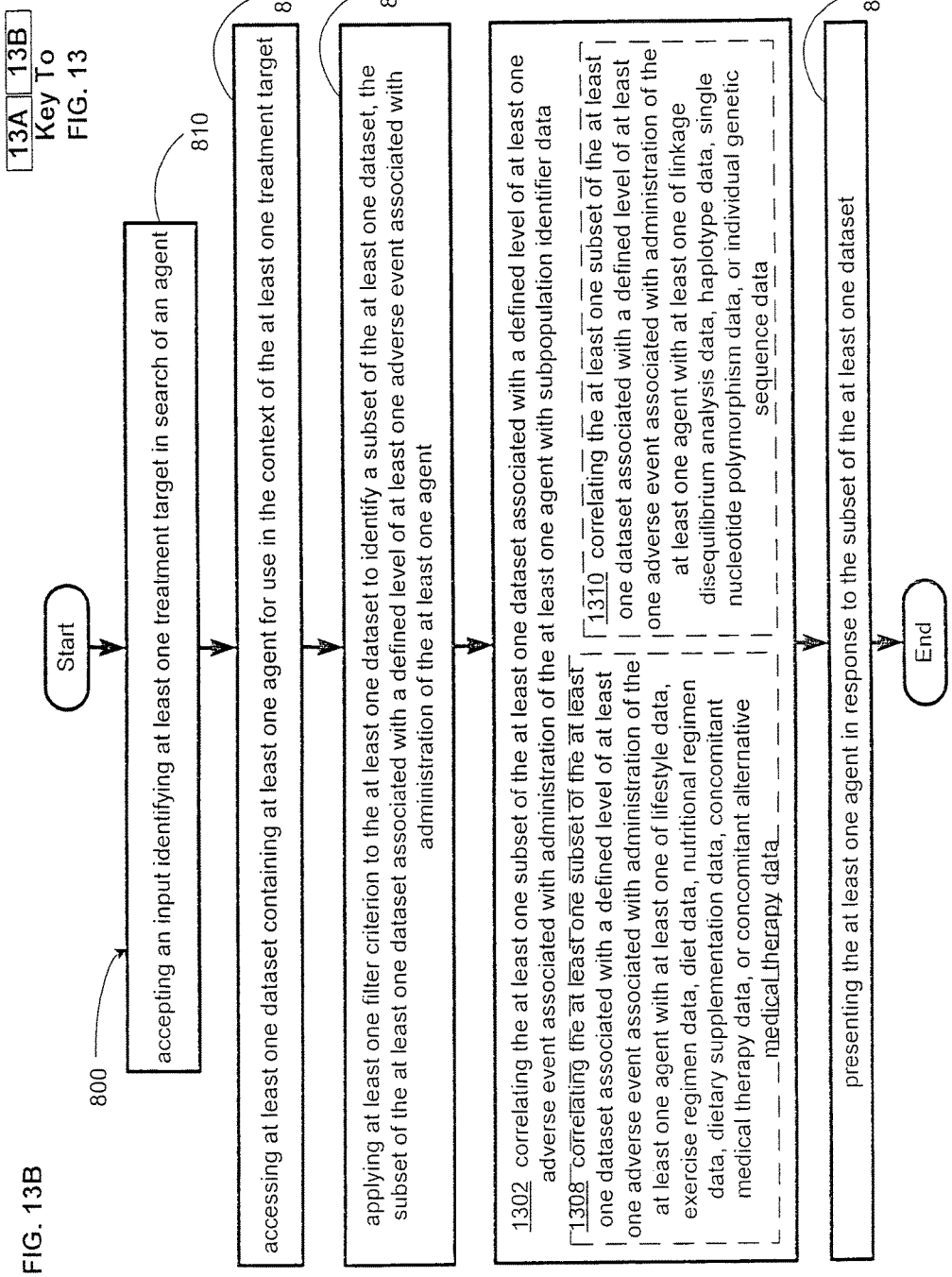

COMPUTATIONAL SYSTEMS FOR BIOMEDICAL DATA

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/541,478, entitled COMPUTATIONAL SYSTEMS FOR BIOMEDICAL DATA, naming Edward K. Y. Jung; Royce A. Levien; Robert W. Lord, Mark A. Malamud, and Lowell L. Wood, Jr. as inventors, filed 29 Sep. 2006 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/647,531, entitled COMPUTATIONAL SYSTEMS FOR BIOMEDICAL DATA, naming Edward K. Y. Jung; Royce A. Levien; Robert W. Lord, Mark A. Malamud, and Lowell L. Wood, Jr. as inventors, filed 27 Dec. 2006 which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to data handling techniques.

SUMMARY

An embodiment provides a method. In one implementation, the method includes but is not limited to accepting an input identifying at least one treatment target in search of an agent, accessing at least one dataset containing at least one agent for use in the context of the at least one treatment target, applying at least one filter criterion to the at least one dataset to identify a subset of the at least one dataset, the subset of the at least one dataset associated with a defined level of at least one adverse event associated with administration of the at least one agent, and presenting the at least one agent in response to the subset of the at least one dataset. In addition to the foregoing, other method aspects are described in the claims, drawings, and text forming a part of the present disclosure.

An embodiment provides a method. In one implementation, the method includes but is not limited to accepting an input identifying at least one treatment target in search of an agent, accessing at least one dataset containing at least one agent for use in the context of the at least one treatment target, applying at least one filter criterion to the at least one dataset to identify a subset of the at least one dataset, the subset of the at least one dataset associated with a defined level of at least one adverse event associated with administration of the at least one agent, extracting from the at least one dataset the at least one agent in response to the accessing at least one dataset containing at least one agent for use in the context of the at least one treatment target and the applying at least one filter criterion to the at least one dataset to identify a subset of the at least one dataset, and presenting the at least one agent in response to the subset of the at least one dataset. In addition to the foregoing, other method aspects are described in the claims, drawings, and text forming a part of the present disclosure.

An embodiment provides a method. In one implementation, the method includes but is not limited to accepting an input identifying at least one treatment target in search of an agent, accessing at least one dataset containing at least one agent for use in the context of the at least one treatment target, applying at least one filter criterion to the at least one dataset to identify a subset of the at least one dataset, the subset of the at least one dataset associated with a defined level of at least one adverse event associated with administration of the at least one agent, presenting the at least one agent in response to the subset of the at least one dataset, and correlating the at least one subset of the at least one dataset associated with a defined level of at least one adverse event associated with administration of the at least one agent with subpopulation identifier data. In addition to the foregoing, other method aspects are described in the claims, drawings, and text forming a part of the present disclosure.

An embodiment provides a method. In one implementation, the method includes but is not limited to accepting at least one treatment target in search of an agent at one or more user interfaces, and transmitting data from the one or more user interfaces to at least one data analysis system, the data including at least the treatment target in search of an agent, the data analysis system being capable of identifying at least one agent for use in the context of the at least one treatment target, the data analysis system further being capable of applying at least one filter criterion to the at least one dataset to identify a subset of the at least one dataset, the subset of the at least one dataset associated with a defined level of at least one adverse event associated with administration of the at least one agent, and the data analysis system further being capable of sending a signal to either the one or more user interfaces or a different user interface in response to the subset of the at least one dataset, which signal transmits the at least one agent. In addition to the foregoing, other method aspects are described in the claims, drawings, and text forming a part of the present disclosure.

An embodiment provides a system. In one implementation, the system includes but is not limited to means for accepting an input identifying at least one treatment target in search of an agent; means for accessing at least one dataset containing at least one agent for use in the context of the at least one treatment target; means for applying at least one filter criterion to the at least one dataset to identify a subset of the at least one dataset, the subset of the at least one dataset associated with a defined level of at least one adverse event associated with administration of the at least one agent; and means for presenting the at least one agent in response to the subset of the at least one dataset. In addition to the foregoing, other system aspects are described in the claims, drawings, and text forming a part of the present disclosure.

An embodiment provides a system. In one implementation, the system includes but is not limited to means for accepting an input identifying at least one treatment target in search of an agent; means for accessing at least one dataset containing at least one agent for use in the context of the at least one treatment target; means for applying at least one filter criterion to the at least one dataset to identify a subset of the at least one dataset, the subset of the at least one dataset associated with a defined level of at least one adverse event associated with administration of the at least one agent; means for extracting from the at least one dataset the at least one agent in response to the accessing at least one dataset containing at least one agent for use in the context of the at least one treatment target and the applying at least one filter criterion to the at least one dataset to identify a subset of the at least one dataset; and means for presenting the at least one agent in response to the subset of the at least one dataset. In addition to the foregoing, other system aspects are described in the claims, drawings, and text forming a part of the present disclosure.

An embodiment provides a system. In one implementation, the system includes but is not limited to means for accepting at least one treatment target in search of an agent at one or more user interfaces; and means for transmitting data from the one or more user interfaces to at least one data analysis system, the data including at least the treatment target in search of an agent: the data analysis system being capable of identifying at least one agent for use in the context of the at least one treatment target; the data analysis system further being capable of applying at least one filter criterion to the at least one dataset to identify a subset of the at least one dataset, the subset of the at least one dataset associated with a defined level of at least one adverse event associated with administration of the at least one agent; and the data analysis system further being capable of sending a signal to either the one or more user interfaces or a different user interface in response to the subset of the at least one dataset, which signal transmits the at least one agent. In addition to the foregoing, other system aspects are described in the claims, drawings, and text forming a part of the present disclosure.

An embodiment provides a computer program product. In one implementation, the computer program product includes but is not limited to a signal bearing medium bearing one or more instructions for accepting an input identifying at least one treatment target in search of an agent; one or more instructions for accessing at least one dataset containing at least one agent for use in the context of the at least one treatment target; one or more instructions for applying at least one filter criterion to the at least one dataset to identify a subset of the at least one dataset, the subset of the at least one dataset associated with a defined level of at least one adverse event associated with administration of the at least one agent; and one or more instructions for presenting the at least one agent in response to the subset of the at least one dataset. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to accept an input identifying at least one treatment target in search of an agent; access at least one dataset containing at least one agent for use in the context of the at least one treatment target; apply at least one filter criterion to the at least one dataset to identify a subset of the at least one dataset, the subset of the at least one dataset associated with a defined level of at least one adverse event associated with administration of the at least one agent; and present the at least one agent in response to the subset of the at least one dataset. In addition to the foregoing, other system aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other embodiments are set forth and described in the text (e.g., claims and/or detailed description) and/or drawings of the present description.

The foregoing is a summary and thus contains, by necessity, simplifications, generalizations and omissions of detail; consequently, those skilled in the art will appreciate that the summary is illustrative only and is not intended to be in any way limiting. Other aspects, features, and advantages of the devices and/or processes described herein, as defined by the claims, will become apparent in the detailed description set forth herein.

BRIEF DESCRIPTION OF THE DRAWINGS

FIG. 5 illustrates another alternative embodiment of study data associated with the data analysis system of FIG. 1, with specific examples of study data.

FIG. 6 illustrates additional alternative embodiments of study data associated with the data analysis system of FIG. 1, with specific examples of study data.

FIG. 7 illustrates additional alternative embodiments of study data associated with the data analysis system of FIG. 1, with specific examples of study data.

FIG. 13 illustrates an alternative embodiment of the example operational flow of FIG. 8.

The use of the same symbols in different drawings typically indicates similar or identical items.

DETAILED DESCRIPTION

Figure 1:
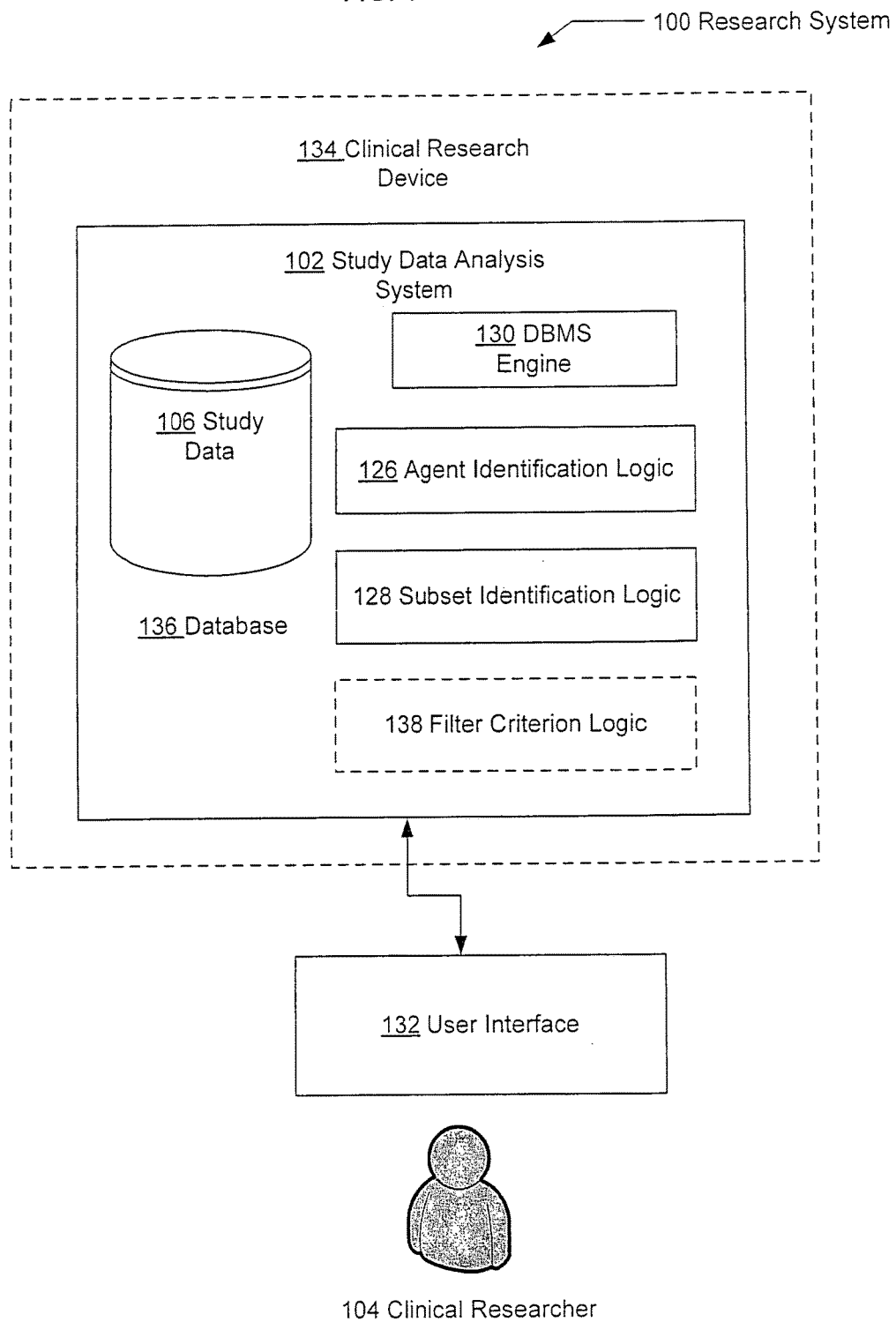
FIG. 1 illustrates an example data analysis system in which embodiments may be implemented, perhaps in a device.

FIG. 1 illustrates an example research system 100 in which embodiments may be implemented. The research system 100 includes a study data analysis system 102. The study data analysis system 102 may be used, for example, to store, recall, access, implement, or otherwise use information obtained from study data 106.

The study data analysis system 102 may be used, for example, to identify agent(s) associated with one or more treatment targets which are associated with a specific subpopulation(s) of individuals for whom the incidence of one or more adverse events is acceptable at a defined level. The study data analysis system 102 may identify such agent(s) by, for example, storing, analyzing and/or providing information obtained from study data 106 as to the safety and effectiveness of the agent(s).

An adverse event, also known as an adverse effect, side effect, or complication, is typically a consequence of agent administration other than the intended consequence of agent administration. In certain embodiments, an adverse event as used herein may have a neutral consequence to an individual, or an adverse event may actually have beneficial effects on an individual though such beneficial effects may be unintended consequences of administration. Examples of adverse events are, without limitation, swelling, pain, nausea, diarrhea, change in blood pressure or other physiological measure, headache, heart attack, allergy, death, and changes in gene expression, protein expression or biochemical activity.

An agent, as used herein, can be, for example, a medical or non-medical intervention, including, for example, administration of prescription or non-prescription medications, small molecule drugs or biologics, nutraceuticals, or dietary supplements. An agent may also be, for example, alcohol or an illicit substance. A treatment target, as used herein, can be, for example, a medical condition, treatment goal or disorder meriting clinical, nutraceutical or alternative medical intervention. Treatment targets may also be voluntary procedures, for example, cosmetic procedures. Treatment, as used herein, can refer to treating and/or prevention. A treatment target is search of an agent is a treatment target of interest (e.g., a medical condition) for which the incidence and/or severity of an adverse event(s) under a standard of care is high and/or unacceptable.

As a further example, the study data analysis system 102 can provide information about which agent(s) are candidates for further testing and development according to defined levels of tolerance for one or more adverse events and/or defined efficacy levels. On the basis of study data analysis, for example, for a given treatment target in search of an agent, an agent may be identified through the use of a filter criterion that functions to identify subsets of data that correspond to a certain level of adverse event. Thus, identified agents exhibit acceptable levels of adverse events in a subset of the data, and optionally are effective in treating the condition at a defined level.

In FIG. 1, the study data analysis system 102 is used by a clinical researcher 104. The clinical researcher 104, for example, may use the study data analysis system 102 to enter, store, request, or access study data relating to a treatment target, medical condition, or prevention target, such as, for example, the various examples provided herein. The clinical researcher 104 may generally represent, for example, a person involved in health care or the health care industry, including, for example, a pharmaceutical company researcher or clinician, a biotechnology company researcher or clinician, a doctor, or a biomedical researcher. The clinical researcher 104 also may represent someone who is involved in health care in the sense of developing, managing, or implementing the study data analysis system 102, e.g., a software developer with clinical knowledge (or access to clinical knowledge), a database manager, or an information technologies specialist. Even more generally, some or all of various functions or aspects described herein with respect to the clinical researcher 104 may be performed automatically, e.g., by an appropriately-designed and implemented computing device, or by software agents or other automated techniques.

Study data 106 is typically data relating to conditions of agent testing, agent dosing and administration schedule, delivery system(s), efficacy, mechanism(s) of action, adverse events, pharmacokinetics, pharmacodynamics, statistical parameters and outcomes, and/or other experimental conditions or results. Study data 106 also may represent or include diagnostic testing, for example, to determine the safety and/or efficacy of a particular agent such as a medication, medical device or surgical treatment. Study data 106 may originate from, for example, an experiment and may be found in one or more different sources, including, for example, published journal articles, clinical trial reports, data reported on internet site(s), data submitted to the Food and Drug Administration or other regulatory agency, data included in pharmacogenomic database(s), data included in genetic database(s), or data found in other relevant database(s) that contain data relating to the conditions of use, effect, mechanism of action or other properties of an agent relevant to a treatment target. Study data 106 may also originate from a mathematical and/or computer simulation(s) of one or more properties of an agent, for example, data from an in vitro/in vivo correlation analysis. Study data 106, for example, could result from pre-clinical testing or clinical testing, and may include data from in vitro testing, in situ testing, in vivo testing in animals or clinical testing in human subjects or patients. A formal clinical trial is one example of a study that results in study data 106.

Study data 106 may include raw data, for example, agent name, agent concentration, dosing, dosing frequency, agent concentration in the blood following administration at various times, minimum and maximum blood concentrations ($C_{min}$ and $C_{max}$, respectively), the times at which $C_{min}$ and $C_{max}$ occur ($T_{min}$ and $T_{max}$, respectively), measured effect of the agent(s) on blood protein, lipid or cell levels, and/or reported adverse events experienced by study participants.

Study data 106 may also include study participant information such as, for example, age, weight, gender, race, ethnicity, dietary factors, medical history, concomitant medications, and other demographic characteristics. Study data 106 may also include molecular information about study participants such as, for example, genomic DNA sequence, cDNA sequence, single nucleotide polymorphisms (SNP's), haplotype profile, insertion and/or deletion (INDEL) profile, restriction fragment length polymorphism (RFLP) profile, chromatin state, nucleosome and/or histone/nucleoprotein composition, RNA sequence, micro RNA sequence, pyknon sequence and/or profile, RNA expression levels, protein sequence, protein expression levels, cytokine levels and/or activity, circulating hormone levels and/or activity, circulating carbohydrate levels, neurotransmitter levels, nitric oxide levels, liver enzyme expression and/or activity, gastrointestinal enzyme expression and/or activity, renal enzyme expression and/or activity, and/or other biochemical markers.

Study data 106 may include data points that are, for example, ordinals (e.g., $1^{st}$, $2^{nd}$, $3^{rd}$), nominals (e.g., nausea, congestive heart failure), binaries (e.g., alive/dead), genetic (e.g., AGCGGAATTCA), and/or continuous (e.g., 1-4, 5-10).

As a further example, the study data analysis system 102 (including agent identification logic 126, subset identification logic 128 and/or filter criterion logic 138) may employ a filter criterion to identify within study data 106 one or more subsets of data corresponding to population(s) having a defined level of tolerance for one or more adverse events and, optionally, a defined efficacy level. The filter criterion, for example, may specify a level of adverse event that serves to limit the study data 106 to a specific subset of data containing, for example, a desired incidence of a certain adverse event. Study data 106 may report adverse event levels and/or efficacy levels; it is understood that such reported data may or may not precisely match actual adverse event levels and/or efficacy levels.

The study data analysis system 102 also may correlate subpopulation adverse event data with subpopulation identifier data to identify one or more clinically relevant patient populations. For example, an agent may be identified using the study data analysis system 102 that is effective and that exhibits tolerable adverse events in a subpopulation that is characterized by a particular molecular marker. The study data analysis system 102 may then be used to further search, for example, one or more population databases to find subpopulation identifier data 314 (FIG. 3) that correlate the molecular marker with one or more clinically relevant patient populations. Such population databases include, for example, those that contain molecular information about individuals or populations such as, for example, genomic DNA sequence, cDNA sequence, single nucleotide polymorphisms (SNP's), haplotype profile, insertion and/or deletion (INDEL) profile, restriction fragment length polymorphism (RFLP) profile, chromatin state, nucleosome and/or histone/nucleoprotein composition, RNA sequence, micro RNA sequence, pyknon sequence and/or profile, RNA expression levels, protein sequence, protein expression levels, cytokine levels and/or activity, circulating hormone levels and/or activity, circulating carbohydrate levels, neurotransmitter levels, nitric oxide levels, liver enzyme expression and/or activity, gastrointestinal enzyme expression and/or activity, renal enzyme expression and/or activity, and/or other biochemical markers.

Ongoing, prospective and completed clinical trials for various agents may be found in databases such as http://www.clinicaltrials.gov, which lists specific details for clinical trials, including primary and secondary outcomes, enrollment size, inclusion and exclusion criteria, and other parameters. In addition, clinical trial results are generally available in journal publications that are known to, and accessible by, persons of ordinary skill in the art.

The study data analysis system 102 (including agent identification logic 126, subset identification logic 128 and/or filter criterion logic 138) may apply appropriate statistical methods to study data 106, which may provide, for example, an average value(s) for a set of data, a confidence level(s) for a confidence interval(s), p-value(s), or other measures of statistical significance for multiple data points in one or more data sets, such as observed or simulated study data 106. Such statistical methods may comprise the filter criterion of the claimed methods and systems. For example, the study data analysis system 102 may include filter criterion logic 138 that is capable of applying a statistical filter to study data 106 as a means of screening out irrelevant and/or statistically insignificant data. Alternatively, the subset identification logic 128 may perform the application of a filter criterion to study data 106. Alternatively, a filter criterion may be input by a clinical researcher 104 via a user interface 132.

Study data 106 relating to safety and efficacy of an agent in terms of treating, for example, a medical condition, often is associated with a statistical measure of significance in terms of, for example, a clinical endpoint of an experimental trial. For example, an agent administered to patients with a medical condition, according to a defined dosing schedule, may relieve one or more symptoms of the medical condition to an extent that is statistically significant when compared to the effect of a placebo. Further, administration of the agent may result in a statistically significantly higher incidence of an adverse event than is observed following administration of a placebo.

Statistical analysis can be classified into two main groups: hypothesis testing and estimation. In hypothesis testing, a study typically compares the occurrence of one or more endpoints in two or more groups of participants. This often involves a comparison of the mean, proportion, or other data parameter of, for example, study adverse event data 308 (FIG. 3) in a test group to the same study adverse event data 308 (FIG. 3) in a control group. Study adverse event data, for example, may include measures such as mean levels of sleeplessness or gastrointestinal discomfort associated with administration of a given agent. Study efficacy data, for example, may include measures such as the mean time to healing or pain relief, or the proportion of patients who showed a threshold degree of improvement at various times after administration of one or more agent(s).

In estimation, the goal is to determine the relative value of a characteristic of interest in a group under study. The estimated value is usually accompanied by a statement about its certainty, or confidence interval, which is expressed as a percentage. Estimation is important in hypothesis testing and in the analysis of safety variables. For example, in a study of a generic medication, where efficacy is equivalent to that of the reference medication, the FDA and the sponsor may be interested in estimating the proportion of patients that might experience a particular adverse event. To ensure that the estimate has a high probability of being accurate, the study data analysis system 102 would determine the confidence interval for the estimate.

In the evaluation of study data 106, from whatever source, the character of the data is informative in terms of determining appropriate statistical measures to use to identify significant relationships and effects. The character of the data includes, for example, (1) the nature of the distribution of the primary, secondary, and influencing variables; (2) normal (Gaussian) or other well-known distributions; (3) if the data are not normally distributed, can they be chanced by a function (e.g., a transformation) that preserves their order, but brings them into conformity with well-known assumptions about their distribution; (4) large enough sample size such that normality of the means can be assumed even if the data are not normally distributed; and/or (5) equality of variances of subgroups to be compared. These characteristics can be ascertained by applying common tests or by using basic data plots such as histograms or box plots. Knowing these characteristics of the data allows the study data analysis system 102 to validate the assumptions that underlie the data, and to select the most appropriate analytical method consistent with the data.

Study data 106 may, for example, contain two types of variables, quantitative and/or qualitative. Quantitative variables are numbers that can have, for example, a value within some acceptable range. For example, a person's blood pressure could be 120/80. Qualitative variables, however, typically lie within discrete classes, and are often characterized numerically by whole numbers. For instance, a patient who experiences nausea after agent administration could be characterized by a one, and a patient that does not could be classified as a zero. Qualitative variables may also be characterized by words.

The distribution of variables in a sample is important in determining what method of statistical analysis can be used. Normal, or Gaussian, distribution resembles the symmetrical bell-shaped curve by which most students are graded throughout their scholastic careers. It is typically characterized by two features: the mean, which is a measure of the location of the distribution, and the variance, which is a measure of the spread of the distribution. Many well-known statistical methods for analyzing means, such as the t-test or the paired t-test, rely on a normal distribution to ensure that the mean represents a measure of the center of the distribution.

Because statistical theory holds that the means of large samples are approximately normally distributed, an assumption of normality becomes less important as sample sizes increase. However, when sample sizes are small, it is important to determine whether the data to be analyzed are consistent with a normal distribution or with another well-characterized distribution.

Most common statistical tests of quantitative variables, including the t-tests and analysis of variance (ANOVA), are tests of the equality of the measures of location belonging to two or more subgroups that are assumed to have equal variance. A measure of location, such as a mean or median, is a single number that best describes the placement of the distribution (usually its center) on a number line. Because equal variance provides the basis of most tests that involve measures of location, in such cases an assumption of equal variance is more important than an assumption of normality, even when the tests do not rely on a specific distribution of the data (i.e., nonparametric tests). If the variances are not equal among the subgroups being compared, it is frequently possible to find a formula or function (e.g., a transformation) that preserves order and results in variables that do have equal variance.

When considering the distribution of data, it is also useful to look at a picture of them. The study data analysis system 102 can plot data to determine whether the distribution is shifted toward higher or lower values (skewed). The presence of one or more values that are much higher or lower than the main body of data indicates possible outliers. Data plots can also help to locate other data peculiarities. Common, statistically sound adjustment methods can be used to correct many types of data problems.

Once the character of the variables of interest has been established, the study data analysis system 102 can test for comparability between the treatment and control groups. Comparability is established by performing statistical tests to compare, for example, demographic factors, such as age at the time of the study, age at the time of disease onset, nationality, economic status, migration status, and/or gender; or prognostic factors measured at baseline, such as disease severity, concomitant medication, or prior therapies. Biased results can occur when the comparison groups show discrepancies or imbalances in variables that are known or suspected to affect primarily or secondary outcome measures. For instance, when a group includes a large proportion of participants whose disease is less advanced than in those of a comparison group, the final statistical analysis will often show a more significant effect for the patients whose disease is less advanced, even though the effect may not be primarily caused by an administered agent.

For example, in a trial comparing the effectiveness of surgery and iodine-131 for treatment of hyperthyroidism, clinical researchers found that, surprisingly, patients who received the allegedly less-traumatic radiation therapy had a much higher frequency of illness and death than those who underwent surgery. Examination of the baseline characteristics of the two groups revealed that the patients selected for the surgery group were generally younger and in better health than those selected for the iodine treatment. The inclusion criteria for the surgery group were more stringent than those for the iodine group because the patients had to be able to survive the surgery.

It is desirable to perform comparability tests using as many demographic or prognostic variables simultaneously as the method of analysis will allow. The reason for using this approach is that the influence of a single, for example, demographic or prognostic characteristic on an outcome variable may be strongly amplified or diminished by the simultaneous consideration of a second characteristic. However, the size of many clinical trials is often insufficient to allow the simultaneous consideration of more than two variables. More commonly, the sample size of the study will allow consideration of only one variable at a time.

Imbalances detected in comparability testing do not necessarily invalidate study results. By tracking such differences, however, the study data analysis system 102 can account for their presence when comparing study data from treatment and control groups. Many statistical procedures can be used to adjust for imbalances either before or during an analysis, but such adjustments should be limited to cases where the extent of the difference is relatively small, as judged by a person of ordinary skill in the art.

Methods used for comprehensive analysis of study data 106 vary according to the nature of the data, but also according to whether the analysis focuses on the effectiveness or the safety of the agent. Selection of an appropriate statistical method should also take into account the nature of the agent under study. For example, in vitro diagnostic studies may use statistical techniques that are somewhat specialized. Often the analysis is based on a specimen, such as a vial of blood, collected from a patient. The same specimen is typically analyzed by two or more laboratory methods to detect an analyte that is related to the presence of a condition or disease. Thus, each specimen results in a pair of measurements that are related to one another. The statistical treatment of such related (or correlated) data is very different from that of unrelated (or uncorrelated) data because both measurements are attempting to measure exactly the same thing in the same individual. Generally, if both laboratory measurements result in a quantitative variable, a first statistical analysis will attempt to measure the degree of relationship between the measurements. The usual practice is to perform a simple linear regression analysis that assumes that the pairs of values resulting from the laboratory tests are related in a linear way.

In linear regression analysis, a best-fit line through the data is found statistically, and the slope is tested to determine whether it is statistically different from zero. A finding that the slope differs from zero indicates that the two variables are related, in which case the correlation coefficient, a measure of the closeness of the points to the best-fit line, becomes important. A correlation coefficient with a high value, either positive or negative, indicates a strong linear relationship between the two variables being compared. However, this correlation is an imperfect measure of the degree of relationship between the two measurements. That is, although a good correlation with a coefficient near one may not indicate good agreement between the two measurements, a low correlation is almost surely indicative of poor agreement.

Although correlation can indicate whether there is a linear relationship between two study measurements, it does not provide good information concerning their degree of equivalence. Perfect equivalence would be shown if the correlation were very near one, the slope very near one, and the intercept very near zero. It is possible to have a very good relationship between the two measures, but still have a slope that is statistically very different from one and an intercept that is very different from zero. In such a situation, one of the two measurements may be biased relative to the other.

Another relevant analysis of study data is a relative risk assessment or a receiver operating characteristic (ROC) analysis. Software is available to perform either of these analyses. A relative risk assessment is a ratio of the risk of a condition among patients with a positive test value to the risk of the condition among patients with a negative test value. The relative risk analysis can be done by use of either a logistic regression or a Cox regression depending on whether the patients have constant or variable follow-up, respectively. ROC analysis provides a measure of the robustness of the cutoff value as a function of sensitivity and specificity.

Analysis of the effectiveness and/or safety of an agent typically involves hypothesis testing to determine whether the agent maintains or improves the health of patients in a safe way. In some cases, a particular agent may be compared to an agent of known function. In such cases, the result will be a test of the hypothesis that the unknown agent is better than or equal to the known agent. Selection of an appropriate statistical method for analysis of data from such studies depends on the answers to many questions, such as (1) is the primary variable quantitative or qualitative; (2) was the primary variable measured only once or on several occasions, (3) what other variables could affect the measurement under evaluation; and (4) are those other variables qualitative (ordered or not) or quantitative?

If the primary variable under evaluation is quantitative, selection of an appropriate method of analysis will depend on how many times that variable was measured and on the nature of any other variables that need to be considered. If there is only a single measurement for each variable, and there are no differences among, the potential covariates belonging to the treated and control groups, the appropriate method of analysis may be a parametric or nonparametric ANOVA or t-test. For example, a study of a new cardiovascular agent that is expected to offer better protection against congestive heart failure ("CHF"), with all other things being equal, could compare six-month CHF rates of incidence by this method.

The choice of an appropriate analytical method chances if the covariates belonging to the two comparison groups differ and are measured qualitatively. Such cases may use a more complex analysis of variance or an analysis of covariance (ANCOVA). The ANCOVA method is particularly suited to analyzing variables that are measured before and after treatment, assuming that the two measurements are related in a linear or approximately linear manner. Using ANCOVA, the clinical researcher first adjusts the post-treatment measure for its relationship with the pre-treatment measure, and then performs an analysis of variance. Using the example of the cardiovascular agent, ANCOVA would be a suitable method of analysis if the amount of improvement in the six-month CHF rates of the patients treated by the agent depended, for example, on the patients' pre-treatment level of coronary artery blockage.

Outcome variables are often measured more than once for each study subject. When this is done, it should be done in a balanced way such that when a variable is measured it is measured for every patient. A balanced-repeated-measures ANOVA can be performed with or without covariates. With covariates, this method reveals the effect of each patient's covariate value on the outcome variable, the effect of time for each patient, and whether the effect of time for each patient is changed by different values of the covariate. Continuing with the CHF example, a repeated-measures ANOVA could be applied to evaluate measurements of coronary artery blockage before agent administration and at 3, 6, 9, and 12 months after initiation of dosing, and the number of coronary arteries that are at least 50% blocked. In this case, the primary outcome variable is the level of coronary artery blockage, and the covariate is the number of coronary arteries that are at least 50% blocked.

A repeated-measures ANOVA also can be used if a few patients missed a small number of measurements. However, in doing so the study data analysis system 102 may use other statistical algorithms known in the art in order to estimate the missing outcome measures.

Some studies result in a quantitative outcome variable and one or more quantitative covariates. In this situation, multiple regression methods are useful in evaluating outcome variables (called dependent variables), especially if the study involves several levels or doses of treatment as well as other factors (independent variables). Regression is a powerful analytical technique that enables the study data analysis system 102 to simultaneously assess the primary variables as well as any covariates.

The regression model is an equation in which the primary outcome variable is represented as a function of the covariates and other independent variables. The importance of each independent variable is assessed by determining whether its corresponding coefficient is significantly different from zero. If the coefficient is statistically greater than zero, then that independent variable is considered to have an effect on the dependent variable and is kept in the model; otherwise, it is discarded. The final model includes only those variables found to be statistically related to the dependent variable. The model enables the study data analysis system 102 to determine the strength of each independent variable relative to the others, as well as to the agent effect. In the CHF agent example, a multiple regression analysis would be appropriate for data where the level of coronary artery blockage was measured twice (e.g., at baseline and at 6 months), and the number of coronary arteries that are at least 50% blocked was measured as an independent variable.

For studies in which the outcome variable is qualitative, other types of analysis may be employed. Some of these resemble the methods used to analyze quantitative variables. For instance, log-linear modeling can be used to develop the same types of evaluations for a qualitative outcome variable as ANOVA and ANCOVA provide for quantitative measures.

Log-linear modeling techniques are equivalent to such commonly used Chi-square methods as the Cochran-Mantel-Haenzel method. They enable the study data analysis system 102 to compare the distribution of treatment and control patients within outcome classes; some techniques also make it possible to determine how consistent the influence of covariates is, and to adjust for that influence.

Because qualitative variables are represented by whole numbers, these methods may use special algorithms in order to estimate quantities of interest. Finding solutions for estimating those quantities can be accomplished readily with the aid of computer programs known in the art.

Logistic regression methods are the qualitative counterparts to the multiple regression techniques described for quantitative variables. While the two methods include models and interpretations that correspond closely, logistic regression computations are not as straightforward as those for multiple regression. Even so, they enable the study data analysis system 102 to determine relationships between the outcome variable and independent variables. Logistic regression allows the use of either quantitative or qualitative covariates, but it is preferred that study participants have a follow-up time that is essentially the same.

In logistic regression methods, a proportion is represented by a complex formula, a part of which is a multiple regression-like expression. By estimating the coefficients for the independent variables, including the agent administration, the study data analysis system 102 is able to determine whether a particular independent variable is statistically related to the dependent variable. The final model contains only these independent variables, the coefficients of which differ significantly from zero. Further, the logistic regression method estimates the odds ratio: a measure of the relative risk for each independent variable adjusted for the presence of the other variables. For example, if the agent were a special light designed to treat a fungus on the toenail, and if the logistic regression measured the rate of cure at 3 months after treatment, then an odds ratio of 7.9 for the treatment would imply that, adjusted for other variables in the final model, patients who had the treatment were 7.9 times more likely to experience a cure at 3 months than patients who did not have it.

The Cox regression method is another technique for analyzing qualitative outcome measures. This method can determine the effect of agents and other potential covariates even when the data do not have the same follow-up time. It yields a model and results that are analogous to those of the logistic regression method, but are not limited to patient survival outcomes. This method can be applied to, for example, an outcome that includes measurement of the time to a particular event, such as time to healing or cure. A powerful characteristic of the Cox regression method is that it keeps the study participant in the analysis until he or she drops out of the study. This can be an important factor in small studies, in which statistical power can be reduced when even a modest number of participants are unavailable for follow-up.

As in the case of effectiveness analyses, the selection of statistical methods appropriate for safety analyses depends on many factors. If the FDA and the clinical researcher have a great deal of knowledge about adverse events associated with a specific treatment target and its therapeutic agents, estimating the rate of adverse event with corresponding 95% confidence intervals may be appropriate. But if little is known about those adverse events, a more elaborate statistical treatment may be appropriate.

The most common method used to analyze adverse events is to compute freedom-from-complication rates by survival methods; one of the most commonly used analysis procedures for survival data is the Kaplan-Meier method. The popularity of this method is partly attributable to the fact that it measures the time to occurrence of an adverse event, and, like the Cox regression method, keeps participants in the life table until they drop out of a study. In addition, at the occurrence of each adverse event, the Kaplan-Meier method provides an estimate of the adverse event rate and its standard error, enabling the study data analysis system 102 to compute confidence intervals for each adverse event.

A related method is the life table method, in which the study duration is divided into equal segments and the proportion of events and participant drop-outs is evaluated for each segment. For example, if the study had a one-year duration, the life table could be viewed as 12 one-month segments. Calculation of rates would depend on the number of participants that entered the study each month, the number of events that occurred in that month, the number of participants that dropped out of the study in that month, and the number of participants who went on to the next month. The adverse event rate is calculated for each month rather than at the occurrence of each adverse event, and the standard error is also determined, allowing for the computation of confidence intervals.

If it is necessary to test the hypothesis that two samples (such as a control and treated group) have the same adverse event experience for the study duration in the presence of covariates, this can be accomplished by comparing survival (freedom from complication) rates derived through use of the Cochran-Mantel-Haenzel method or an equivalent procedure. Cox regression provides a good method with which to determine the relative importance of covariates on a rate of adverse events.

Such analytical methods are useful for comparing the rates at which a treated and control group encounter their first occurrence of an adverse event, but the occurrence of multiple adverse events or multiple occurrences of the same adverse event do not lend themselves readily to a single appropriate analytical technique. A combination of non-independent analyses is preferred to completely explain the effects of multiple adverse events.

Numerical relationships detected as statistically significant by regression techniques are associations, not cause-and-effect relationships. To support the associative evidence provided by such analyses, the study data analysis system 102 may also make use of pre-clinical animal studies and other data that reinforce the determination of cause-and-effect, where available.

While it is generally desirable to prospectively design a study to provide statistically significant measures of safety and efficacy, retrospective analysis of study data 106 may provide adequate means for determining statistical relationships among the data. Alternatively, statistically significant measures of study data 106 may be unavailable in some cases. For example, an analysis of study data 106 may indicate an association between a small subset of patients enrolled in a clinical trial and a decreased incidence of an adverse event. Because of the small sample size of the subset of patients, the study data 106 may lack statistical power to indicate whether the association is statistically significant (e.g., the p-value may be >0.05). The association, however, may nevertheless be of interest by virtue of, for example, (1) magnitude of effect and/or (2) coincidence with a known mechanism of action of the agent. Therefore, the claimed subject matter should not be limited to study data analysis of, for example, a specific statistical level of significance. Many applications of the study data analysis system 102 exist, over and above the examples provided herein.

Study data 106 may include reported or calculated mean values of the parameters discussed above such as, for example, arithmetic, geometric and/or harmonic means. Study data may also include reported or calculated statistical measures such as student's t-test, p-value, chi square value(s), and/or confidence interval or level. Alternatively, the study data analysis system 102 may calculate an appropriate statistical measure using raw data.

As discussed above, a filter criterion may be applied to the study data 106 as a means of screening out unwanted, irrelevant, or statistically insignificant data. Such a filter criterion may be applied, for example, by the subset identification logic 128 itself, by a separate filter criterion logic 138, or by input from a clinical researcher 104 through a user interface 132.

In this regard, it should be understood that the herein claimed study data analysis system 102 can, for a given treatment target in search of an agent, (1) identify agents that are associated with a defined level of adverse events in the context of various reported or/calculated statistical measures (2) apply at least one filter criterion to identify subsets of data that are associated with the defined level of adverse events in the context of various reported or calculated statistical measures, and (3) present the agent and/or subset of data in response to the identification of the subset of data.

For example, many databases may be searched singly or in combination to identify one or more agents that exhibit a particular level of adverse events in the context of treating a given condition. Similarly, many databases exist that may be searched singly or in combination to identify one or more subsets of data having a defined tolerance for at least one adverse event upon administration of the one or more agents. Similarly, many databases exist that may be searched singly or in combination to identify one or more subpopulations having a defined level of efficacy upon administration of the one or more agent.

Some conditions have a genetic component and are more likely to occur among people who trace their ancestry to a particular geographic area. People in an ethnic group often share certain versions of their genes, called alleles, which have been passed down from common ancestors. If one of these shared alleles contains a disease-causing mutations a particular genetic disorder may be more frequently seen in that particular ethnic group than in others.

Examples of genetic conditions that are more common in particular ethnic groups are sickle cell anemia, which is more common in people of African, African-American, or Mediterranean heritage; and Tay-Sachs disease, which is more likely to occur among people of Ashkenazi (eastern and central European) Jewish or French Canadian ancestry.

Linkage disequilibrium (LD) is a term used in the field of population genetics for the non-random association of alleles at two or more genetic loci, not necessarily on the same chromosome. LD describes a situation in which some combinations of alleles or genetic markers occur more or less frequently in a population than would be expected from a random assortment of allelic sequences based on their frequencies. For example, in addition to having higher levels of genetic diversity populations in Africa tend to have lower amounts of linkage disequilibrium than do populations outside Africa, partly because of the larger size of human populations in Africa over the course of human history and partly because the number of modern humans who left Africa to colonize the rest of the world appears to have been relatively low. In contrast, populations that have undergone dramatic size reductions or rapid expansions in the past and populations formed by the mixture of previously separate ancestral groups can have unusually high levels of linkage disequilibrium.

Linkage disequilibrium-based genome screening is a tool used to localize genes responsible for common diseases. This screening involves many more markers than traditional linkage studies and therefore presents the issue of defining an appropriate significance threshold that takes into account the consequent multiple comparisons. False Discovery Rate (FDR) has been used as a measure of global error in multiple tests for LD screening. Controlling FDR leads to an increased power to detect more than one locus, making this strategy particularly appealing for complex disease mapping. Such methods, including permutation-based evaluations of FDR within the sample of interest, for example, may be used to perform multivariate analyses among study data sets.

Databases that contain study data 106 relating to, for example, the genetic make-up of a population, agent efficacy, and/or agent adverse events include, for example, those found on the internet at the Entrez websites of the National Center for Biotechnology Information (NCBI). NCBI databases are internally cross-referenced and include, for example, medical literature databases such as PubMed and Online Mendelian Inheritance in Man; nucleotide databases such as GenBank; protein databases such as SwissProt; genome databases such as Refseq; and expression databases such as Gene Expression Omnibus (GEO). Also useful are publication databases such as Medline and Embase.

Other databases include, for example, IMS Health databases of prescribing information and patient reporting information such as that contained in the National Disease and Therapeutic Index (NDTI) database, which provides a large survey of detailed information about the patterns and treatment of disease from the viewpoint of office-based physicians in the continental U.S. Also of use is the U.S. Food and Drug Administration's (FDA's) Adverse Event Reporting System (AERS) database. This database contains adverse drug reaction reports from manufacturers as required by FDA regulation. In addition, health care professionals and consumers send reports voluntarily through the MedWatch program. These reports become part of a database. The structure of this database is in compliance with the international safety reporting guidance issued by the International Conference on Harmonization. The FDA codes all reported adverse events using a standardized international terminology called MedDRA (the Medical Dictionary for Regulatory Activities). Among AERS system features are the on-screen review of reports, searching tools, and various output reports. Another adverse drug events database is DIOGENES®, a database consisting of two sub-files: Adverse Drug Reactions (ADR) and Adverse Event Reporting System (AERS). ADR records contain data regarding a single patient's experience with a drug or combination of drugs as reported to the FDA. Since 1969, the FDA has legally-mandated adverse drug reaction reports from pharmaceutical manufacturers and maintained them in their ADR system. In November 1997, the ADR database was replaced by the AERS. Other adverse event reporting databases include, for example, the Vaccine Adverse Event Reporting System (VAERS) and the Manufacturer and User Facility Device Experience Database (MAUDE).

In one embodiment, the study data analysis system 102 accepting an input identifying at least one treatment target in search of an agent, accessing at least one dataset containing at least one agent for use in the context of the at least one treatment target in search of an agent, applying at least one filter criterion to the at least one dataset to identify a subset of the at least one dataset, the subset of the at least one dataset associated with a defined level of at least one adverse event associated with administration of the at least one agent 302 (FIG. 3), and presenting the at least one agent in response to the subset of the at least one dataset. In doing so, the study data analysis system 102 may identify a subset of the at least one dataset characterized by, for example, one or more molecular parameters such as, for example, DNA sequence, protein sequence, or protein expression level. The study data analysis system 102 optionally may then confirm that the subset of the at least one dataset exhibits at least some defined level of efficacy upon administration of the at least one agent 302 (FIG. 3) to the subset of the at least one dataset, for example, by referring to study efficacy data 306.

Data, subsets of data, or parameters characterizing a population or subpopulation, as described and claimed herein, refer generally to data regarding a human or animal population or a human or animal subpopulation. For example, data characterizing a population or subpopulation may be, for example, reported in the scientific literature, self-reported, measured, reported in survey results, present in archival documentation, and/or anecdotal in nature.

A subset of data characterized by, for example, one or more molecular profiles may not, at first glance, correspond to a known, clinically-defined segment of the global or a national population. The study data analysis system 102 may therefore perform the additional step of correlating the at least one subset of the at least one dataset associated with a defined level of at least one adverse event associated with administration of the at least one agent with subpopulation identifier data. As an example, a subset of the at least one dataset associated with a defined level of at least one adverse event may be correlated with molecular or other profiles of known ethnic, gender, age or other demographic feature. As a specific example, a subset of data characterized by a specific DNA sequence may be matched with an ethnic genomic DNA database(s) to identify an ethnic group in which the specific DNA sequence is more common than in the general population. Such an ethnic population may accordingly be identified as of increased interest for further study as possible beneficiaries of treatment with the agent in question.

Figure 3:
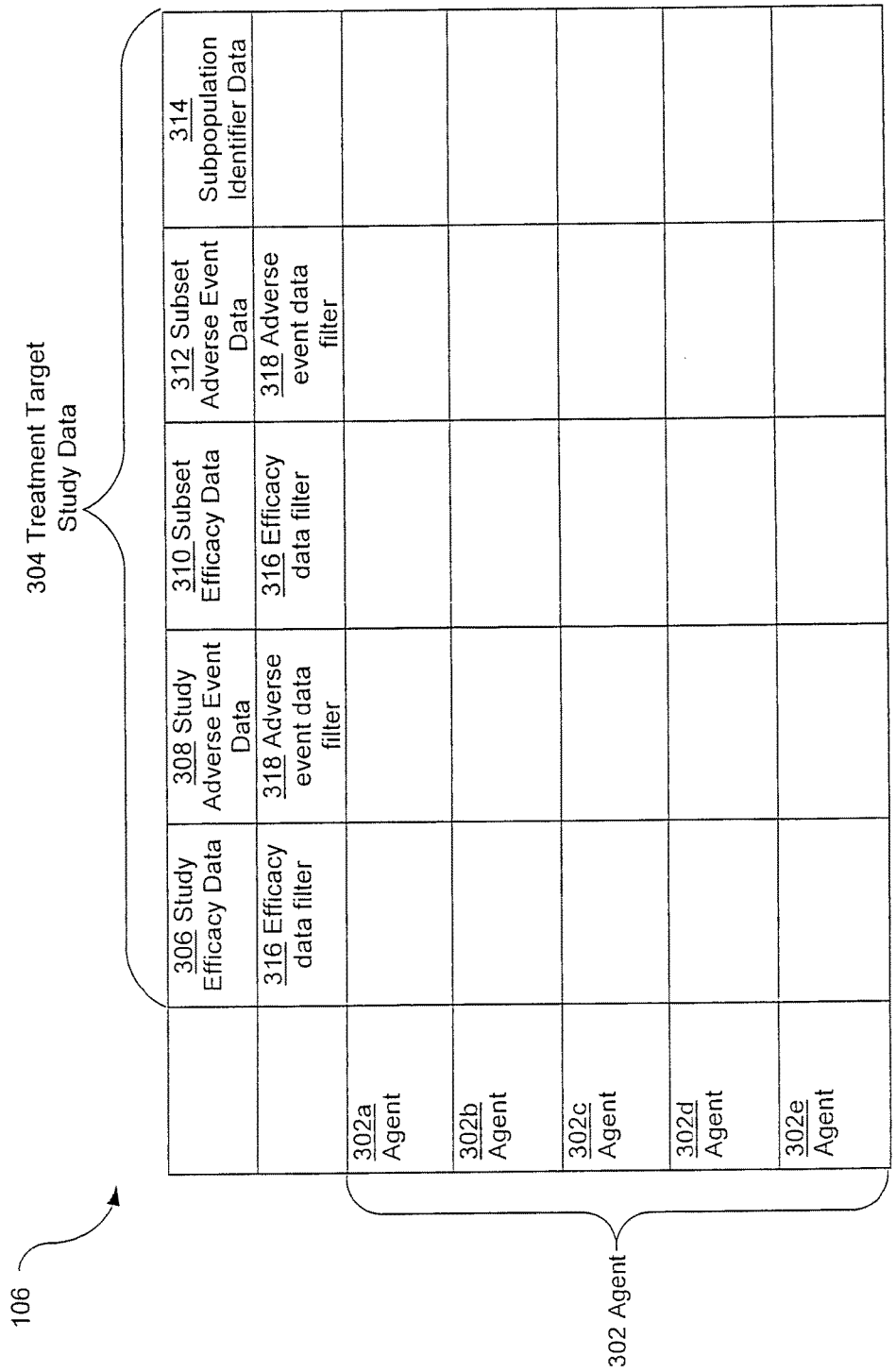
FIG. 3 illustrates an alternative embodiment of study data associated with the data analysis system of FIG. 1.

Additionally, the claimed subject matter may be used with a medical device(s) as the agent 302 (FIG. 3). For example, MAUDE, mentioned above, may be searched to identify a subset of data in which an agent 302 (FIG. 3), in this case a medical device, is associated with a defined level of one or more adverse events and optionally effective in addressing a treatment target. MAUDE data represent reports of adverse events involving medical devices. The data consist of voluntary reports since June 1993, user facility reports since 1991, distributor reports since 1993, and manufacturer reports since August 1996.

Surgical intervention may also be a claimed agent 302 (FIG. 3). For example, surgical ovarian ablation, in which the ovaries are removed to reduce the risk of breast cancer in pre-disposed populations, is associated with important adverse events such as hot flashes, impaired sleep habits, vaginal dryness, dyspareunia, and increased risk of osteoporosis and heart disease. Though use of the systems claimed herein, subpopulations may be identified for which the incidence of such adverse events is lower. For example, subpopulations of women taking hormone replacement therapy (HRT) may be better candidates for ovarian ablation due to the effects of HRT such as, for example, decreased risk of osteoporosis and heart disease. Thus, a filter criterion specifying decreased risk of osteoporosis may be used to identify women having had ovarian ablation as a subset and associated agent that is associated with a decreased incidence of osteoporosis as the adverse event.

Although many other examples are provided herein and with reference to the various figures, it should be understood that many types and instances of study data 106 may play a role in the use and application of the various concepts referenced above and described in more detail herein. The study data analysis system 102 may store such study data 106 in a database 136 or other memory, for easy, convenient, and effective access by the clinical researcher 104.

The study data 106 may include, for example, not only clinical study data and/or corresponding adverse event and/or efficacy data, but also various other parameters and/or characteristics related to subjects or patients to whom an agent 302 (FIG. 3) has been administered, examples of which are provided herein. Through detailed storage, organization, processing, and use of the study data 106, the clinical researcher 104 may be assisted in identifying optimal subsets of data, subpopulations and agents, in order, for example, to find a new target population for an otherwise under-utilized agent 302 (FIG. 3). Ordered assignment, processing, and/or storage of information within the study data 106, as described herein, facilitates and/or enables such recall, access, and/or use of the study data 106 by the clinical researcher 104 in identifying the subset of the at least one dataset, agent, and/or subpopulation identifier data.

In the study data analysis system 102, agent identification logic 126, subset identification logic 128, and/or filter criterion logic 138 may be used to store, organize, access, filter, process, recall, or otherwise use the information stored in the study data 106. For example, the agent identification logic 126 may access a database management system (DBMS) engine 130, which may be operable to perform computing operations to insert or modify new data into/within the study data 106, perhaps in response to new research or findings, or in response to a preference of the clinical researcher 104. For example, if a new agent is discovered to be effective in a certain condition, the clinical researcher 104 may access the study data analysis system 102 and/or agent identification logic 126 and/or subset identification logic 128 through a user interface 132, in order to use the DBMS engine 130 to associate the new agent with one or more subsets or subpopulations for which the incidence of a specific adverse event is acceptable, i.e., within a defined tolerance level. As another example, if data from a new study, e.g., a clinical trial report, indicate that an agent 302 (FIG. 3) is effective and safe in a subset or subpopulation that was not specifically identified in the clinical trial report by the trial sponsors, the study data analysis system 102, filter criterion logic 138, and/or subset identification logic 128 may identify that subpopulation and present the agent 302 (FIG. 3) to a user interface 132 in response to a query from a clinical researcher 104. Such identification may be performed by use of a filter criterion that can remove or select subsets of data.

Similarly, in a case where a clinical researcher 104 seeks, for example, to identify an agent(s) 302 (FIG. 3) that is safe and effective for administration to patients according to a specific profile, the clinical researcher 104 may access the user interface 132 to use the agent identification logic 126, subset identification logic 128, filter criterion logic 138, and/or DBMS Engine 130 to find an agent(s) 302 that fits the profile and/or to find an agent(s) 302 (FIG. 3) that may be promising, for further study. For example, if a specific treatment for a medical condition is typically associated with an unacceptable level of a specific adverse event, then the clinical researcher 104 may input this information via the user interface 132 in order to obtain one or more options for treating or preventing the condition in one or more subpopulations that exhibit acceptable levels of the specific adverse event. In such an example, a clinical researcher 104 may input a filter criterion that, for example, specifies a level of adverse event, or removes from the analysis data that is statistically insignificant or below a certain statistical threshold.

As another example, if a clinical researcher 104 is interested in medical condition X in search of a better agent than those currently available, then the clinical researcher 104 may search for agents 302 (FIG. 3) that are effective in treating medical condition X, and subpopulations in which administration of agents 302 (FIG. 3) results in acceptable levels of a specific adverse event by applying a filter criterion that defines the acceptable levels of the specific adverse event. The agent identification logic 126, subset identification logic 128, and/or filter criterion logic 138 may interface with the DBMS engine 130 to obtain, from the study data 106, one or more subsets of data or subpopulations that exhibit an adverse event profile at a specified tolerance level. In this case, once the subset of data or subpopulation is identified, the study data analysis system 102 and/or agent identification logic 126, and/or subset identification logic 128, and/or filter criterion logic 138 would present the agent(s) 302 (FIG. 3) to the user interface 132 and the clinical researcher 104 as one(s) that meets the input criteria, including the filter criterion.

It should be understood that adverse event data may represent effects of an agent 302 (FIG. 3) itself and/or effects of a delivery system associated with an agent 302 (FIG. 3). For example, in the case of an agent 302 (FIG. 3) administered via liposomal delivery, the liposomes themselves may give rise to adverse events such as accumulation in the liver and spleen, and extravasation into non-target tissues. The present systems may be used to also identify subsets, agents, and/or subpopulations for which such delivery system adverse events are tolerable.

As a general matter, a clinical researcher 104. e.g., a pharmaceutical scientist or a biomedical researcher, may not be aware of all currently available content of the study data 106. Thus, the study data analysis system 102 and/or agent identification logic 126 and/or subset identification logic 128 and/or filter criterion logic 138 provides the clinical researcher 104 with fast, accurate, current, and/or comprehensive adverse event and/or efficacy information, and also provides techniques to ensure that the information remains accurate, current, and/or comprehensive, by allowing the addition and/or modification of the existing study data 106, as new study information becomes available.

In FIG. 1, the study data analysis system 102 is illustrated as possibly being included within a clinical research device 134. The clinical research device 134 may include, for example, a mobile computing device, such as a personal digital assistant (PDA), or a laptop computer. Of course, virtually any other computing device may be used to implement the study data analysis system 102, such as, for example, a workstation, a desktop computer, a networked computer, a collection of servers, or a tablet PC.

Additionally, not all of the study data analysis system 102 need be implemented on a single computing device. For example, the study data 106 may be stored on a remote computer, while the user interface 132 and/or agent identification logic 126, and/or subset identification logic 128, and/or filter criterion logic 138 are implemented on a local computer. Further, aspects of the study data analysis system 102 may be implemented in different combinations and implementations than that shown in FIG. 1. For example, functionality of the DBMS engine 130 may be incorporated into the agent identification logic 126, the subset identification logic 128, the filter criterion logic 138, and/or the study data 106. Agent identification logic 126, subset identification logic 128, and/or filter criterion logic 138 may include, for example, fuzzy logic and/or traditional logic steps. Further, many methods of searching databases may be used, including, for example, unsupervised pattern discovery methods, coincidence detection methods, and/or entity relationship modeling.

The study data 106 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
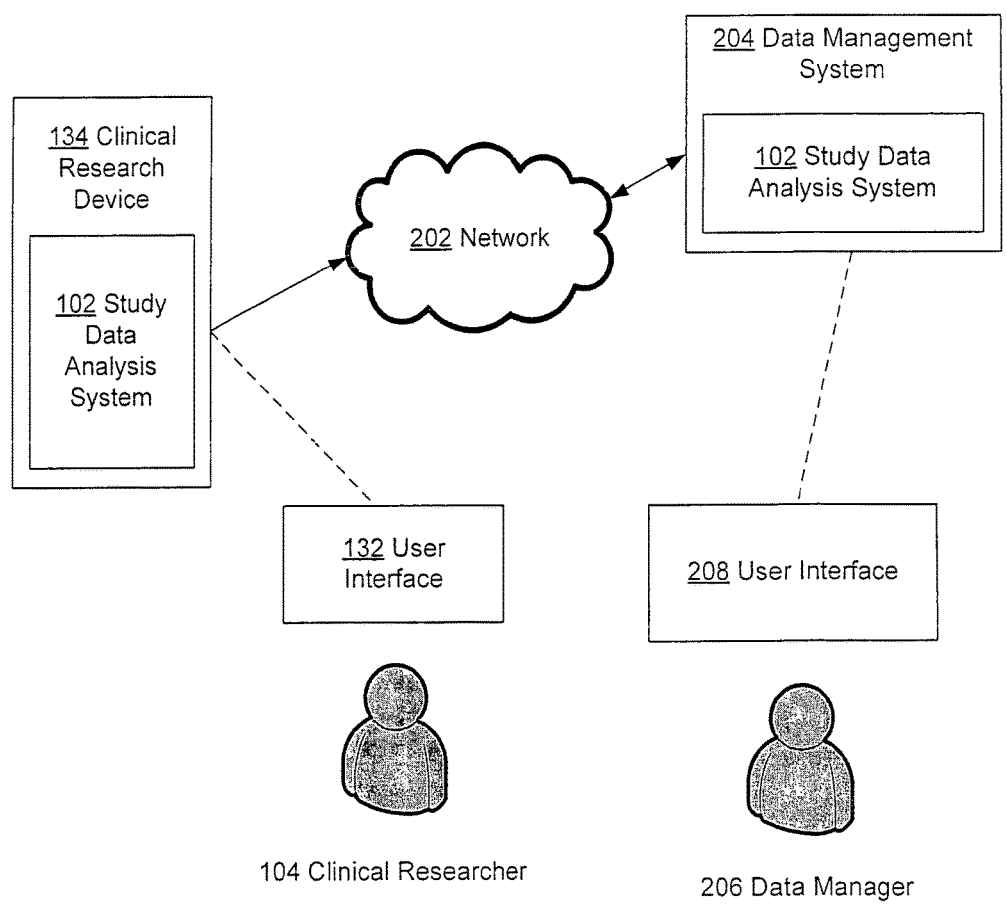
FIG. 2 illustrates certain alternative embodiments of the data analysis system of FIG. 1.

FIG. 2 illustrates certain alternative embodiments of the research system 100 of FIG. 1. In FIG. 2, the clinical researcher 104 uses the user interface 132 to interact with the study data analysis system 110 deployed on the clinical research device 134. The clinical research device 134 may be in communication over a network 202 with a data management system 204, which may be also running the study data analysis system 102, the data management system 204 may be interacted with by a data manager 206 through a user interface 208. Of course, it should be understood that there may be many clinical researchers other than the specifically illustrated clinical researcher 104, each with access to an individual implementation of the study data analysis system 102. Similarly, multiple data management systems 204 may be implemented.

In this way, the clinical researcher 104, who may be operating in the field, e.g., in an office, laboratory and/or hospital environment, may be relieved of a responsibility to update or manage contents in the study data 106, or other aspects of the study data analysis system 102. For example, the data management system 204 may be a centralized system that manages a central database of the study data 106, and/or that deploys or supplies updated information from such a central database to the clinical research device 134.

FIG. 3 illustrates an alternative embodiment of the study data 106 associated with the research system 100 of FIG. 1. In FIG. 3, and in the various examples herein, a particular nomenclature is used for the terms described above and related terms, in order to provide consistency and clarity of description. However, it should be understood that other terminology may be used to refer to the same or similar concepts.

In FIG. 3, agents 302 are stored and organized with respect to a plurality of treatment target study data 304. The treatment target study data 304 include many of the terms and concepts just described, as well as additional, but not exhaustive, terms and concepts that may be relevant to the use and operation of the study data analysis system 109.

For example, the treatment target study data 304 may include study efficacy data 306. Study efficacy data 306 may refer, for example, to data resulting from administration or testing of an agent(s) 302 that relates to an intended effect. For example, study efficacy data 306 may include remission rates following administration of an anti-cancer agent. Study adverse event data 308 may refer, for example, to data resulting from administration or testing of an agent(s) 302 that relates to an unintended effect. Study adverse event data 308 may include, for example, incidence of nausea or bone pain following administration of an anti-cancer agent.

Somewhat analogously, subset efficacy data 310 refers to, for example, data resulting from administration or testing of an agent(s) 302 that relates to an intended effect of the agent(s) in a subpopulation. A subset may include one or more individuals or one or more groups of individuals. Subset efficacy data 310, for example, may include remission rates for females only following administration of an anti-cancer agent. In this example, females are the subset or subpopulation.

Similarly, subset adverse event data 312 refers to, for example, data resulting from administration or testing of an agent(s) 302 that relates to an unintended effect of the agent(s) in a subset or subpopulation. Subset adverse event data 312 may include, for example, elevated blood pressure or decreased interleukin-12 expression following administration of an anti-cancer agent. Subset adverse event data 312, for example, may include incidence of nausea or bone pain for females only following administration of an anti-cancer agent. Accordingly, subset adverse event data 312 may be data characterizing the adverse event itself and/or other data characterizing the subpopulation experiencing the adverse event.

Treatment target study data 304 may also include subpopulation identifier data 314. Subpopulation identifier data 314 may refer, for example, to data that tends to distinguish the subset or subpopulation from other subpopulations or a general population, other than subset adverse event data 312. Subpopulation identifier data 314 for example, may include a genomic DNA sequence that is specific to a subset of data or a subpopulation and which tends to distinguish that subpopulation from other subpopulations or a general population. Subpopulation identifier data 314 may correlate with subset adverse event data 319 and/or further, characterize the subset of data.

In FIG. 3, adverse event data filter 318 is applied by the clinical researcher 104, the study data analysis system 102, and/or the filter criterion logic 138 to select data of a certain character, defined by a specific filter criterion entered by the clinical researcher 104 or contained within the study data analysis system 102, and/or the filter criterion logic 138. Similarly, an efficacy data filter 316 may be applied to treatment target study data 304 by the clinical researcher 104, the study data analysis system 102, and/or the filter criterion logic 138.

Accordingly, the study data analysis system 102 may be used to applying at least one filter criterion to the at least one dataset to identify a subset of the at least one dataset, the subset of the at least one dataset associated with a defined level of at least one adverse event associated with administration of the at least one agent.

In an alternative embodiment, subset adverse event data 312 may be used as a parameter for use in searching one or more biomedical databases to identify subpopulation identifier data 314 that correlate with the subset adverse event data 312. Such subpopulation identifier data 314 may indicate clinically relevant subpopulation(s) for the agent of interest. For example, using the study data analysis system 102 and/or agent identifier logic 126 and/or subpopulation identifier logic 128 and/or filter criterion logic 138, an agent may be identified that is acceptably effective and safe in a subset or subpopulation characterized by, for example, a specific haplotype profile. That specific haplotype profile may then be used as a search parameter to search biomedical databases for prospective patient populations that display the specific haplotype profile, e.g., individuals with primarily Mediterranean ancestry. The study data analysis system 102 and/or agent identifier logic 126 and/or subpopulation identifier logic 128 may perform this analysis. The subsequently-identified prospective patient population (e.g., individuals with primarily Mediterranean ancestry) is thus a candidate for further testing as a potentially viable population that could benefit from the identified agent 302 with an acceptable incidence of adverse events.

Many other examples of relationships and associations between the various treatment target study data 304 and/or the agent(s) 302 may be defined or determined and stored in the study data 106 according to the agent identification logic 126, the subset identification logic 128, and/or the filter criterion logic 138. Certain of these examples are provided herein.

Additionally, although the study data 106 is illustrated conceptually in FIG. 3 as a flat table in which one or more of the selected agents 302 are associated with one or more of the treatment target study data 304, it should be understood that this illustration is for explanation and example only, and is not intended to be limiting in any way with respect to the various ways in which the study data 106 may be stored, organized, accessed, filtered, processed, recalled, or otherwise used.

For example, the study data 106 may be organized into one or more relational databases. In this case, for example, the study data 106 may be stored in one or more tables, and the tables may be joined and/or cross-referenced in order to allow efficient access to the information contained therein. Thus, the agent(s) 302 may define a record of the database(s) that are associated with various ones of the treatment target study data 304.

In such cases, the various tables may be normalized so as, for example, to reduce or eliminate data anomalies. For example, the tables may be normalized to avoid update anomalies (in which the same information would need to be changed in multiple records, and which may be particularly problematic when database 136 is large), deletion anomalies (in which deletion of a desired field or datum necessarily but undesirably results in deletion of a related datum), and/or insertion anomalies (in which insertion of a row in a table creates an inconsistency with another row(s)). During normalization, an overall schema of the database 136 may be analyzed to determine issues such as, for example, the various anomalies just referenced, and then the schema is decomposed into smaller, related schemas that do not have such anomalies or other faults. Such normalization processes may be dependent on, for example, desired schema(s) or relations between the agent(s) 302 and/or treatment target study data 304, and/or on desired uses of the study data 106.

Uniqueness of any one record in a relational database holding the study data 106 may be ensured by providing or selecting a column of each table that has a unique value within the relational database as a whole. Such unique values may be known as primary keys. These primary keys serve not only as the basis for ensuring uniqueness of each row (e.g., agent) in the database, but also as the basis for relating or associating the various tables within one another. In the latter regard, when a field in one of the relational tables matches a primary key in another relational table, then the field may be referred to a foreign key, and such a foreign key may be used to match, join, or otherwise associate (aspects of) the two or more related tables.

FIG. 3 and associated potential relational databases represent only one example of how the study data may be stored, organized, accessed, recalled, or otherwise used.

Figure 4:
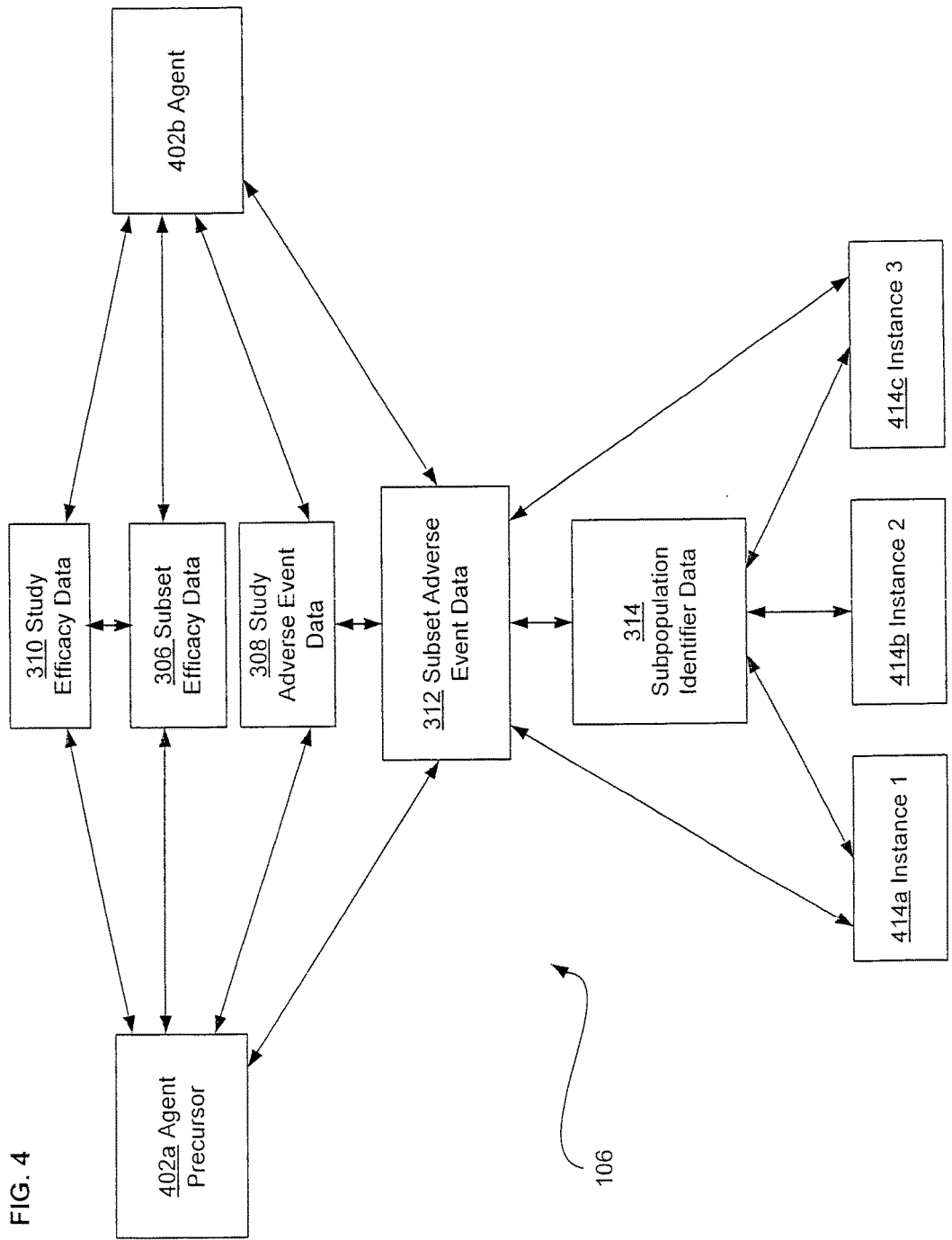
FIG. 4 illustrates another alternative embodiment of study data associated with the data analysis system of FIG. 1.

FIG. 4 illustrates another alternative embodiment of study data 106 associated with the research system 100 of FIG. 1, in which the study data 106 is conceptually illustrated as being stored in an object-oriented database.

In such an object-oriented database, the various agent(s) 302 and/or treatment target study data 304 may be related to one another using, for example, links or pointers to one another. FIG. 4 illustrates a conceptualization of such a database structure in which the various types of study data are interconnected, and is not necessarily intended to represent an actual implementation of an organization of the study data 106.

The concepts described above may be implemented in the context of the object-oriented database of FIG. 4. For example, two instances 302a and 302b of the agent 302 may be associated with study efficacy data 306 and study adverse event data 308. An agent(s) 302 or instance of one or more agent(s) 302 that exhibits a desired level of efficacy and a defined level of tolerance for one or more adverse events may be associated with one or more subpopulations characterized by subset adverse event data 312. For example, agent 402b may be associated with subset adverse event data 312 indicating an acceptable adverse event profile.

Similarly, subset adverse event data 312 may be associated with subpopulation identifier data 314. For example, subset adverse event data 312 associated with agent 402b may be associated with subpopulation identifier data 314. Further, three instances of subpopulation identifier data, for example instance 1 (414a), instance 2 (414b), and instance 3 (414c), may be associated with the subpopulation identifier data 314 and/or the subset adverse event data 312.

Also, other data may be included in the study data 106. For example, in FIG. 4, an agent precursor 402a is shown that refers generally to an agent used to facilitate application of the agent 402b, e.g., a substance that when metabolized becomes agent 402, for example a prodrug.

Many other examples of databases and database structures also may be used. Other such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

As referenced herein, the study data analysis system 102 and/or agent identification logic 126 and/or subset identification logic 128 and/or filter criterion logic 138 may be used to perform various data querying and/or recall techniques with respect to the study data 106, in order to facilitate identification of a suitable agent 302. For example, where the study data 106 is organized, keyed to, and/or otherwise accessible using one or more of the agents 302 and/or treatment target study data 304, various Boolean, statistical, and/or semi-boolean searching techniques may be performed.

For example, SQL or SQL-like operations over one or more of the agents 302/treatment target study data 304 may be performed, or Boolean operations using the agents 302/treatment target study data 304 may be performed. For example, weighted Boolean operations may be performed in which different weights or priorities are assigned to one or more of the agents 302/treatment target study data 304, perhaps relative to one another. For example, a number-weighted, exclusive-OR operation may be performed to request specific weighting of desired (or undesired) study data to be included (excluded).

The clinical researcher 104 may input arthritis pain as the treatment target in search of an agent 302, with the goal of identifying agents that are associated with examples of study adverse event data 308 that belong to a particular class, for example, neurological, gastrointestinal, and/or cardiovascular adverse events. For example, the clinical researcher 104 may want to identify agents 302 that may be effective in relieving arthritis pain, but for which cardiovascular adverse events are unacceptable. Having identified a set of agents meeting these criteria, the clinical, researcher 104 could then use the study data analysis system 102 to apply a filter criterion to a relevant dataset to identify subset adverse event data 312 exhibiting acceptable levels of cardiovascular adverse events. In another example, the clinical researcher may be willing to tolerate lower levels of efficacy with the intention that more and/or different subpopulations may be identified for which an agent exhibits acceptable cardiovascular adverse events. In such a case, the effectiveness of the agent may require supplementation, for example by combination with other agents.

As another example, the clinical researcher 104 may start with a preferred subpopulation, characterized by either subpopulation identifier data 314 or subset adverse event data 312, and proceed to identify agents that are safe at a defined level and optionally effective at a defined level for that subset or subpopulation.

The clinical researcher 104 may specify such factors, including, filter criteria, using, for example, the user interface 132. For example, the clinical researcher 104 may designate one or more of the agents 302/treatment target study data 304, and assign a weight or importance thereto, using, for example, a provided ranking system. In this regard, and as referenced herein, it should be understood that the clinical researcher 104 may wish to deliver a particular instance of an agent 302, e.g., a particular chemotherapeutic to be delivered to a tumor. However, such an otherwise effective agent, if applied by conventional techniques, may present an unacceptable level of nausea and/or pain following administration. Moreover, the clinical researcher 104 may not be aware of a subpopulation of prospective patients that may tolerate the agent better than previously-examined population(s). However, the clinical researcher 104 may query the study data analysis system 102 based on the desired agent 302, and may thereby discover one or more subpopulations in which the agent may be applied without unacceptable adverse events. The clinical researcher 104 may further query the study data analysis system 102 based on the subset adverse event data 312 to elicit subpopulation identifier data 314 that describe one or more clinically relevant prospective patient subpopulations.

Similarly, data analysis techniques (e.g., data searching) may be performed using the study data 106, perhaps over a large number of databases. For example, the clinical researcher 104 may input a treatment target of interest in search of an agent, i.e., an agent for which the incidence of specific adverse events under the existing standard of care is high and/or unacceptable. Then, the clinical researcher would receive a listing of agents that are ranked according to some input criteria. For example, the clinical researcher 104 may receive a listing of instances of agents 302, ordered by efficacy, incidence of a particular adverse event in a tested general population, and incidence of a particular adverse event in a tested subpopulation. In this way, for example, if a set of agents 302 is effective according to an efficacy filter criterion of the clinical researcher 104, then the clinical researcher 104 may select an agent 302 according to acceptable incidence of adverse event(s) according to an adverse event filter criterion, even if some relative sacrifice of efficacy is associated with such a selection.

By way of further example, other parameters/characteristics may be factored in. For example, elimination pathways may be tracked, databased, and/or weighted for use in the study data 106 and/or the study data analysis system 102. For example, if a particular agent 302 is easily eliminated by the liver, then in a case where a subset or subpopulation is identified that is characterized by compromised liver function, such an agent may be selected by the clinical researcher 104, even if an otherwise more effective agent 302 is known. Algorithms implementing such query/recall/access/searching techniques may thus use Boolean or other techniques to output, for example, a thresholded, rank-ordered list. The agent identification logic 126 and/or subset identification logic 128 and/or filter criterion logic 138 may then assign a key or other identifier to such a list(s), for easier use thereof the next time a like query is performed.

Design and testing of querying techniques in particular implementations of the study data analysis system 102 may involve, for example, entry of candidate agents 302/treatment target study data 304 (or instances thereof) into a database(s), along with associated test results and/or affinity metrics that may be used to determine/weight targets or sets of targets. Then, an identifier may be generated that is unique to the treatment target set(s).

FIG. 5 illustrates another alternative embodiment of study data associated with the research system 100 of FIG. 1, with specific examples of study data. In particular, FIG. 5 provides or refers to example results from a related technical paper, which is specifically referenced below.

For example, the first and second rows of the table of FIG. 5 (i.e., rows 502 and 504, respectively) refer to examples that may be found in Niyikiza et al., "Homocysteine and Methylmalonic Acid: Markers to Predict and Avoid Toxicity from Pemetrexed Therapy," Mol. Canc. Ther., vol. 1, pp. 545-552 (May 2002), which is hereby incorporated by reference in its entirety, and which may be referred to herein as the Niyikiza reference.

In the Niyikiza reference, data are reported for various treatment populations, characterized by a number of measured clinical parameters, which provide a basis for correlating) an adverse event frequency or odds ratio with a predictive factor for severe toxicity in a patient populations for a specific agent in the treatment of specific medical conditions.

The Niyikiza reference, for example, reports data showing that the toxicity of the agent pemetrexed, a multi-targeted antifolate treatment for various cancers, correlates with high levels of homocysteine and methylmalonic acid, which are indicative of deficient levels of folic acid and vitamin B12. Inside a cell, pemetrexed is rapidly metabolized into active polyglutamate forms that are potent inhibitors of several tetrahydrofolate co-factor requiring enzymes critical to the synthesis of purines and thymidine. Functionally, pemetrexed acts as a prodrug for its intracellular polyglutamate forms.

Rows 502 and 504 represent fields of data reported for pemetrexed (trade name "ALIMTA®"). The Niyikiza reference examined data from studies of pemetrexed administration to 246 patients treated between 1995 and 1999. Multivariate stepwise regression methods were used to identify markers predictive of severe toxicity. An odds ratio approach was used to correlate a potential predictive marker with a risk of developing severe toxicity. As shown in rows 502 and 504, an odds ratio of 1 correlates with study adverse event data 308 from the overall study population. The Niyikiza reference reports subset adverse event data 312 that, for a subpopulation in which methylmalonic acid levels are less than 119.0 nmol/l, the odds ratio of developing severe toxicity is 0.3. Similarly, a subpopulation with total homocysteine levels of less than 7.5 μmol/l had an odds ratio of developing severe toxicity of 0.7. This subset adverse event data 312 was further correlated with subpopulation identifier data 314 indicating that patients supplemented with folic acid and vitamin B12 would likely exhibit the desired subset adverse event data 312. The Niyikiza reference also reports subset efficacy data 310 that members of the identified subpopulation had maintained or improved efficacy following administration of pemetrexed.

The Niyikiza reference did not use a filter criterion as claimed herein. However, a filter criterion specifying an odds ratio of less than 0.8 of developing severe toxicity would have identified, as a subset of the overall dataset, the group of patients with methylmalonic acid levels <119.0 nmol/l and/or the group of patients with total homocysteine levels <7.5 μmol/l (see FIG. 5).

FIG. 6 illustrates another alternative embodiment of study data associated with the research system 100 of FIG. 1, with specific examples of study data. In particular, FIG. 6 provides or refers to example results from a related technical paper, which is specifically referenced below.

For example, the first through third rows of the table of FIG. 6 (i.e., rows 602, 604, and 606, respectively) refer to examples that may be found in Vogelzang et al., "Phase III Study of Pemetrexed in Combination With Cisplatin Versus Cisplatin Alone in Patients With Malignant Pleural Mesothelioma," J. Clin. Oncol., vol. 21:14, pp. 2636-44 (Jul. 15, 2003), which is hereby incorporated by reference in its entirety, and which may be referred to herein as the Vogelzang reference.

In the Vogelzang reference, data are reported for various treatment populations which provide a basis for correlating an agent with a predictive factor for severe toxicity in a patient population. The Vogelzang reference, for example, reports data showing that a subpopulation supplemented with folic acid and vitamin B12 experiences less toxicity following administration of pemetrexed, based on the hypothesis developed in the Niyikiza reference that the agent may have particularly detrimental effects in patients with high levels of homocysteine and methylmalonic acid, which are indicative of deficient levels of folic acid and/or vitamin B12.

Rows 602, 604 and 606 contain study data from the Vogelzang reference, showing study data from a phase III clinical trial comparing efficacy and adverse events following administration of pemetrexed plus cisplatin for malignant pleural mesothelioma versus administration of cisplatin alone. Study efficacy data 306 from the intent to treat group showed a significant benefit in efficacy with the combination therapy. Subset efficacy data 310 from the group that was fully supplemented with folic acid and vitamin B12 showed a significant benefit in efficacy with the combination therapy, similar to that of study efficacy data 306.

Subset adverse event data 312 from the Vogelzang reference for three different parameters are also shown in rows 602, 604 and 606, respectively. The subset adverse event data 312 in row 602 is a reported 23.2% grade ¾ neutropenia for the group that was given full supplementation with folic acid and vitamin B12. This is down from 41.4% grade ¾ neutropenia in the group that was partially or never supplemented with folic acid and vitamin B12.

The subset adverse event data 312 in row 604 is a reported 11.9% nausea for the group that was given full and partial supplementation with folic acid and vitamin B12. This is down from 31.3% nausea in the group that was never supplemented with folic acid and vitamin B12.

The subset adverse event data 312 in row 606 is a reported 10.3% vomiting for the group that was given full and partial supplementation with folic acid and vitamin B12. This is down from 31.3% vomiting in the group that was never supplemented with folic acid and vitamin B12.

Thus, many parameters may be screened as subset adverse event data 312 for a given agent. Moreover, the Vogelzang reference also describes the three subpopulations identified by subset adverse event data 312 in terms of populations that are supplemented with folic acid and vitamin B12 (i.e., subpopulation identifier data 314 in rows 602, 604 and 606).

As described above, the Vogelzang reference did not use a filter criterion as claimed herein. However, a filter criterion that, for example, removed subjects experiencing, for example, vomiting, would have identified, as a subset of the dataset, predominantly patients in the full and partial supplementation group (see FIG. 6, row 606).

FIG. 7 illustrates hypothetical alternative embodiments of study data associated with the research system 100 of FIG. 1, with specific examples of study data. In particular, FIG. 7 provides or refers to an example from a related technical paper, which is specifically referenced below.

For example, FIG. 7 refers to examples that may be found in Lamba et al., "Hepatic CYP2B6 Expression: Gender and Ethnic Differences and Relationship to CYP2B6 Genotype and CAR (Constitutive Androstane Receptor) Expression," J. Pharm. Exp. Ther., vol. 307:3, pp. 906-22 (December, 2003), which is hereby incorporated by reference in its entirety, and which may be referred to herein as the Lamba reference.

Various forms of the liver enzyme cytochrome p450 function to metabolize agents in the bloodstream, including many clinically important medications. The Lamba reference reports that the liver enzyme cytochrome p450 2B6 ("CYP2B6") activity was 3.6- and 5.0-fold higher in Hispanic females than in Caucasian (P<0.022) or African-American females (P<0.038). In the Lamba reference, this difference was correlated with single nucleotide polymorphisms ("SNP's"). CYP2B6 is the main enzyme involved in the bioactivation of ifosfamide. Therefore, the effectiveness of ifosfamide may be higher in females (especially Hispanic females) than in males, who generally exhibit a lower CYP2B6 activity than females.

As a hypothetical example, one of the commonly reported adverse events for ifosfamide, an anticancer agent, is darkened and thickened skin. A clinical researcher 104 could input into the study data analysis system 102 cancer as the at least one treatment target in search of an agent. The study data analysis system 102 could then access one or more datasets from studies using ifosfamide to treat cancer.

As shown in row 702 of FIG. 7, the study data analysis system 102 could identify ifosfamide as an agent that results in acceptable efficacy for treating cancer, as described by study efficacy data 306. The study data analysis system 102 could also find data relating to incidence of darkened and thickened skin following ifosfamide administration, as described by study adverse event data 308. The study data analysis system 102 or the clinical researcher 104 could then apply a filter criterion to the dataset to identify a subset of the individuals experiencing darkened and thickened skin following ifosfamide administration. Such a filter criterion could be individuals experiencing little or no darkened and thickened skin following ifosfamide administration. It should be noted that the Lamba reference does not disclose the application of such a filter criterion to effect the identification of a subset of the dataset.

As a further example, the study data analysis system 102, applying the filter criterion requiring, little or no darkened and thickened skill following ifosfamide administration, could identify a CYP2B6 subset or subpopulation that is characterized by a specific SNP profile and that experiences little or no darkened and thickened skill following ifosfamide administration, as described by subset adverse event data 312. Such a subpopulation could also exhibit, for example, at least maintained efficacy following administration of ifosfamide, as described by subset efficacy data 310. Further, the specific SNP CYP2B6 subpopulation may correlate, for example, with Hispanic women between the ages of 20 and 45, as described by subpopulation identifier data 314. It should be noted that the Lamba reference does not disclose the above relationship between study adverse events and CYP2B6 SNP profile, nor a relationship between ethnicity and age. The discussion above regarding the Lamba reference is purely hypothetical and is included merely for illustration purposes.

As another hypothetical example, row 704 of FIG. 7 illustrates an example from McDowell. et al., "Systematic review and meta-analysis of ethnic differences in risks of adverse reactions to drugs used in cardiovascular medicine," Brit. Med. J., vol. 332, pp. 1177-81 (May 5, 2006), which is incorporated by reference in its entirety and which is referred to herein as the McDowell reference.

The McDowell reference analyzed various studies that included at least two ethnic groups and one or more adverse events following administration of cardiovascular medications. Relative risk of an adverse event was calculated for each ethnicity to identify subpopulations at increased risk for an adverse event. Row 704 of FIG. 7 illustrates one example from the McDowell reference in which relative risk of angio-edema following ACE inhibitor administration is the study adverse event data 308, in this case 1 for the combined study population. The subset adverse event data 312 is described in terms of an increased relative risk for angio-edema, in this case 3 for the subpopulation of Black patients. Although not discussed in the McDowell reference, by implication, non-black patients should exhibit a reciprocal, decreased risk for angio-edema.

As a further hypothetical, an analysis of subset adverse event data 312 by the study data analysis system 102 may result in subpopulation identifier data 314 that further characterizes the subpopulation. For example, an association between the haplotype of the identified Black subpopulation and, for example, the haplotype of individuals of West Indian descent may be identified by the study data analysis system 102 as subpopulation identifier data 314. It should be noted that the McDowell reference does not disclose the above relationship between the haplotype of the identified Black subpopulation and the haplotype of individuals of West Indian descent. The discussion above on this topic is purely hypothetical and is included merely for illustration purposes.

The McDowell reference does not apply a filter criterion to the study datasets, rather the McDowell reference identifies relative risks for various subsets. To apply a filter criterion in such a case, the study data analysis system 102 could exclude, for example, study adverse event data 308 with angio-edema values above a specified level from the dataset in performing the function of applying at least one filter criterion to the at least one dataset to identify a subset of the at least one dataset, the subset of the at least one dataset associated with a defined level of at least one adverse event associated with administration of the at least one agent.

Figure 8:
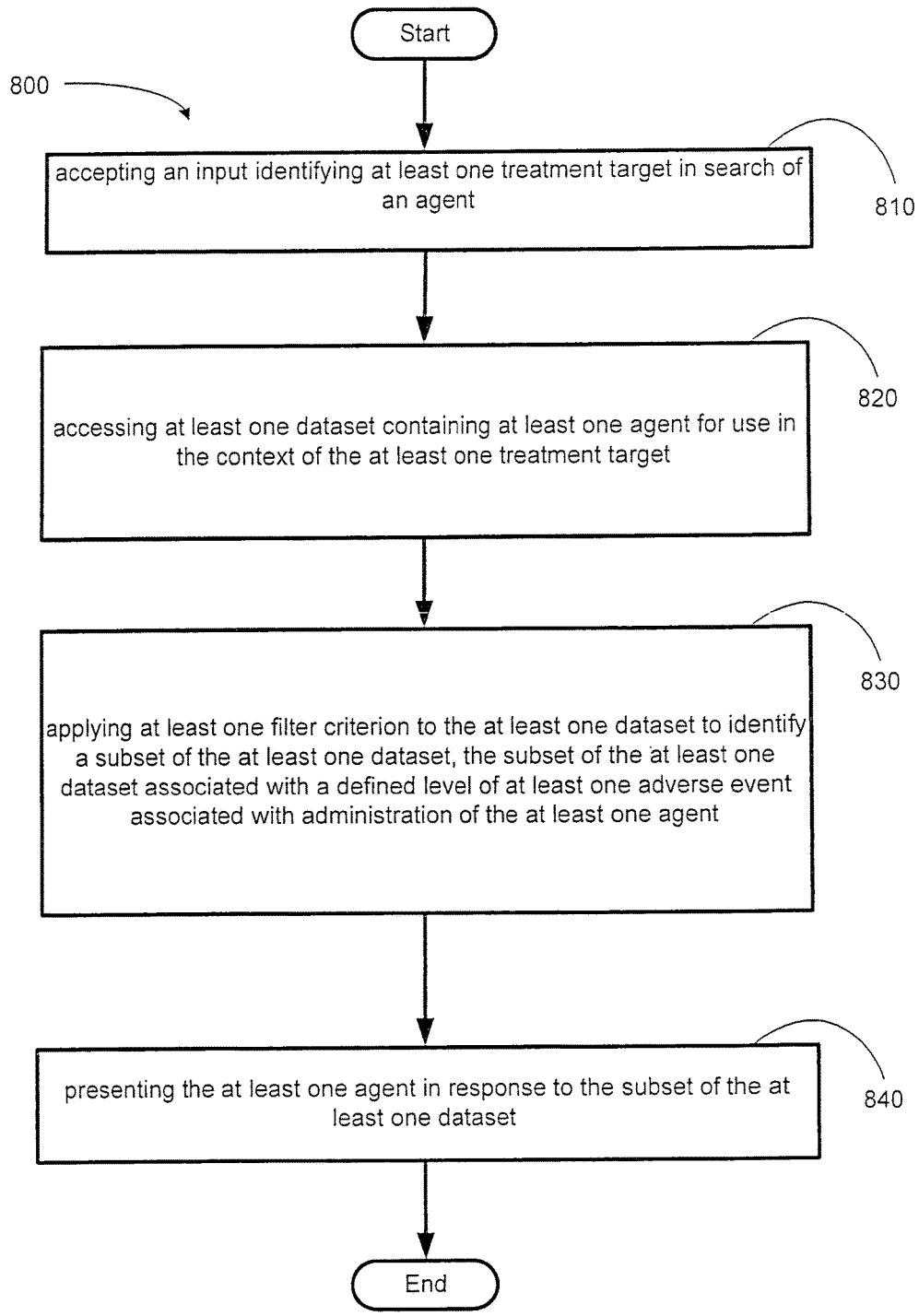
FIG. 8 illustrates an operational flow representing example operations related to computational systems for biomedical data.

FIG. 8 illustrates an operational flow 800 representing example operations related to computational systems for biomedical data. In FIG. 8 and in following figures that include various examples of operational flows, discussion, and explanation may be provided with respect to the above-described examples of FIGS. 1-7, and/or with respect to other examples and contexts. However, it should be understood that the operational flows may be executed in a number of other environment and contexts, and/or in modified versions of FIGS. 1-7. Also, although the various operational flows are presented in the sequence(s) illustrated, it should be understood that the various operations may be performed in other orders than those which are illustrated, or may be performed concurrently.

After a start operation, operation 810 shows accepting an input identifying at least one treatment target in search of an agent. The input may be accepted through a user interface 132 from a clinical researcher 104.

For example, the agent identification logic 126 of the study data analysis system 102 may receive a designation of at least one medical condition for which the incidence of a specific adverse event(s) under the existing standard of care is high and/or unacceptable, such as, for example, one or more medical indications for vehicle study adverse event data 308 is available. More specifically, this could be a defined medical indication such as, for example, colon cancer, or a cosmetic treatment target such as, for example, reducing wrinkles in the skin.

Operation 820 depicts accessing at least one dataset containing at least one agent for use in the context of the at least one treatment target. For example, the assent identification logic 126 of the study data analysis system 102 may identify within a clinical trial database the anti-cancer agent pemetrexed as having, at least a 40% partial response rate in treating, cancer.

Operation 830 depicts applying at least one filter criterion to the at least one dataset to identify a subset of the at least one dataset, the subset of the at least one dataset associated with a defined level of at least one adverse event associated with administration of the at least one agent. For example, the subset identification logic 128 and/or the filter criterion logic 138 of the study data analysis system 102 may identify within a clinical trial database a subset or subpopulation exhibiting a decreased incidence of the adverse event neutropenia and maintained efficacy in treating cancer, following administration of pemetrexed. That subpopulation may be, for example, a set of patients supplemented with folic acid and vitamin B12 prior to treatment with pemetrexed. The identification may be achieved by applying a filter criterion to, for example, a clinical study dataset. In such an example, filter criterion logic 138 may remove from the analysis adverse event data 308 that represents, for example neutropenia above 20%. Thus, a subset of clinical study data would be identified for which incidence of the adverse event, neutropenia in this example, is less than 20%.

Operation 840 illustrates presenting the at least one agent in response to the subset of the at least one dataset. For example, the study data analysis system 102 may present an identified agent such as pemetrexed to a clinical researcher 104 via a user interface 132. Optionally, the identified agent(s) and/or identified subpopulation(s) are then assigned to at least one memory. For example, the identified agent(s) and/or identified subpopulation(s) may be assigned to one or more of the various (types of) databases referenced above, such as the relational and/or object-oriented database(s), or to another type of memory, not explicitly mentioned.

In this regard, it should be understood that the identification(s) may first be encoded and/or represented in digital form (i.e., as digital data), prior to the assignment to the at least one memory. For example, a digitally-encoded representation of the identification(s) may be stored in a local memory, or may be transmitted for storage in a remote memory.

Thus, an operation may be performed related either to a local or remote storage of the digital data, or to another type of transmission of the digital data. Of course, as discussed herein, operations also may be performed related to accessing, querying, processing, recalling, or otherwise obtaining the digital data from a memory, including, for example, receiving a transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

Figure 9:
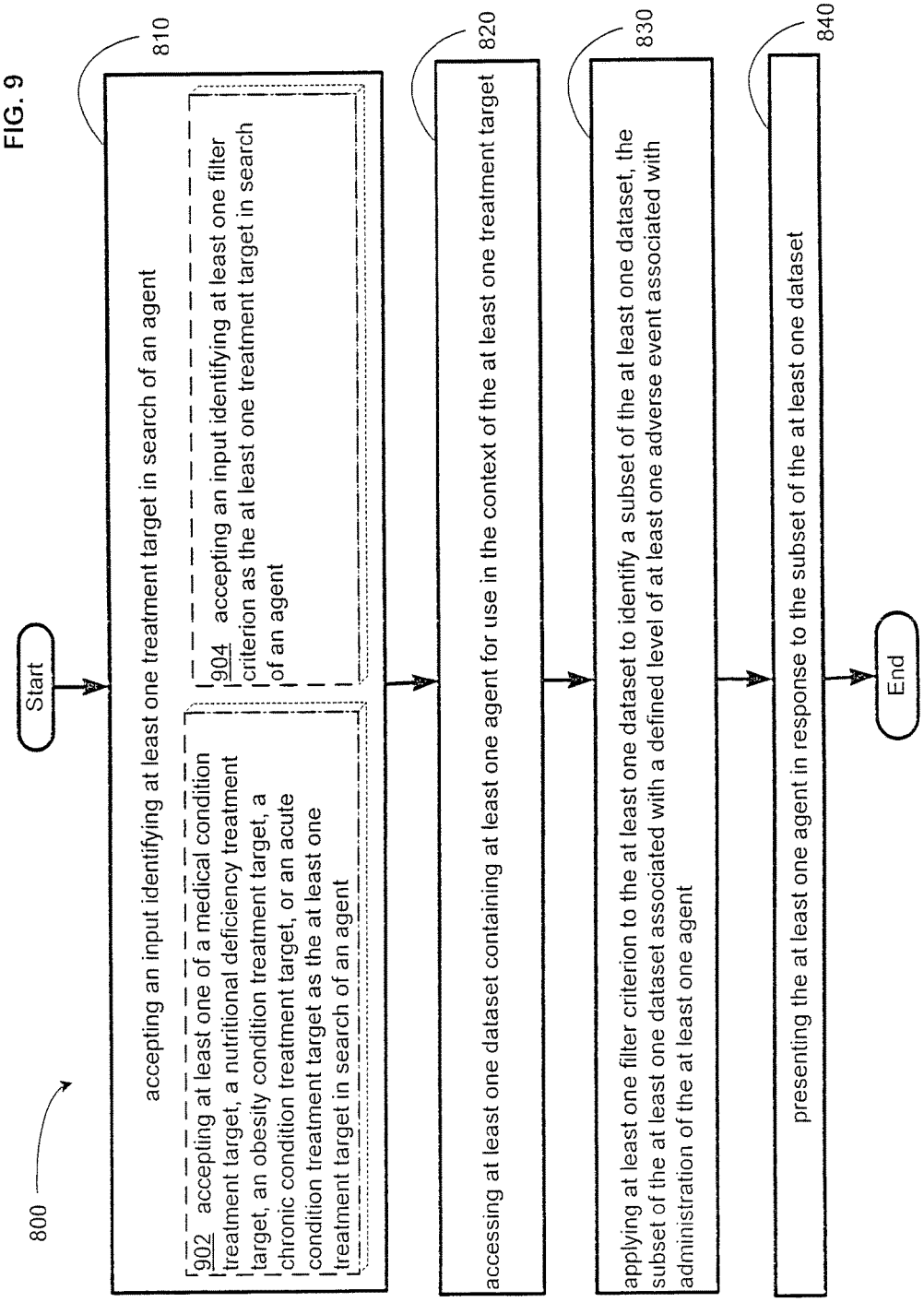
FIG. 9 illustrates an alternative embodiment of the example operational flow of FIG. 8.

FIG. 9 illustrates alternative embodiments of the example operational flow 800 of FIG. 8. FIG. 9 illustrates example embodiments where the accepting operation 810 may include at least one additional operation. Additional operations may include operation 902 and/or operation 904.

Operation 902 depicts accepting at least one of a medical condition treatment target, a nutritional deficiency treatment target, an obesity condition treatment target, a chronic condition treatment target, or an acute condition treatment target as the at least one treatment target in search of an agent. For example, as referenced herein, the study data analysis system 102 may accept via the user interface 132, for example, a condition that persists over weeks, months or years as the at least one chronic condition treatment target. The study data analysis system 102 may accept, for example, Acquired Immune Deficiency Syndrome (AIDS) as the at least one chronic condition treatment target.

Operation 904 depicts accepting an input identifying at least one filter criterion as the at least one treatment target in search of an agent. For example, the study data analysis system 102 may accept via the user interface 132, for example, diabetes associated with a mean fasting blood sugar level of 150 mg/dl or higher as the at least one treatment target in search of an agent.

Figure 10:
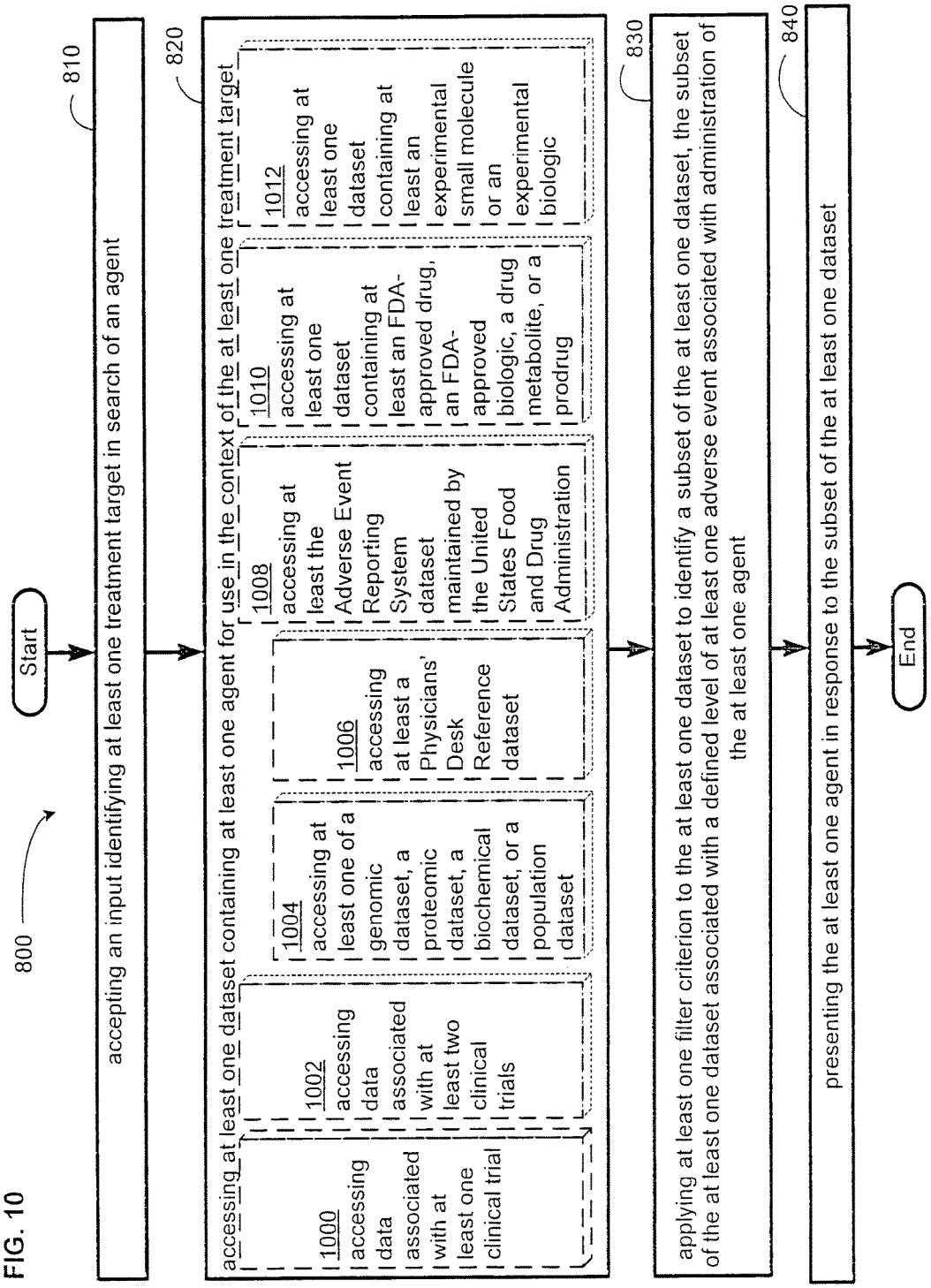
FIG. 10 illustrates an alternative embodiment of the example operational flow of FIG. 8.

FIG. 10 illustrates alternative embodiments of the example operational flow 800 of FIG. 8. FIG. 10 illustrates example embodiments where the accessing operation 820 may include at least one additional operation. Additional operations may include operation 1000, 1002, operation 1004, operation 1006, operation 1008, operation 1010, and/or operation 1012.

Operation 1000 depicts accessing data associated with at least one clinical trial. For example, study data is shown in rows 602, 604 and 606 of FIG. 6 for pemetrexed combination therapy versus cisplatin alone, in the treatment of malignant pleural mesothelioma. These data were reported in the Vogelzang reference. A clinical trial conducted by Eli Lilly and Company entitled "A Single-blind Randomized Phase 3 Trial of ALIMTA® (pemetrexed) plus Cisplatin versus Cisplatin Alone in Patients with Malignant Pleural Mesothelioma" generated the data described in FIG. 6, rows 602, 604 and 606. Accordingly, the study data analysis system 102 and/or the agent identification logic 126 and/or subset identification logic 128 and/or filter criterion logic 138 may access data associated with at least one clinical trial.

Operation 1002 depicts accessing data associated with at least two clinical trials. For example, as shown in row 704 of FIG. 7, study data from more than one set of study data may be used to identify at least one agent having a defined level of efficacy in treating the at least one medical condition. Specifically, for example, the data in row 704 of FIG. 7 are pooled from five studies using a fixed effects model, as reported by the authors of the McDowell reference. Accordingly, the study data analysis system 102 and/or the agent identification logic 126 and/or subset identification logic 128 and/or filter criterion logic 138 may combine study data from two or more sets of study data in accessing at least one dataset containing at least one agent for use in the context of the at least one treatment target.

Operation 1004 depicts accessing at least one of a genomic dataset, a proteomic dataset, a biochemical dataset, or a population dataset. For example, the study data analysis system 102 and/or the agent identification logic 126 and/or subset identification logic 128 and/or filter criterion logic 138 may access study data that describe the genomic characteristics of a group of subjects. More specifically, the agent identification logic 126 may access a genomic dataset containing information about patient haplotype profiles or virus genomic sequence associated with the administration of a particular combination therapy for HIV.

Operation 1006 shows accessing at least a Physicians' Desk Reference dataset. For example, the study data analysis system 102 and/or the agent identification logic 126 and/or subset identification logic 128 and/or filter criterion logic 138 may access the PDR health clinical trials database to locate study data relating to, for example, drugs effective in treating stomach ulcer and adverse events associated with the drugs.

Operation 1008 shows accessing at least the Adverse Event Reporting System (AERS) database maintained by the United States Food and Drug Administration (FDA). For example, the study data analysis system 102 and/or the agent identification logic 126 and/or subset identification logic 128 and/or filter criterion logic 138 may access the AERS maintained by the FDA. As discussed above, the AERS database contains adverse drug reaction reports from manufacturers as required by FDA regulation.

Operation 1010 shows accessing at least one dataset containing at least an FDA-approved drug, an FDA-approved biologic, a drug metabolite, or a prodrug. For example, the study data analysis system 102 and/or the agent identification logic 126 and/or subset identification logic 128 and/or filter criterion logic 138 may access the AERS database, which contains FDA-approved drugs. More specifically, for example, accessing the AERS database for "diabetic neuropathy" results in, inter alia, the identification of Lyrica® and Cymbalta® as two agents that are FDA-approved in the context of diabetic neuropathy.

Operation 1012 shows accessing at least one dataset containing at least an experimental small molecule or an experimental biologic. For example, the study data analysis system 102 and/or the agent identification logic 126 and/or subset identification logic 128 and/or filter criterion logic 138 may access the database to find information about using curcumin, an experimental small molecule. to treat Alzheimer's disease.

Figure 11E:
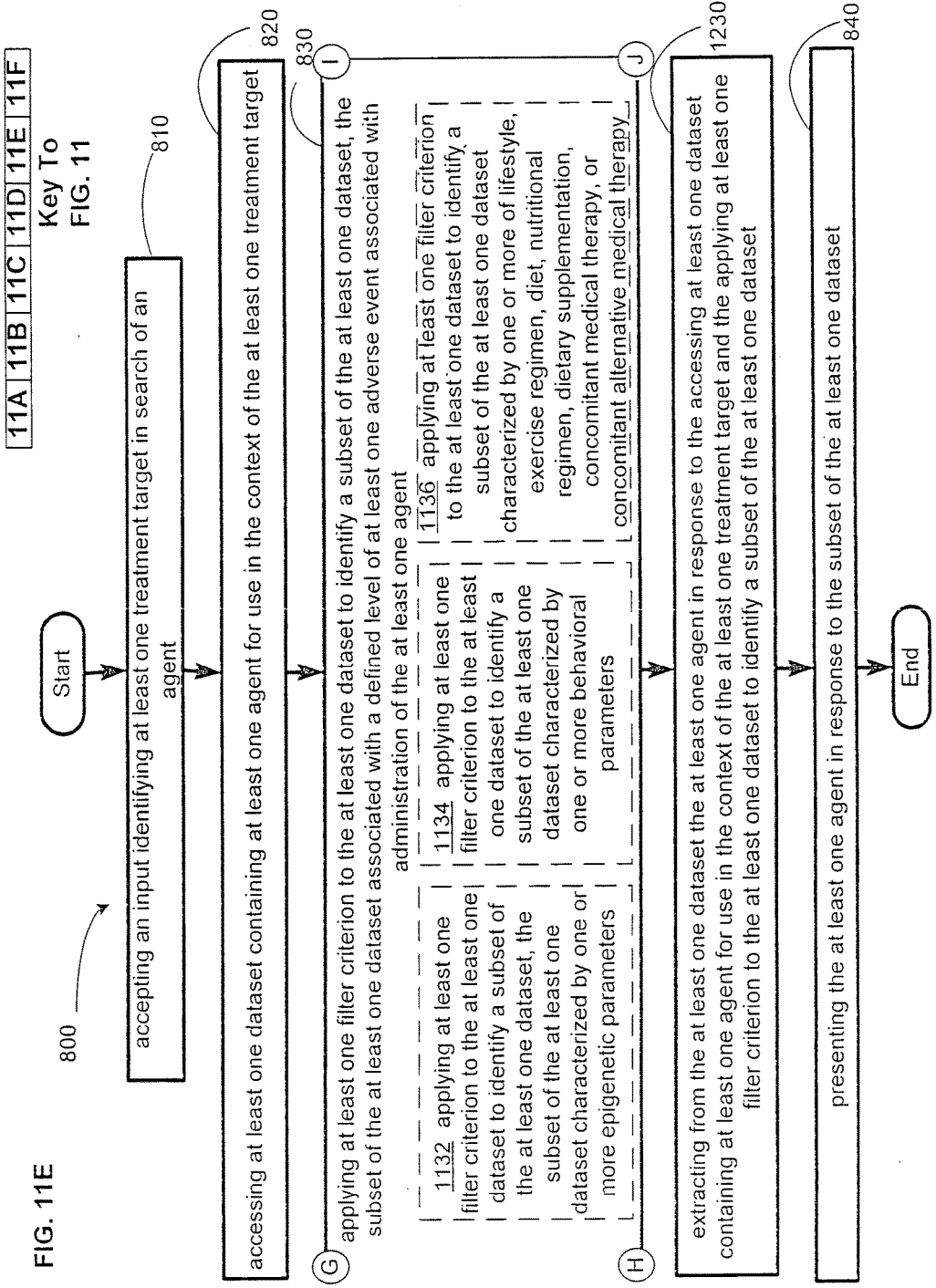
FIG. 11 illustrates an alternative embodiment of the example operational flow of FIG. 8.

FIG. 11 illustrates alternative embodiments of the example operational flow 800 of FIG. 8. FIG. 11 illustrates example embodiments where the defining operation 830 many include at least one additional operation. Additional operations may include operation 1102, operation 1104, operation 1106, operation 1108, operation 1110, operation 1112, operation 1114, operation 1116, operation 1118, operation 1120, operation 1122, operation 1124, operation 1126, operation 1128, and operation 1130.

Operation 1102 shows applying at least a quantitative limit on one or more adverse events. For example, the study data analysis system 102 and/or the agent identification logic 126 and/or subset identification logic 128 and/or filter criterion logic 138 may apply a filter criterion that specifies a numerical limit to an adverse event in a dataset. More specifically, for example, a 20% limit for the incidence of neutropenia could be used as the filter criterion such that a subset of data corresponding to 20% or less neutropenia would be selected from the at least one dataset as the subset of the at least one dataset.

Operation 1104 shows applying at least a qualitative limit on one or more adverse events. For example, the study data analysis system 102 and/or the agent identification logic 126 and/or subset identification logic 128 and/or filter criterion logic 138 may apply a filter criterion that specifies a limit to an adverse event in a dataset that is described in words. More specifically, for example, a description of "tolerable pain" could be used as the filter criterion such that the subset of data corresponding to a description of tolerable pain or words to that effect from individuals to whom an agent was administered would be selected from the at least one dataset as the subset of the at least one dataset. In this instance, data corresponding to descriptions of intolerable pain or words to that effect would be excluded (i.e., filtered out) from the subset of the at least one dataset.

Operation 1106 shows applying at least a statistical adverse event limit. For example, the study data analysis system 102 and/or the agent identification logic 126 and/or subset identification logic 128 and/or filter criterion logic 138 may apply a filter criterion that specifies a statistical limit to an adverse event in a dataset. More specifically for example, the absence of neutropenia in a subset of data, at a p-value of <0.05, could be used as the filter criterion such that a subset of data corresponding to an absence of neutropenia at the statistical significance level described by a p-value of <0.05 would be selected from the at least one dataset as the subset of the at least one dataset.

Operation 1108 shows applying at least a maximum mean incidence of one or more adverse events. For example, the study data analysis system 102 and/or the agent identification logic 126 and/or subset identification logic 128 and/or filter criterion logic 138 may apply a filter criterion that specifies a maximum mean value for the incidence of an adverse event in a dataset. More specifically, for example, a maximum mean cholesterol level of 250 mg/100 ml in a subset of data could be used as the filter criterion such that a subset of data corresponding to 250 mg/100 ml cholesterol or less would be selected from the at least one dataset as the subset of the at least one dataset.

Operation 1110 shows applying at least a maximum adverse event limit and a minimum efficacy limit. For example, the study data analysis system 102 and/or the agent identification logic 126 and/or subset identification logic 128 and/or filter criterion logic 138 may apply a filter criterion that specifies a maximum value for the incidence of an adverse event in a dataset and a minimum value for efficacy of the agent in question. More specifically, for example, a maximum level of 270 mg/100 ml of LDL cholesterol and a minimum blood pressure level of 140/100 in a subset of data following administration of a thiazide diuretic could be used as the Filter criterion such that a subset of data corresponding to 270 mg/100 ml cholesterol or less and blood pressure of 140/100 or less would be selected from the at least one dataset as the subset of the at least one dataset.

Operation 1112 shows applying one or more statistical filters. For example, the study data analysis system 102 and/or the agent identification logic 126 and/or subset identification logic 128 and/or filter criterion logic 138 may apply a filter criterion that specifies an adverse event level within a statistical range for the agent in question. More specifically, for example, a relative risk of developing a confirmed thrombotic event of less than 1.2 in a subset of data following administration of a COX-2 inhibitor could be used as the filter criterion such that a subset or data corresponding to a relative risk of less than 1.2 would be selected from the at least one dataset as the subset of the at least one dataset.

Operation 1114 shows applying at least a standard deviation statistical filter, a mean value statistical filter, a confidence interval statistical filter, an ANOVA statistical filter, or a p-value statistical filter. For example, the study data analysis system 102 and/or the agent identification logic 126 and/or subset identification logic 128 and/or filter criterion logic 138 may apply a filter criterion that specifies an adverse event level with a mean value filter. More specifically, for example, a mean pain score of 3-5 on the 0-5 Wong/Baker scale could be used as the filter criterion such that a subset of data corresponding to pain of 0-2 on the scale would be selected from the at least one dataset as the subset of the at least one dataset.

Operation 1116 shows applying at least a coincidence of data between two or more datasets. For example, the study data analysis system 102 and/or the agent identification logic 126 and/or subset identification logic 128 and/or filter criterion logic 138 may apply a filter criterion that specifies a coincidence of data between two or more datasets. More specifically, for example, the filter criterion could comprise a requirement for a statistically significant decrease in patient mortality associated with administration of torcetrapib and a requirement for statistically significant decrease in morbidity associated with administration of torcetrapib.

Operation 1118 shows applying at least one of an exclusion of data from two or more datasets or an inverse correlation of data between two or more datasets. For example, the study) data analysis system 102 and/or the agent identification logic 126 and/or subset identification logic 128 and/or filter criterion logic 138 may apply a filter criterion that excludes adverse event data above a specified level from two or more clinical trial datasets. More specifically, for example, the filter criterion could exclude data corresponding to patient mortality associated with administration of torcetrapib and data corresponding to statistically elevated systolic blood pressure associated with administration of torcetrapib. Alternatively, for example, the filter criterion could exclude data corresponding to a low post-stent fractional flow reserve measure and data corresponding to which serum levels of soluble intercellular adhesion molecule-1. These two factors bear an inverse relationship to each other with respect to restenosis following cardiac stent implantation.

Operation 1120 shows applying at least a correlation between an adverse event and an individual or croup characteristic. For example, the study data analysis system 102 and/or the agent identification logic 126 and/or subset identification logic 128 and/or filter criterion logic 138 may apply a filter criterion that specifies a correlation between an adverse event and an individual or group characteristic. More specifically, for example, in the context of an experimental surgical procedure for knee replacement, the filter criterion could exclude data from study subjects with high D-dimer levels and also exclude data from obese study subjects, both of which factors correlate with a higher risk for thrombosis.

Operation 1122 shows applying at least one filter criterion to the at least one dataset to identify a genomic data subset, proteomic data subset, hepatic enzyme profile data subset, RNA expression data subset, biochemical data subset, nutritional supplementation data subset, lifestyle data subset, medical history data subset, ethnicity data subset, age data subset, or gender data subset. For example, the study data analysis system 102 and/or the agent identification logic 126 and/or subset identification logic 128 and/or filter criterion logic 138 may apply a filter criterion that can identify various data subsets within at least one dataset. More specifically, for example, in the context of a filter criterion that excludes data corresponding to adverse events above a certain level, the subsequently identified subset of data may comprise, for example, a subpopulation that has a distinct hepatic enzyme profile, as depicted in FIG. 7, row 702.

Operation 1124 shows applying at least one filter criterion to the at least one dataset to identify a subset of the at least one dataset, the subset of the at least one dataset associated with a defined level of at least one allergy. For example, the study data analysis system 102 and/or the agent identification logic 126 and/or subset identification logic 128 and/or filter criterion logic 138 may apply a filter criterion that can identify data subsets within at least one dataset for which an allergic response is within a defined level. More specifically, for example, in the context of a filter criterion that excludes data corresponding to an allergic reaction above a certain level, the subsequently identified subset of data may comprise, for example, a subpopulation that has an allergic reaction below the defined level. For example, a subset of a dataset may have a level of inspiratory nasal resistance that is, for example, 20% or less as a measure of an allergic reaction to an agent. Other measures of allergic reactions known in the art may be used without limitation, such as skin tests and blood tests.

Operation 1126 shows applying at least one filter criterion to the at least one dataset to identify a subset of the at least one dataset, the subset of the at least one dataset associated with a defined level of at least one physiologic effect. For example, the study data analysis system 102 and/or the agent identification logic 126 and/or subset identification logic 128 and/or filter criterion logic 138 may apply a filter criterion to at least one dataset that can identify a physiological effect. More specifically, for example, in the context of a filter criterion that excludes data corresponding to, for example, headache above a certain level, the subsequently identified subset of data may comprise, for example, a subpopulation that does not experience headache following administration of an agent.

Operation 1128 shows applying at least one filter criterion to the at least one dataset to identify a subset of the at least one dataset, the subset of the at least one dataset associated with a defined level of at least one cardiovascular effect. For example, the study data analysis system 102 and/or the agent identification logic 126 and/or subset identification logic 128 and/or filter criterion logic 138 may apply a filter criterion to at least one dataset that can specify a cardiovascular effect. More specifically, for example, in the context of a filter criterion that excludes data corresponding to, for example, blood pressure above a certain level, the subsequently identified subset of data may comprise, for example, study subjects that exhibit blood pressure of 120/80 or lower following administration of an agent.

Operation 1130 shows applying at least one filter criterion to the at least one dataset to identify a subset of the at least one dataset, the subset of the at least one dataset associated with a defined level of at least one neutral or beneficial event that is not the intended effect of administration of the at least one agent. For example, the study data analysis system 102 and/or the agent identification logic 126 and/or subset identification logic 128 and/or filter criterion logic 138 may apply a filter criterion to at least one dataset that can specify an effect that is not necessarily harmful, but which nonetheless is not the intended effect of administration of the agent. More specifically, for example, in the context of a filter criterion that excludes data corresponding to, for example, high LDL cholesterol levels following administration of an anti-cancer drug, the subsequently identified subset of data may comprise, as a side effect, lower LDL cholesterol levels.

Operation 1132 shows applying at least one filter criterion to the at least one dataset to identify a subset of the at least one dataset, the subset of the at least one dataset characterized by one or more epigenetic parameters. For example, the study data analysis system 102 and/or the agent identification logic 126 and/or subset identification logic 128 and/or filter criterion logic 138 may apply a filter criterion that can identify a subset of data characterized by one or more epigenetic parameters within at least one dataset. More specifically, for example, a filter criterion may be employed that excludes data corresponding to adverse events above a certain level, and the subsequently identified subset of data may comprise, for example, a subpopulation that has a distinct epigenetic profile, for example, methylation of HP1 protein.

Operation 1134 shows applying at least one filter criterion to the at least one dataset to identify a subset of the at least one dataset characterized by one or more behavioral parameters. For example, the study data analysis system 102 and/or the agent identification logic 126 and/or subset identification logic 128 and/or filter criterion logic 138 may apply a filter criterion that can identify a subset of data characterized by one or more behavioral parameters within at least one dataset. More specifically, for example, a filter criterion may be employed that excludes data corresponding to high blood pressures and the subsequently identified subset of data may comprise, for example, a subpopulation that has a distinct behavioral profile, for example, subjects who exercise regularly, do not overeat, and actively manage their stress levels.

Operation 1136 shows applying at least one filter criterion to the at least one dataset to identify a subset of the at least one dataset characterized by one or more of lifestyle, exercise regimen, diet, nutritional regimen, dietary supplementation, concomitant medical therapy, or concomitant alternative medical therapy. For example, the study data analysis system 102 and/or the agent identification logic 126 and/or subset identification logic 128 and/or filter criterion logic 138 may apply a filter criterion that can identify a subset of data characterized by various parameters within at least one dataset. More specifically, for example, a filter criterion may be employed that excludes data corresponding to death following administration of a given agent, and the subsequently identified subset of data may comprise, for example, a subpopulation that did not die following administration of the agent, and which has a distinct profile in terms of, for example, dietary supplementation with niacin.

Operation 1138 shows applying at least one filter criterion to the at least one dataset to identify a subset of the at least one dataset characterized by one or more of linkage disequilibrium analysis profile, haplotype profile, single nucleotide polymorphism profile, or individual genetic sequence profile. For example, the study data analysis system 102 and/or the agent identification logic 126 and/or subset identification logic 128 and/or filter criterion logic 138 may apply a filter criterion that can identify a subset of data characterized by various genetic parameters within at least one dataset. More specifically, for example, a filter criterion may be employed that excludes data corresponding to lupus-like adverse events following administration of sulphasalazine, and the subsequently identified subset of data may comprise, for example, a subpopulation that does not experience the lupus-like adverse events, and which has a distinct profile in terms of, for example, a specific single nucleotide polymorphism of the HLA DR locus.

Operation 1140 shows applying at least one filter criterion to the at least one dataset to identify a subset of the at least one dataset having a significantly lower incidence of at least one adverse event than that of at least one reported clinical trial for the at least one agent. For example, the study data analysis system 102 and/or the agent identification logic 126 and/or subset identification logic 128 and/or filter criterion logic 138 may apply a filter criterion that can identify a subset of data that has a significantly lower incidence of at least one adverse event than that reported for at least one clinical trial. More specifically, for example, a filter criterion may be employed that excludes data corresponding to normal and above-normal incidence of myocardial infarction in subjects to whom Vioxx® was administered, and the subsequently identified subset of data may comprise, for example, a subpopulation that exhibits a below-normal incidence of myocardial infarction following administration of Vioxx®.

Operation 1142 shows applying at least one filter criterion to the at least one dataset to identify at least one subset of the at least one dataset exhibiting at least a defined level of efficacy in treating the at least one treatment target and a defined level of at least one adverse event associated with administration of the at least one agent. For example, the study data analysis system 102 and/or the agent identification logic 126 and/or subset identification logic 128 and/or filter criterion logic 138 may apply filter criteria that can identify a subset of data characterized by both a defined level of efficacy of the agent and a defined level of adverse events within at least one dataset. More specifically, for example, filter criteria may be employed that exclude data corresponding to myocardial infarction following administration of Vioxx®, and which exclude data corresponding to subjects for whom Vioxx® was ineffective in its intended effect of treating rheumatoid arthritis pain.

Figure 12:
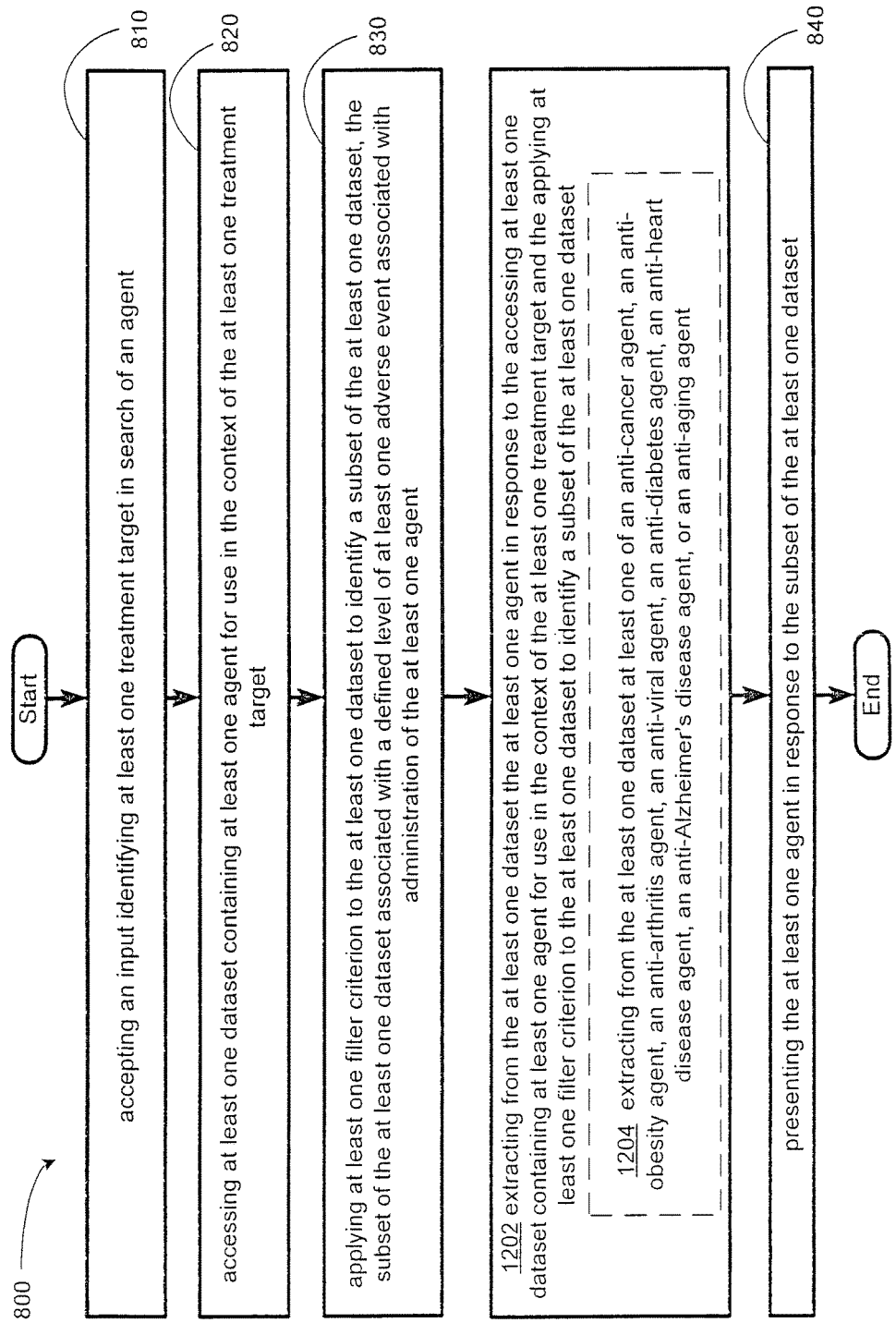
FIG. 12 illustrates an alternative embodiment of the example operational flow of FIG. 8.

FIG. 12 illustrates alternative embodiments of the example operational flow 800 of FIG. 8. FIG. 12 illustrates example embodiments where the defining operation 830 is followed by at least one additional operation. Additional operations may include operation 1202, and operation 1204.

Operation 1202 shouts extracting from the at least one dataset the at least one agent in response to the accessing at least one dataset containing at least one agent for use in the context of the at least one treatment target and the applying at least one filter criterion to the at least one dataset to identify a subset of the at least one dataset. For example, the study data analysis system 109 and/or the agent identification logic 126 and/or subset identification logic 128 and/or filter criterion logic 138 may extract from the at least one dataset the at least one agent based on the at least one subset of the at least one dataset. More specifically, for example, pemetrexed may be extracted from the at least one dataset based on its association with the subset of data showing low levels of neutropenia and no deficiency of vitamin B12 and/or cobalamin.

Operation 1204 shows extracting from the at least one dataset at least one of an anti-cancer agent, an anti-obesity agent, an anti-arthritis agent, an anti-viral agent, an anti-diabetes agent, an anti-heart disease agent, an anti-Alzheimer's disease agent, or an anti-aging agent. For example, the study data analysis system 102 and/or the agent identification logic 126 and/or subset identification logic 128 and/or filter criterion logic 138 may extract from the at least one dataset the at least one ACE inhibitor for treating hypertension, based on the at least one subset of the at least one dataset. More specifically, for example, an ACE inhibitor may be extracted from the at least one dataset based on its association with low levels of angio-edema in the non-black subset of data (See FIG. 7, row 704).

FIG. 13 illustrates alternative embodiments of the example operational flow 800 of FIG. 8. FIG. 13 illustrates example embodiments where the defining operation 830 may be followed by at least one additional operation. Additional operations may include operation 1302, operation 1304, 1306, 1308, and operation 1310.

Operation 1302 shows correlating the at least one subset of the at least one dataset associated with a defined level of at least one adverse event associated with administration of the at least one agent with subpopulation identifier data. For example, the study data analysis system 102 and/or the agent identification logic 126 and/or subset identification logic 128 and/or filter criterion logic 138 may access the http://www.clinicaltrialresults.org database to identify subsets of data associated with agents that show tolerance for an adverse event, for example pemetrexed for the treatment of malignant pleural mesothelioma, in terms of the adverse event neutropenia. Such identification may also identify subsets/subpopulations that experience at least adequate efficacy in terms of tumor response rate. Such data is available at http://www.clinicalstudyresults.org/documents/company-study_36_0.pdf. This webpage describes a clinical trial conducted by Eli Lilly and Company entitled "A Single-blind Randomized Phase 3 Trial of ALIMTA® (pemetrexed) plus Cisplatin Versus Cisplatin Alone in Patients with Malignant Pleural Mesothelioma." This is the clinical trial that generated the data described in FIG. 6, rows 602, 604 and 606. The study data analysis system 102 and/or the agent identification logic 126 and/or subset identification logic 128 and/or filter criterion logic 138 may then correlate the subset/subpopulation of patients exhibiting low neutropenia following administration of pemetrexed with subpopulation identifier data, for example, subjects supplemented with folic acid and vitamin B12.

Operation 1304 shows correlating the at least one subset of the at least one dataset associated with a defined level of at least one adverse event associated with administration of the at least one agent with at least one of genetic data, epigenetic data, biochemical data, gene expression data, protein expression data, behavioral data, physiologic data, or demographic data. For example, the study data analysis system 102 and/or the agent identification logic 126 and/or subset identification logic 128 and/or filter criterion logic 138 may identify a subset of at least one dataset which is associated with, for example, a reduced level of at least one adverse event associated with administration of at least one agent in the context of at least one treatment target in search of an agent. The study data analysis system 102 and/or the agent identification logic 126 and/or subset identification logic 128 and/or filter criterion logic 138 may then correlate the subset of the at least one dataset with, for example, a specific genetic sequence that is also found in the subset of the at least one dataset, as the subpopulation identifier data.

Operation 1306 shows correlating the at least one subset of the at least one dataset associated with a defined level of at least one adverse event associated with administration of the at least one agent with at least one of age data, gender data, ethnicity data, race data, liver enzyme genotype data, or medical history data. For example, the study data analysis system 102 and/or the agent identification logic 126 and/or subset identification logic 128 and/or filter criterion logic 138 may identify a subset of at least one dataset which is associated with, for example, a reduced level of at least one adverse event associated with administration of at least one agent in the context of at least one treatment target in search of an agent. The study data analysis system 102 and/or the agent identification logic 126 and/or subset identification logic 128 and/or filter criterion logic 138 may then correlate the subset of the at least one dataset with, for example, a specific CYP single nucleotide polymorphism (i.e., liver enzyme genotype data) that is also found in the subset of the at least one dataset, as the subpopulation identifier data.

Operation 1308 shows correlating the at least one subset of the at least one dataset associated with a defined level of at least one adverse event associated with administration of the at least one agent with at least one of lifestyle data, exercise regimen data, diet data, nutritional regimen data, dietary supplementation data, concomitant medical therapy data, or concomitant alternative medical therapy data. For example, the study data analysis system 102 and/or the agent identification logic 126 and/or subset identification logic 128 and/or filter criterion logic 138 may identify a subset of at least one dataset which is associated with, for example, a reduced level of at least one adverse event associated with administration of at least one agent in the context of at least one treatment target in search of an agent. The study data analysis system 102 and/or the agent identification logic 126 and/or subset identification logic 128 and/or filter criterion logic 138 may then correlate the subset of the at least one dataset with, for example, concomitant administration of an anti-coagulation agent (i.e., concomitant medical therapy) that is also present in the subset of the at least one dataset, as the subpopulation identifier data.

Operation 1310 shows correlating the at least one subset of the at least one dataset associated with a defined level of at least one adverse event associated with administration of the at least one agent with at least one of linkage disequilibrium analysis data, haplotype data, single nucleotide polymorphism data, or individual genetic sequence data. For example, the study data analysis system 102 and/or the agent identification logic 126 and/or subset identification logic 128 and/or filter criterion logic 138 may identify a subset of at least one dataset which is associated with, for example, a reduced level of at least one adverse event associated with administration of at least one agent in the context of at least one treatment target in search of an agent. The study data analysis system 102 and/or the agent identification logic 126 and/or subset identification logic 128 and/or filter criterion logic 138 may then correlate the subset of the at least one dataset with, for example, a specific linkage disequilibrium indicator (e.g., D. D', r, $r^2$, or other measure of linkage disequilibrium known in the art) (i.e., linkage disequilibrium data) that is also found in the subset of the at least one dataset, as the subpopulation identifier data.

Figure 14:
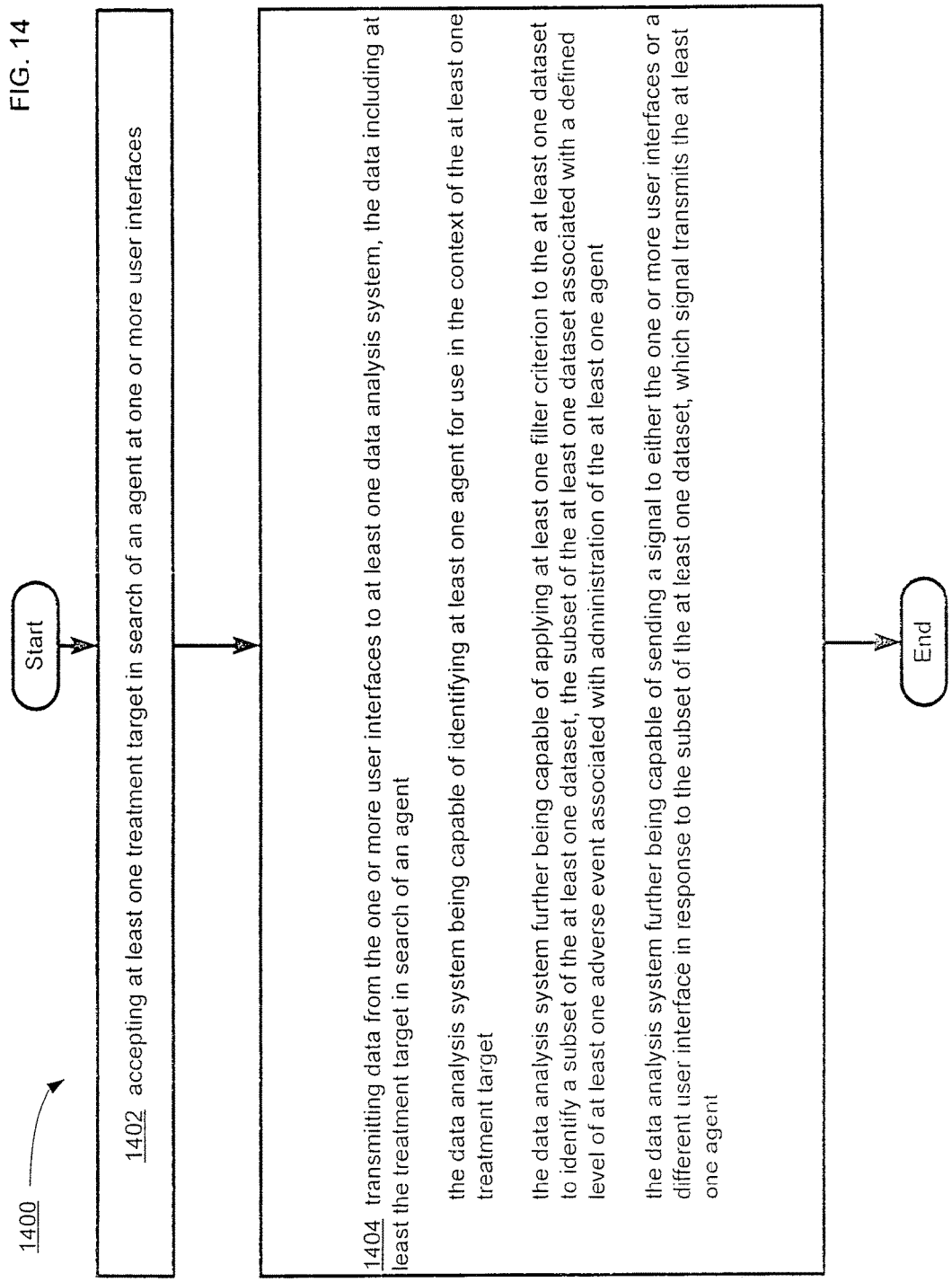
FIG. 14 illustrates an operational flow representing example operations related to computational systems for biomedical data.

FIG. 14 illustrates an operational flow 1400 representing example operations related to computational systems for biomedical data. After a start operation, operation 1402 shows accepting at least one treatment target in search of an agent at one or more user interfaces. Operation 1404 shows transmitting data from the one or more user interfaces to at least one data analysis system, the data including at least the treatment target in search of an agent, the data analysis system being capable of identifying at least one agent for use in the context of the at least one treatment target, the data analysis system further being capable of applying at least one filter criterion to the at least one dataset to identify a subset of the at least one dataset, the subset of the at least one dataset associated with a defined level of at least one adverse event associated with administration of the at least one agent, the data analysis system further being capable of sending a signal to either the one or more user interfaces or a different user interface in response to the subset of the at least one dataset, which signal transmits the at least one agent.

For example, the study data analysis system 102 and/or the subset identification logic 128 may accept at least one treatment target in search of an agent at one or more user interfaces, and transmit that data from the one or more user interfaces to at least one data analysis system, the data including at least the treatment target in search of an agent, the data analysis system being capable of identifying at least one agent for use in the context of the at least one treatment target, the data analysis system further being capable of applying at least one filter criterion to the at least one dataset to identify a subset of the at least one dataset, the subset of the at least one dataset associated with a defined level of at least one adverse event associated with administration of the at least one agent, the data analysis system further being capable of sending a signal to either the one or more user interfaces or a different user interface in response to the subset of the at least one dataset, which signal transmits the at least one agent.

Figure 15:
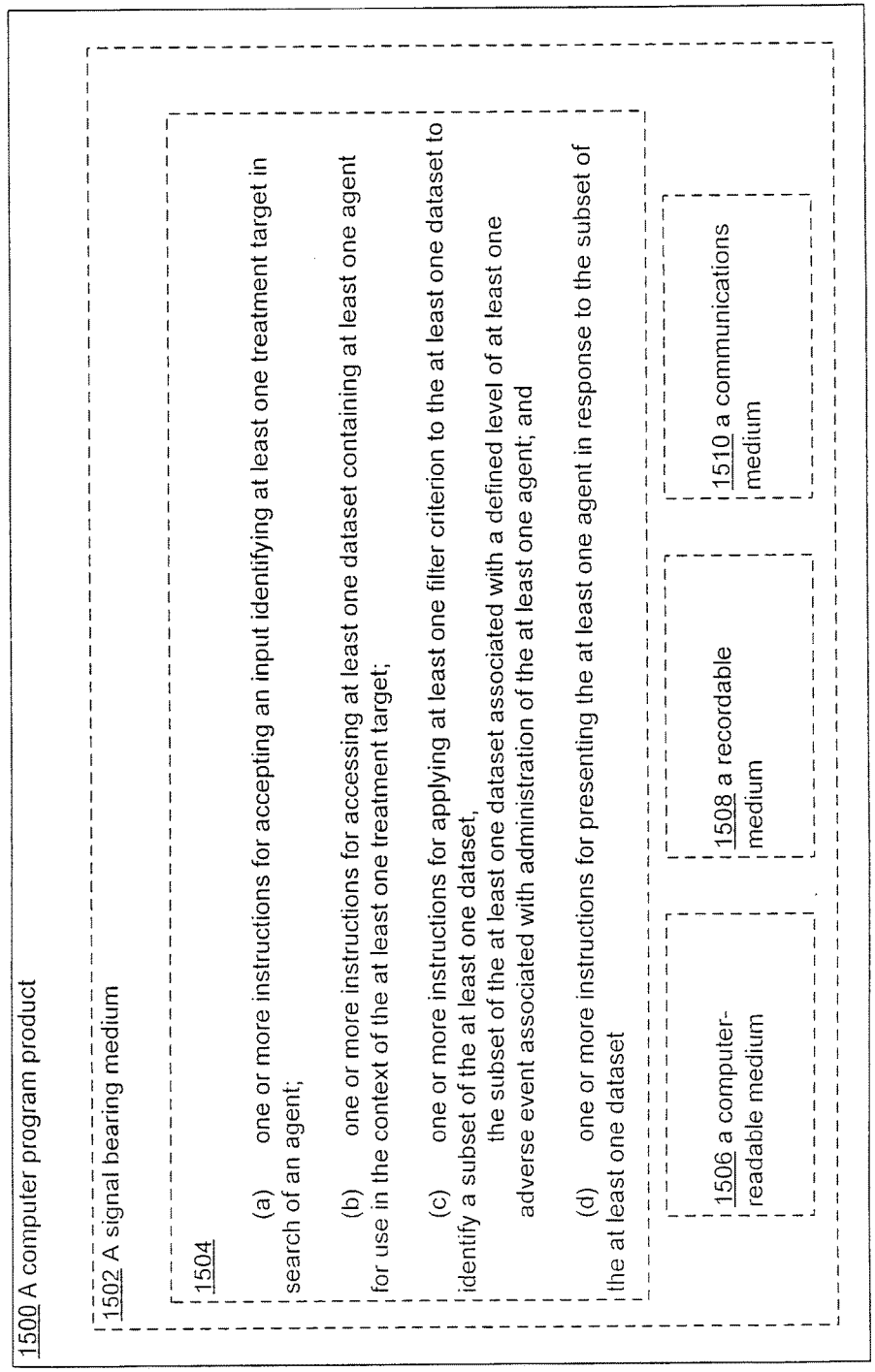
FIG. 15 illustrates a partial view of an example computer program product that includes a computer program for executing a computer process on a computing device.

FIG. 15 illustrates a partial view of an example computer program product 1500 that includes a computer program 1504 for executing a computer process on a computing device. An embodiment of the example computer program product 1500 is provided using a signal bearing medium 1502, and may include at one or more instructions for accepting an input identifying at least one treatment target in search of an agent; one or more instructions for accessing at least one dataset containing at least one agent for use in the context of the at least one treatment target; one or more instructions for applying at least one filter criterion to the at least one dataset to identify a subset of the at least one dataset, the subset of the at least one dataset associated with a defined level of at least one adverse event associated with administration of the at least one agent, and one or more instructions for presenting the at least one agent in response to the subset of the at least one dataset. The one or more instructions may be, for example, computer executable and/or logic-implemented implemented instructions. In one implementation, the signal-bearing medium 1502 may include a computer-readable medium 1506. In one implementation, the signal bearing medium 1502 may include a recordable medium 1508. In one implementation, the signal bearing medium 1502 may include a communications medium 1510.

Figure 16:
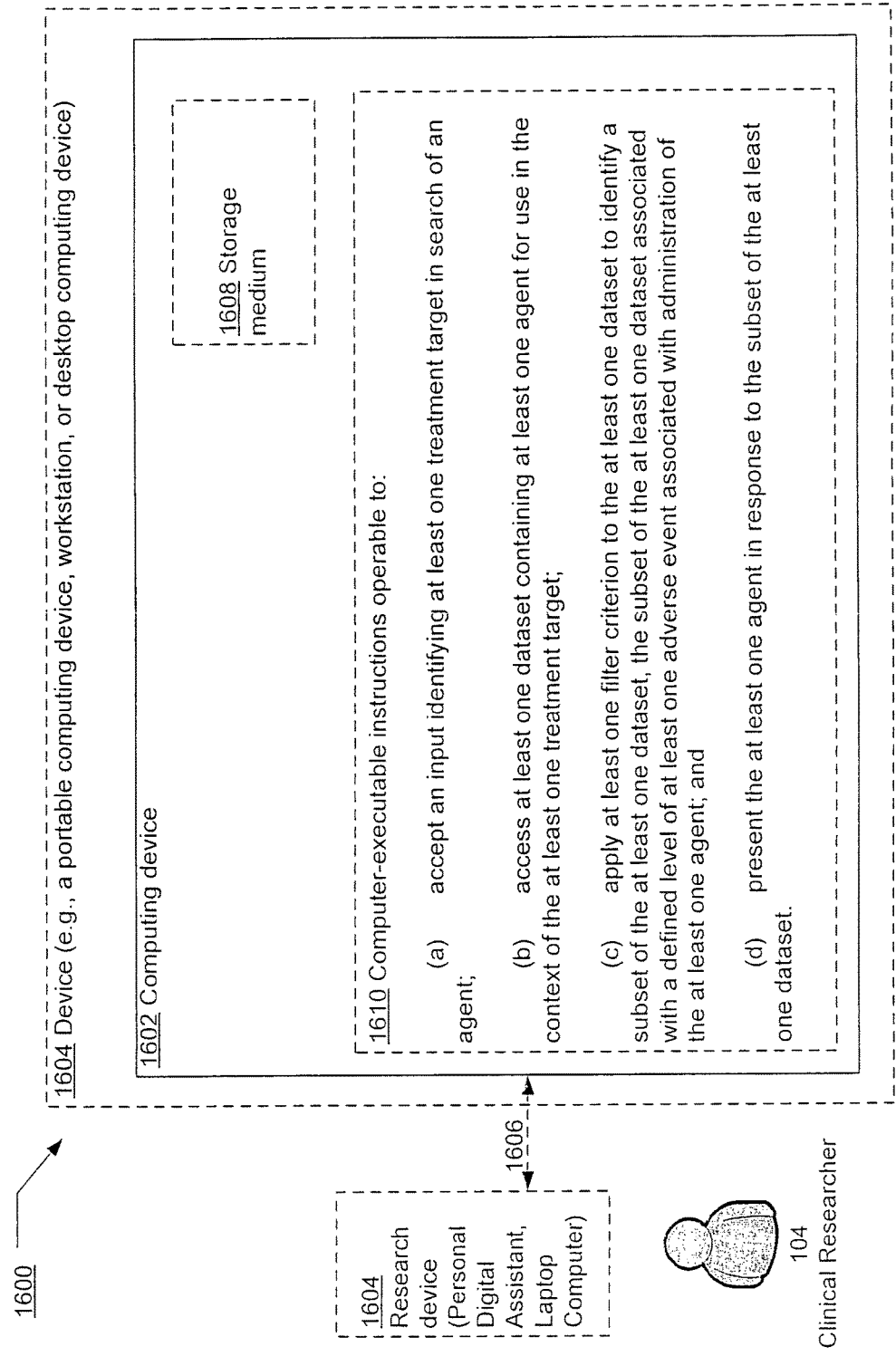
FIG. 16 illustrates an example device in which embodiments may be implemented.

FIG. 16 illustrates an example system 1600 in which embodiments may be implemented. The system 1600 includes a computing system environment. The system 1600 also illustrates the clinical researcher 104 using a device 1604, which is optionally shown as being in communication with a computing device 1602 by way of an optional coupling 1606. The optional coupling 1606 may represent a local, wide-area, or peer-to-peer network, or may represent a bus that is internal to a computing device (e.g., in example embodiments in which the computing device 1602 is contained in whole or in part within the device 1604). A storage medium 1608 may be any computer storage media.

The computing device 1602 includes computer-executable instructions 1610 that when executed on the computing device 1602 cause the computing device 1602 to accept an input defining at least one medical condition; to identify within one or more sets of study data at least one agent having a defined level of efficacy in treating the at least one medical condition; to identify at least one subpopulation having a defined tolerance for at least one adverse event associated with administration of the at least one agent, the at least one subpopulation exhibiting at least some defined level of efficacy upon administration of the at least one agent to the subpopulation; and to present the at least one agent in response to said identifying of at least one subpopulation. As referenced above and as shown in FIG. 16, in some examples, the computing device 1602 may optionally be contained in whole or in part within the research device 1604.

In FIG. 16, then, the system 1600 includes at least one computing device (e.g., 1602 and/or 1604). The computer-executable instructions 1610 may be executed on one or more of the at least one computing device. For example, the computing device 1602 may implement the computer-executable instructions 1610 and output a result to (and/or receive data from) the computing (research) device 1604. Since the computing device 1602 may be wholly or partially contained within the computing (research) device 1604, the research device 1604 also may be said to execute some or all of the computer-executable instructions 1610, in order to be caused to perform or implement, for example, various ones of the techniques described herein, or other techniques.

The research device 1604 may include, for example, a portable computing device, workstation, or desktop computing device. In another example embodiment, the computing device 1602 is operable to communicate with the clinician device 1604 associated with the clinical researcher 104 to receive information about the input from the clinical researcher 104 for performing the identifications and presenting the at least one agent.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing, cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing, the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality. Any two components capable of being so associated can also be viewed as being "operably/couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

While certain features of the described implementations have been illustrated is disclosed herein, many modifications, substitutions, changes and equivalents will now occur to those skilled in the art. It is, therefore, to be understood that the appended claims are intended to cover all such modifications and changes as fall within the true spirit of the embodiments of the invention.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly, recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phase "A or B" will be understood to include the possibilities of "A" or "B" or "A and B."

What is claimed is:

1. A method comprising:
    accepting at least one treatment target pertaining to at least one patient via at least one user interface;
    determining, based at least partly on a least one tissue sample from the at least one patient, at least one characteristic of a subpopulation identifier, wherein the at least one characteristic includes at least one of a genetic expression parameter, an epigenetic expression parameter, or a demographic parameter;
    receiving at least one input indicating at least one minimum level of efficacy for at least one treatment agent;
    identifying at least one defined level of incidence of at least one adverse event, the defined level of incidence associated with the at least one characteristic of a subpopulation identifier;
    identifying at least one treatment agent and at least one supplemental agent for use in the context of the at least one treatment target and the at least one defined level of incidence, including at least:
        applying the at least one defined level of incidence and the at least one characteristic of the subpopulation identifier to identify at least one particular clinically relevant study data;
        identifying a list of treatment agent options based at least partly on the defined level of incidence associated with the at least one characteristic of the subpopulation identifier, the at least one level of efficacy, and the identified at least one particular study data; and identifying a corresponding list of supplemental agent options known to at least one of increase the efficacy or decrease the level of incidence of the at least one treatment agent; and transmitting for display on at least one display device the list of treatment options and the corresponding list of supplemental agent options, the options ranked based at least partly on the level of efficacy and the level of incidence when the at least one treatment agent is administered in conjunction with the at least one supplemental agent and correlating the treatment agent options with corresponding supplemental agent options; and initiating administration of at least a portion of the at least one treatment agent and the at least one supplemental agent to the at least one patient.

2. A system comprising:

at least one electronic device including at least:

circuitry for accepting at least one treatment target pertaining to at least one patient;

circuitry for determining, based at least partly on a least one tissue sample from the at least one patient, at least one characteristic of a subpopulation, wherein the at least one characteristic includes at least one of a genetic expression parameter, an epigenetic expression parameter, or a demographic parameter;

circuitry for receiving at least one input indicating at least one minimum level of efficacy for at least one treatment agent;

circuitry for identifying at least one defined level of incidence of at least one adverse event, the defined level of incidence associated with the at least one characteristic of a subpopulation identifier;

circuitry for identifying at least one treatment agent and at least one supplemental agent for use in the context of the at least one treatment target and the at least one defined level of incidence, including at least:

circuitry for applying the at least one defined level of incidence and the at least one characteristic of the subpopulation identifier to identify at least one particular clinically relevant study data;

circuitry for identifying a list of treatment agent options based at least partly on the defined level of incidence associated with the at least one characteristic of the subpopulation identifier, the at least one level of efficacy, and the identified at least one particular study data; and circuitry for identifying a corresponding list of supplemental agent options known to at least one of increase the efficacy or decrease the level of incidence of the at least one treatment agent;

circuitry for transmitting for display on at least one display device the list of treatment options and the corresponding list of supplemental agent options, the options ranked based at least partly on the level of efficacy and the level of incidence when the at least one treatment agent is administered in conjunction with the at least one supplemental agent and correlating the treatment agent options with corresponding supplemental agent options; and circuitry for initiating administration of at least a portion of the at least one treatment agent and the at least one supplemental agent to the at least one patient.

3. The system of claim 2, wherein the circuitry for accepting at least one treatment target pertaining to at least one patient via at least one user interface comprises:

circuitry for accepting at least one of a medical condition treatment target, a nutritional deficiency treatment target, an obesity condition treatment target, a chronic condition treatment target, or an acute condition treatment target as the at least one treatment target.

4. The system of claim 2, wherein the circuitry for applying the at least one defined level of incidence and the at least one characteristic of the subpopulation identifier to identify at least one particular clinically relevant study data comprises:

circuitry for applying at least the at least one defined level of incidence and the at least one characteristic of the subpopulation identifier to at least one clinical trial dataset to identify a subset of the at least one clinical trial dataset, the subset of the at least one clinical trial dataset associated with the at least one characteristic of the subpopulation identifier and the at least one defined level of incidence of the at least one adverse event associated with administration of the at least one agent.

5. The system of claim 2, wherein the circuitry for transmitting for display on at least one display device the list of treatment agents and the corresponding list of supplemental agent options, the options ranked based at least partly on the level of efficacy and the level of incidence comprises:

circuitry for accepting, via the at least one user interface, at least one ranking factor for ranking one or more possible agents for use in treating the at least one treatment target.

6. The system of claim 2, wherein the circuitry for accepting at least one treatment target pertaining to at least one patient via at least one user interface comprises:

circuitry for accepting at least one preferred treatment agent via at least one user interface of a local device, and wherein the circuitry for applying the at least one defined level of incidence and the at least one characteristic of the subpopulation identifier to identify at least one particular clinically relevant study data includes at least:

circuitry for selecting particular study data from one or more databases of study data stored on one or more remote devices and accessible by the at least one local device via one or more networks wherein the circuitry for identifying a list of treatment agent options based at least partly on the defined level of incidence associated with the at least one characteristic of the subpopulation identifier, the at least one level of efficacy, and the identified at least one particular study data includes at least:

circuitry for determining whether the at least one preferred treatment agent meets the at least one level of efficacy and the at least one defined level of incidence, and wherein the circuitry for identifying a corresponding list of supplemental agent options known to at least one of increase the efficacy or decrease the level of incidence of the at least one treatment agent includes at least:

circuitry for identifying at least one supplemental agent known to at least one of increase the efficacy or decrease the level of incidence of the preferred treatment agent.

7. The system of claim 2, wherein the circuitry for identifying at least one defined level of incidence of at least one adverse event, the defined level of incidence associated with the at least one characteristic of a subpopulation identifier comprises:

circuitry for identifying at least one subpopulation that reports at least one defined level of incidence of the at least one adverse event;

circuitry for determining whether the at least one subpopulation correlates to the at least one characteristic of the subpopulation determined based at least partly on the at least one tissue sample from the at least one patient; and circuitry for accepting the at least one defined level of incidence based at least partially on the identified at least one subpopulation and the reported at least one defined level of incidence associated with the identified at least one subpopulation.

8. The system of claim 2, wherein the circuitry for identifying at least one defined level of incidence of at least one adverse event interface comprises:

circuitry for identifying at least one defined level of incidence that includes at least one indication of a subjective report of a tolerance level for the at least one adverse event.

9. The system of claim 2, wherein the circuitry for identifying at least one defined level of incidence of at least one adverse event comprises:

circuitry for identifying a level of incidence that includes at least one molecular marker indicative of a defined level of the at least one adverse event;

circuitry for determining whether the at least one molecular marker is present in the at least one tissue sample from the at least one patient, and wherein the circuitry for identifying a corresponding list of supplemental agent options known to at least one of increase the efficacy or decrease the level of incidence of the at least one treatment agent includes at least:

circuitry for identifying at least one supplemental agent known to have at least one effect associated with the at least one molecular marker indicative of the defined level of the at least one adverse event.

10. The system of claim 2, wherein the circuitry for identifying at least one defined level of incidence of at least one adverse event, the defined level of incidence associated with the at least one characteristic of a subpopulation identifier comprises:

circuitry for identifying at least one subpopulation that reports the at least one defined level of incidence of the at least one adverse event; and circuitry for determining whether the at least one adverse event is associated with at least one genetic expression common to the at least one subpopulation and the at least one patient, and wherein the circuitry for identifying at least one treatment agent and at least one supplemental agent for use in the context of the at least one treatment target and the at least one defined level of incidence includes at least:

circuitry for applying the at least one defined level of incidence and the at least one characteristic of the subpopulation identifier to identify a subset of the selected particular clinically relevant study data, the subset of the selected particular study data associated with the at least one characteristic of the subpopulation identifier and the at least one defined level of incidence of the at least one adverse event associated with administration of the at least one agent; and circuitry for identifying at least one agent for use based at least partially on at least one indication of minimum level of efficacy associated with the at least one characteristic of the subpopulation identifier and based at least partially on at least one indication of decreased incidence of the at least one adverse event.

11. The system of claim 2, wherein the circuitry for applying the at least one defined level of incidence and the at least one characteristic of the subpopulation identifier to identify at least one particular clinically relevant study data comprises:

circuitry for applying the at least one defined level of incidence and the at least one characteristic of the subpopulation identifier to identify at least one study conducted on clinically relevant patient populations, the clinical relevance based at least partly on the at least one tissue sample from the at least one patient.

12. The system of claim 11, wherein the circuitry for applying the at least one defined level of incidence and the at least one characteristic of the subpopulation identifier to identify at least one study conducted on clinically relevant patient populations comprises:

circuitry for applying at least one filter criterion to identify study data conducted on populations with at least one of a genetic expression parameter, an epigenetic expression parameter, or a demographic parameter characteristic similar to a patient for which the at least one treatment target is intended.

13. The method of claim 2, wherein the circuitry for identifying a corresponding list of supplemental agent options known to at least one of increase the efficacy or decrease the level of incidence of the at least one treatment agent comprises:

circuitry for identifying at least one supplemental agent to be administered during treatment with the identified treatment agents, the at least one supplemental agent associated with decreased incidence of the at least one adverse event in the clinically relevant subpopulation.

14. A system comprising:

a computing device; and instructions that when executed on the computing device cause the computing device to perform operations including at least:

accept at least one treatment target pertaining to at least one patient via at least one user interface;

determine, based at least partly on a least one tissue sample from the at least one patient, at least one characteristic of a subpopulation identifier, wherein the at least one characteristic includes at least one of a genetic expression parameter, an epigenetic expression parameter, or a demographic parameter;

receive at least one input indicating at least one minimum level of efficacy for at least one treatment agent;

identify at least one defined level of incidence of at least one adverse event, the defined level of incidence associated with the at least one characteristic of a subpopulation identifier;

identify at least one treatment agent and at least one supplemental agent for use in the context of the at least one treatment target and the at least one defined level of incidence, including at least:

apply the at least one defined level of incidence and the at least one characteristic of the subpopulation identifier to identify at least one particular clinically relevant study data;

identify a list of treatment agent options based at least partly on the defined level of incidence associated with the at least one characteristic of the subpopulation identifier, the at least one level of efficacy, and the identified at least one particular study data; and identify a corresponding list of supplemental agent options known to at least one of increase the efficacy or decrease the level of incidence of the at least one treatment agent;

transmit for display on at least one display device the list of treatment options and the corresponding list of supplemental agent options, the options ranked based at least partly on the level of efficacy and the level of incidence when the at least one treatment agent is administered in conjunction with the at least one supplemental agent and correlating the treatment agent options with corresponding supplemental agent options; and initiate administration of at least a portion of the at least one treatment agent and the at least one supplemental agent to the at least one patient.

15. The system of claim 2, wherein the circuitry for identifying a corresponding list of supplemental agent options known to at least one of increase the efficacy or decrease the level of incidence of the at least one treatment agent comprises:

circuitry for identifying a corresponding list of supplemental agent options known to decrease the level of incidence of the corresponding treatment agents and known to at least one of maintain or improve the efficacy of the corresponding treatment agents.

16. The system of claim 2, wherein the circuitry for transmitting for display on at least one display device the list of treatment agents and the corresponding list of supplemental agent options comprises:

circuitry for displaying, on at least one display of the at least one electronic device, the list of treatment agents and the corresponding list of supplemental agent options.

17. The system of claim 2, wherein the circuitry for determining, based at least partly on a least one tissue sample from the at least one patient, at least one characteristic of a subpopulation, wherein the at least one characteristic includes at least one of a genetic expression parameter, an epigenetic expression parameter, or a demographic parameter comprises:

circuitry for determining a particular risk associated with the at least one treatment target and at least one of the genetic expression parameter, the epigenetic expression parameter, or the demographic parameter.

18. The system of claim 2, wherein the circuitry for initiating administration of at least a portion of the at least one treatment agent and the at least one supplemental agent to the at least one patient comprises:

circuitry for initiating administration of a treatment consisting of at least one pharmaceutical agent and at least one non-pharmaceutical agent.

19. A computer program product comprising:

a non-transitory computer-readable medium bearing at least:

one or more instructions for accepting at least one treatment target pertaining to at least one patient via at least one user interface;

one or more instructions for determining, based at least partly on a least one tissue sample from the at least one patient, at least one characteristic of a subpopulation identifier, wherein the at least one characteristic includes at least one of a genetic expression parameter, an epigenetic expression parameter, or a demographic parameter;

one or more instructions for receiving at least one input indicating at least one minimum level of efficacy for at least one treatment agent;

one or more instructions for identifying at least one defined level of incidence of at least one adverse event via the at least one user interface, the defined level of incidence associated with the at least one characteristic of a subpopulation identifier;

one or more instructions for identifying at least one treatment agent and at least one supplemental agent for use in the context of the at least one treatment target and the at least one defined level of incidence, including at least:

one or more instructions for applying the at least one defined level of incidence and the at least one characteristic of the subpopulation identifier to identify at least one particular clinically relevant study data;

one or more instructions for identifying a list of treatment agent options based at least partly on the defined level of incidence associated with the at least one characteristic of the subpopulation identifier, the at least one level of efficacy, and the identified at least one particular study data; and one or more instructions for identifying a corresponding list of supplemental agent options known to at least one of increase the efficacy or decrease the level of incidence of the at least one treatment agent;

one or more instructions for transmitting for display on at least one display device the list of treatment options and the corresponding list of supplemental agent options, the options ranked based at least partly on the level of efficacy and the level of incidence when the at least one treatment agent is administered in conjunction with the at least one supplemental agent and correlating the treatment agent options with corresponding supplemental agent options; and one or more instructions for initiating administration of at least a portion of the at least one treatment agent and the at least one supplemental agent to the at least one patient.

20. The system of claim 14 wherein the computing device comprises:

one or more of a personal digital assistant (PDA), a laptop computer, a tablet personal computer, a networked computer, a computing system comprised of a cluster of processors, a computing system comprised of a cluster of servers, a workstation computer, and/or a desktop computer.

* * * * *